US008987430B2

(12) United States Patent
Patel et al.

(10) Patent No.: US 8,987,430 B2
(45) Date of Patent: *Mar. 24, 2015

(54) EFFICIENT AND SCALABLE PROCESS FOR THE MANUFACTURE OF FONDAPARINUX SODIUM

(71) Applicants: Payal Parth Patel, Fairview Heights, IL (US); Chun Ma, Ballwin, MO (US); Kevin K. Ohrr, Saint Charles, MO (US); Sourena Nadji, Olivette, MO (US)

(72) Inventors: Payal Parth Patel, Fairview Heights, IL (US); Chun Ma, Ballwin, MO (US); Kevin K. Ohrr, Saint Charles, MO (US); Sourena Nadji, Olivette, MO (US)

(73) Assignee: Reliable Biopharmaceutical Corporation, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,178

(22) Filed: Mar. 8, 2013

(65) Prior Publication Data
US 2013/0261291 A1 Oct. 3, 2013

Related U.S. Application Data

(63) Continuation of application No. 12/915,864, filed on Oct. 29, 2010, now Pat. No. 8,420,790.

(60) Provisional application No. 61/256,855, filed on Oct. 30, 2009.

(51) Int. Cl.
C07H 17/00 (2006.01)
C07H 17/02 (2006.01)
C07H 1/00 (2006.01)
C07H 1/06 (2006.01)

(52) U.S. Cl.
CPC ... C07H 1/00 (2013.01); C07H 1/06 (2013.01)
USPC ..................................... 536/18.5; 536/17.2

(58) Field of Classification Search
USPC ................................. 536/18.5, 17.2
See application file for complete search history.

(56) References Cited

U.S. PATENT DOCUMENTS

| 4,401,662 | A | 8/1983 | Lormeau et al. |
| 4,607,025 | A | 8/1986 | Petitou et al. |
| 4,774,231 | A | 9/1988 | Petitou et al. |
| 4,801,583 | A | 1/1989 | Petitou et al. |
| 4,818,816 | A | 4/1989 | Petitou et al. |
| 4,841,041 | A | 6/1989 | van Boeckel et al. |
| 4,987,223 | A | 1/1991 | Choay et al. |
| 5,234,935 | A | 8/1993 | Behner et al. |
| 5,378,829 | A | 1/1995 | Petitou et al. |
| 5,514,659 | A | 5/1996 | Petitou et al. |
| 5,529,985 | A | 6/1996 | Petitou et al. |
| 5,543,403 | A | 8/1996 | Petitou et al. |
| 5,773,605 | A | 6/1998 | Petitou et al. |
| 6,174,863 | B1 | 1/2001 | van Boeckel et al. |
| 6,271,215 | B1 | 8/2001 | Parish et al. |
| 6,462,183 | B1 | 10/2002 | Toth et al. |
| 6,528,497 | B1 | 3/2003 | Basten et al. |
| 6,534,481 | B1 | 3/2003 | Driguez et al. |
| 6,670,338 | B1 | 12/2003 | Petitou |
| 6,765,089 | B1 | 7/2004 | Toth et al. |
| 6,846,917 | B2 | 1/2005 | Seeberger et al. |
| 6,953,850 | B1 | 10/2005 | Dekany et al. |
| 7,468,358 | B2 | 12/2008 | Kennedy et al. |
| 7,541,445 | B2 | 6/2009 | Seifert et al. |
| 7,582,737 | B2 | 9/2009 | Hung et al. |
| 8,288,515 | B2 | 10/2012 | Nadji et al. |
| 2005/0020536 | A1 | 1/2005 | Branellec et al. |
| 2006/0079483 | A1 | 4/2006 | Hung et al. |
| 2006/0167237 | A1 | 7/2006 | West et al. |

FOREIGN PATENT DOCUMENTS

| JP | 63218691 | 9/1988 |
| JP | 63218691 A | 9/1988 |
| JP | 6094989 A | 4/1994 |
| WO | WO-2011014793 A2 | 2/2011 |

OTHER PUBLICATIONS

Synthesis from cellobiose, of a trisaccharide closely related to the GlcNAc->GlcA->GlcN segment of the anti-thrombin-binding sequence of heparin, Ichikawa et al., Carbohydrate Research, 141 (1985), 273-282.
Synthesis of heparin pentasaccharide fragment with a high affinity for antithrombin III employing cellobiose as a key starting material, Ichikawa et al., Tetrahedron Letters, vol. 27, No. 5, pp. 611-614 (1986).
Adinofli, et al., Activation of Disarmed 2-O-alkoxycarbonylated Glycosyl Trichloroacetimidates with Lanthanide Triflates: an Efficient Approach for the Synthesis of 1,2-trans Glycosides, Tetrahedron Letters 42 (2001) 5967-5969.
Adinofli, et al., Efficient Activation of Armed Glycosyl Trichloroacetimidates with Sm(Otf)3 in the Stereoselective Glycosidation of Saccharide Acceptors, Tetrahedron Letters 41 (2000) 9005-9008.
Allanson, et al., Synthesis of Phenyl 1-Thioglycopyranosiduronic Acids Using a Sonicated Jones Oxidation, Tetrahedrom Letters 39 (1998) 1889-1892.
Arndt, et al., Use of Cerny Epoxides for the Accelerated Synthesis of Glycosamingolycans; Organic Letters, 2003, vol. 5, No. 22, pp. 4179-4182.
Atha, et al., Contribution of 3-O- and 6-O-Sulfated Glucoasmine Residues in the Heparin-Induced Conformational Change in Antithrombin III, Biochemistry 1987, 26, 6454-6461.

(Continued)

Primary Examiner — Elli Peselev
(74) Attorney, Agent, or Firm — Blank Rome LLP

(57) ABSTRACT

The present invention relates to a process for the synthesis of the Factor Xa anticoagulent Fondaparinux and related compounds. The invention relates, in addition, to efficient and scalable processes for the synthesis of various intermediates useful in the synthesis of Fondaparinux and related compounds.

4 Claims, 2 Drawing Sheets

(56) References Cited

OTHER PUBLICATIONS

Basten, et al., Biologically Active Heparin-like Fragments with a "non-glycosamino" Glycan Structure. Part 3: o-alkylated-o-sulphated pentasaccharides, Bioorganic & Medicinal Chemistry Letter, vol. 2, Issue 9, Sep. 1992, pp. 905-910.
Bongat, et al., Recent Trends in the Synthesis of O-glycosides of 2-amino-2-deoxysugars, Carbohydrate Research 342 (2007) 374-406.
Casu, et al., The Structure of Heparin Oligosaccharide Fragments with High Anit-(factor Xa) Activity Containing the Minimal Antithrombin III-binding Sequence, Biochem. J. (1981) 197, 599-609.
Chiba, et al., Chemical Synthesis of L-Iduronic Acid-containing Di-saccharide Fragments of Heparin, Carbohydrate Research, 174 (1988) 253-264.
Code, et al., A Modular Strategy Toward the Synthesis of Heparin-like Oligosaccharides Using Monomeric Building Blocks in a Sequential Glycosylation Strategy, J. Am. Chem. Soc., 2005, 127 (11), 3767-3773.
Das, et al., Synthesis of Conformationally Locked L-Iduronic Acid Derivatives: Direct Evidence for a Critical Role of the Skew-Boat 2S0 Conformer in the Activiation of Antithrombin by Heparin, Chem. Eur. J. 2001, 7, No. 22, pp. 4821-4834.
Dodoni, et al., Synthesis of α- and β-Glycosyl Asparagine Ethylene Isosteres (C-Glycosyl Asparagines) via Sugar Acetylenes and Garner Aldehyde Coupling, J. Org. Chem. 2002, 67, 4475-4486.
Duchaussoy, et al., The First Total Synthesis of the Antithrombin III Binding Site of Porcine Mucosa Heparin, Bioorganic & Medicinal Chemistry Letters, vol. 1, No. 2, pp. 99-102, 1991.
Ernst, et al., Haloenamines—II. A Rapid and Efficient Synthesis of Carbohydrate 1,2-Orthoesters, Tetrahedron Letters, vol. 31, No. 43, pp. 6167-6170, 1990.
Fukuda, et al., Synthetic Approach Toward Antibiotic Tunicamycins. 3. Methyl 3,4,7,8-Tetra-O-acetyl-10-O-benzyl-2-benzyloxycarbonylamino-2,6-dideoxy-11,12-O-isopropylidene-β-L-dodecodialdo-(12R)-furanose-(12,9)-pyranosides-(1,5), Bull. Chem. Soc. Jpm., 55, 1574-1578 (1982).
Grundler, et al., Anwendung des Trichloroacetimidate-Verfahrens auf 2-Azidoglucose- und 2-Azidogalactose-Derivative, Liebigs Ann. Chem. 1984, 1826-1847.
Hadd, et al., Glycosyl iodides are Highly Efficient Donors Under Neutral Conditions, Carbohydrate Research 320 (1999) 61-69.
Hawley, et al., Investigation of the Hydrogen Bonding Properties of a Series of Monosaccharides in Aqueous Media by 1H NMR and IR Spectroscopy, Eur. J. Org. Chem., 2002, 1925-1936.
Hori, et al., Regioselective de-O-benzylation with Lewis Acids, J. Org. Chem., 1989, 54(6), 1346-1353.
Hung, et al., 1,6-Anhydro-β-L-hexopryanoses as Potent Synthons in the Synthesis of the Disaccharide Units of Bleomycin A2 and Heparin, J. Am. Chem. Soc. 2001, 123, 3153-3154.
Hung, et al., Novel Synthesis of 1,2:3,5-diO-isopropylidene-β-L-idofuranoside and its Derivatives at C6, Tetrahedron Letters 41 (2000) 77-80.
Ichikawa, et al., Synthesis of a Heparin Pentasaccharide Fragment with a High Affinity for Antithrombin III Employing Cellobiose as a Key Starting Material, Tetrahedron Letters, vol. 27, No. 5, pp. 611-614, 1986.
Ichikawa, et al., Synthesis of Methyl Glycoside Derivatives of Tri- and Penta-saccharides related to the Antithrombin III-binding sequence of Heparin, Employing Cellobiose as a Key Starting-Material, Carbohydrate Research, 172 (1988) 37-64.
Ichikawa, et al., Synthesis, From Cellobiose, of a Trisaccharide Closely Related to the GlcNAc'GlcA'GlcN Segment of the Antithrombin-binding Sequence of Heparin, Carbohydrate Research, 141 (1985) 273-282.
Izumi, et al., Synthesis of 5-Thio-I-fucose-Containing Disaccharides, as a Sequence-Specific Inhibitors, and 2'-Fucosyllactose, as a Substrate of α-I-Fucosidases, J. Org. Chem., 1997, 62, 992-998.

Jiang, et al., Copper(II)-Catalyzed Aerobic Oxidation or Primary Alcohols to Aldehydes in Ionic Liquid [bmpy]PF6, Organic Letters, 2005, vol. 7, No. 17, 3689-3692.
Karst, et al., Stereocontrolled Total Synthesis of Shark Cartilage Chondroitin Sulfate D-Related Tetra- and Hexasaccharide Methyl Glycosides, Eur. J. Org. Chem. 2002, 815-825.
Karst, et al., Sulfo-Protected Hexosamine Monosaccharides: Potentially Versatile Building Blocks for Glycosaminoglycan Synthesis, Organic Letters, 2003, vol. 5, No. 25, 4839-4842.
Ke, et a., Development of Specific Inhibitors for Heparin-binding Proteins Based on the Cobra Cardiotoxin Structure: an Effective Synthetic Strategy for Rationally Modified Heparin-like Disaccharides and a Trisaccharide, Carbohydate Research 340 (2005) 355-372.
Ke, et al., A Short Route to L-iduronic Acid Building Blocks for the Synthesis of Heparin-like Disaccharides, Tetrahedron Letters 44 (2003) 7767-7770.
Kim, et al., Selective Benzoylation of Diols with 1-(Benzoyloxy)benzotriazole, J. Org. Chem. 1985, 50, 1751-1752.
Koshida, et al., Synthesis and Biological Activity of Oligomer-model Compounds Containing Units of a Key Platelet-binding disaccharide of Heparin, Tetrahedrom Letters 40 (1999) 5725-5728.
Kovensky, et al., Binding of Heparan Sulfate to Fibroblast Growth Factor-2 Total Synthesis of a Putative Pentasaccharide Binding Site, Tetrahedron: Asymmetry, vol. 7, No. 11, pp. 3119-3128, 1996.
Kovesnky, et al., A Synthetic Heparan Sulfate Pentasaccharide, Exclusively Containing L-Iduronic Acid, Displays Higher Affinity for FGF-2 than its D-Glucuronic Acid-containing Isomers, Bioorganic & Medicinal Chemistry 7 (1999) 1567-1580.
La Feria, et al., Synthesis of Disaccahride Sub-Units of a New Series of Heparin Related Oligosaccharides, Tetrahedron 55 (1999) 9867-9880.
Lee, et al., Synthesis of Heparin Oligosaccharides, J. Am. Chem. Soc. 2004, 126, 476-477.
Lei, et al., Synthesis of a 3-Deoxy-L-iduronic Acid Containing Heparin Pentasaccharide to Probe the Conformation of the Antithrombin III Binding Sequence, Bioorganic & Medicinal Chemistry 6 (1998) 1337-1346.
Leteux, et al., An electroophile-mediated Cyclization on the 1,6-anhydro-D-Glucopyranose Framework, Carbohydate Research, 242 (1993) 119-130.
Lohman, et al., A Stereochemical Surprise at the Late Stage of the Synthesis of Fully N-Differentiated Heparin Oligosaccharides Containing Amino, Acetamido, and N-Sulfonate Groups, J. Org. Chem., 2004, 69 (12) 4081-4093.
Lohman, et al., Synthesis of Iduronic Acid Building Blocks for the Modular Assembly of Glycosaminoglycans, J. Org. Chem. 2003, 68, 7559-7561.
Lu, et al., Synthesis of 48 Disaccharide Building Blocks for the Assembly of Heparin and Heparan Sulfate Oligosaccharide Library, Organic Letters, 2006, vol. 8, No. 26, 5995-5998.
Lubineau, et al., New Accesses to L-iduronyl Synthons, Tetrahedrom Letters 41 (2000) 307-311.
Luo, et al., Synthesis of D-ribo-C18-phytosphingosine from D-glucosamine via the D-allosamine Derivatives as Key Intermediates, Tetrahedron Letters 43 (2002) 4889-4892.
Ohashi, et al., Use of Polysytrene-Supported DBU in the Synthesis and ?-Selective Glycosylation Study of the Unstable Schmidt Donor of L-Kedaresamine, Organic Letters, 2004, vol. 6, No. 5, 719-722.
Orgueira, et al., Conformational Locking of the Glycosyl Acceptor for Stereocontrol in the Key Step in the Synthesis of Heparin, Angew. Chem. Int. Ed. 2002, 41, No. 12, pp. 2128-2131.
Orgueira, et al., Modular Synthesis of Heparin Oligosaccharides, Chem. Eur. J. 2003, 9, No. 1, pp. 140-169.
Paulsen, et al., Stereoselektive Synthese ?-glycosidisch verknupfter Di- and Oligosaccharide der 2-amino-2-desoxy-D-glucopyranose, H. Paulsen and W. Stenzel, Chem. Ber. 111, 2334-2347 (1978).
Petitou, et al., A Unique Trisaccharide Sequence in Heparin Mediates the Early Step of Antithrombin III Activation, Glycobiology vol. 7, No. 3, pp. 323-327, 1997.

(56) References Cited

OTHER PUBLICATIONS

Petitou, et al., Conformational Flexibility: A New Concept for Explaining Binding and Biological Properties of Iduronic Acid-Containing Glycosaminoglycans, © 1988, Elsevier Publications Cambridge, TIBS13, Jun. 1988, pp. 221-225.

Poletti, et al., Chemical Contributions to Understanding Heparin Activity: Synthesis of Related Sulfated Oligosaccharides, Eur. J. Org. Chem. 2003, 2999-3024.

Popelova, et al., A Concise Synthesis of 4-nitrophenyl 2-azido-2-deoxy- and 2-acetamido-2-doexy-D-mannopyranosides, Carbohydrate Research 340 (2005) 161-166.

Sakairi, et al., Facile Preparation of 1,6-Anhydro-2-azido-3-O-benzyl-2-deoxy-?-D-glucopyranose and its 4-O-Substituted Derivatives, Bull Chem. Soc. Jpn., 67, 1756-1758 (1994).

Tabeur, et al., L-iduronic Acid Derivatives as Glycosyl Donors, Carbohydrate Research 281 (1996) 253-276.

Tailler, et al., An Expeditious and Stereocontrolled Preparation of 2-Azido-2-deoxy-?-D-glucopyranose Derivatives from D-Glucal, J. Chem. Soc. Perkin Trans, 1992, pp. 3163-3164.

Thunberg, et al., Further Characterization of the Antithromobin-Binding Sequence in Heparin, Carbohydrate Research, 100 (1982) 393-410.

van Bockl, et al., Progress in the Chemistry of Organic Natural Product, Fortschritte der Chemi organischer Naturstoff, © 1992 by Springer-Verlag/Wien, Chemical Synthesis of Heparain Fragments and Analogues, Petitou, et al., pp. 144-209.

Van Boeckel, et al., Substituent Effects of Carbohydrate Coupling Reactions Promoted by Insoluble Silver Salts, Tetrahedron, vol. 40, No. 20 pp. 4097 to 4107 (1984).

Van Boeckel, et al., Synthesis of a Pentasaccharide Corresponding to the Antithrombin III Binding Fragment of Heparin, J. Carbohydrate Chemistry, 4(3), 293-321 (1985).

Van Boeckel, et al., t-Butyldimethylsilyl (TBDMS) as Protective Group in Carbohydrate Chemistry Migration of the TBDMS Group in Trans-Diol Systems, Recl. Tray. Clim Pays-Bas 102, 415-416 (1981).

van Boeckel, et al., The Unique Antithrombin III Binding Domain of Heparin: A Lead to New Synthetic Antithrombotics, Angewandte Chemie International Edition in English, vol. 32, No. 12, Dec. 1993, pp. 1671-1818.

Van den Bos, et al., Thioglycuronides: Synthesis and Application in the Assembly of Acidic Oligosaccharides, Organic Letters, 2004, vol. 6, No. 13, 2165-2168.

Van der Klein, et al., Synthesis of a Cell Wall Component of Haemophilus (Actinobacillus) Plueropneumoniae Serotype 5, Tetrahedron vol. 48, No. 22, pp. 4649-4658, 1992.

Wessel, et al., Synthesis of an N-acetylated Heparin Pentasaccharide and its Anticoagulant Activity in Comparison with the Heparin Pentasaccharide with High Anti-Factor-Xa Activity, Helvetica Chimca Acta, vol. 72 (1989), 72(6), 1268-77, 1989.

Xue, et al., A Facile Synthesis of Cerny Epoxides and Selectively Blocked Derivatives of 2-azido-2-deoxy-?-D-Glucopyranose, Tetrahedron Letters 42 (2001) 6487-6489.

Yu, et al., Novel Efficient Routes to Heparin Monosaccharides and Disaccharides Achieved via Regio- and Stereoselective Glycosidation, Organic Letters, 2004, vol. 6, No. 5, 723-726.

Zhou, et al., Toward Synthesis of the Regular Sequence of Heparin: Synthesis of Two Tetrasaccharide Precursors, Carbohydrate Research 341 (2006) 1619-1629.

Zhu, et al., New Principles for Glycoside-Bond Formation, Angew. Chem. Int. Ed. 2009, 48, 1900-1934.

Van Boeckel, et al., A Note on the Use of Porous Silver Silicates as Promoter in Carbohydrate Coupling Reactions; Recl. Tray. Chim. Pays-Bas 106, 596-598 (1987).

Tamura, et al., Synthetic Approach Towards Sulfated Chondroitin di-, tri- and tetrasaccharides corresponding to the Repeating Unit, Carbohydrate Research 305 (1998) 43-65.

Sinay, et al., Preliminary Communication, Total Synthesis of a Heparin Pentasaccharide Fragment Having High Affinity for Antithrombin III, Carbohydrate Research, 132 (1984) C5-C9.

McBride, et al., A Novel Synthesis of 1,2-cis-Disaccharides, Journal of the American Chemical Society, 99:20, Sep. 28, 1977.

Van den Bos, et al., Preparation of 1-Thio Uronic Acid Lactones and Their Use in Oligosaccharide Synthesis, Organic Letters, 2005, vol. 7, No. 10, 2007-2010.

Petursson, et al., Protecting Groups in Carbohydrates Chemistry, Vo. 74, No. 11, Nov. 1997, Journal of Chemical Education (1297-1303.

Oikawa, et al., One-pot Preparation and Activation of Glycosyl Trichloroacetimidates: Operationally Simple Glycosylation Induced by Combined Use of Solid-supported, reactivity-opposing reagents, Tetrahedron Letters 45 (2004) 4039-4042.

Yu, et al., Glycosyl Trifluoroacetimidates. Part I: Preparation and Application as New Glycosyl Donors, Tetrahedron Letters 42 (2001) 2405-2407.

Ganguli, et al., α-βSelectivity in the Synthesis of 3-substituted, 4-methyl Umbelliferone Glycosides of N-acetyl Glucoasmine and Chitobiose, Tetrahedron Asymmetry 16 (2005) 411-424.

Hernandez, et al., General Stereoselective Synthesis of Chemically Differentiated α-Diamino Acids: Synthesis of 2,6-Disaminopimelic and 2,7-Diaminosuberic Acids, J. Org. Chem. 2001, 66, 4934-4938.

Lohman, et al., One-pot Conversion of Glycals to cis-1,2-lsopropylidene-α-glycosides, J. Org. Chem. 2003, 68, 7541-7543.

Manabe, et al., N-Benzyl-2,3-oxazolidinon as a Glycosyl Donor for Selective α-Glycosylation and One-Pot Oligosaccharide Synthesis Involving 1,2-cis-Glycosylation, J. Am. Chem. Soc. 2006, 128, 10666-10667.

Petitou, et al., Synthesis of Heparin Fragments, a Chemical Synthesis of the Pentasaccharide O-(2-Deoxy-2-Sulfamido-6-O-Sulfo-α-D-Glucopyranosyl)-1à4)-O-(2-Deoxy-2-sulfamido-3,6-di-o-sulfo-α-D-glucopyranosyl)-(1à4)-O-(2-O-sulfo-α-L-idopyranosyluronic acid)-(1à4)-2-deoxy-2-sulfamido-6-o-sulfo-D-glucopyranose decasodium salt, a Heparin Fragment Having High Affinity for Antithrombin III, Carbohydrate Research, 147 (1986) 221-236.

Petitou, et al., Synthesis of Heparin Fragments: A Methyl α-Pentaoside with High Affinity for Antithrombin III, Carbohydrate Research, 167 (1987) 67-75.

Sakairi, et al., Insertion of a D-Glucosamine Residue into the α-Cyclodextrin Skeleton; A Model Synthesis of Chimera Cyclodextrains, J. Chem. Soci., Chem. Commun., 1991, pp. 289-290.

Partial International Search Report issued in PCT/US2012/023610 issued Mar. 19, 2013.

EFFICIENT AND SCALABLE PROCESS FOR THE MANUFACTURE OF FONDAPARINUX SODIUM

This application is a continuation of U.S. patent application Ser. No. 12/915,864, filed Oct. 29, 2010, now U.S. Pat. No. 8,420,790, and claims the benefit of U.S. Provisional Patent Application No. 61/256,855, filed Oct. 30, 2009, each of which is hereby incorporated by reference. This application incorporates by reference U.S. Provisional Application Ser. No. 61/230,557, filed Jul. 31, 2009 and U.S. patent application Ser. No. 12/847,719, filed Jul. 30, 2010, now U.S. Pat. No. 8,288,515.

FIELD OF THE INVENTION

The present invention relates to a process for the synthesis of the Factor Xa anticoagulent Fondaparinux and related compounds. The invention relates, in addition, to efficient and scalable processes for the synthesis of various intermediates useful in the synthesis of Fondaparinux and related compounds.

BACKGROUND OF THE INVENTION

In U.S. Pat. No. 7,468,358, Fondaparinux sodium is described as the "only anticoagulant thought to be completely free of risk from HIT-2 induction." The biochemical and pharmacologic rationale for the development of a heparin pentasaccharide in *Thromb. Res.*, 86(1). 1-36, 1997 by Walenga et al. cited the recently approved synthetic pentasaccharide Factor Xa inhibitor Fondaparinux sodium. Fondaparinux has also been described in Walenga et al., *Expert Opin. Investig. Drugs*, Vol. 11, 397-407, 2002 and Bauer, *Best Practice & Research Clinical Hematology*, Vol. 17, No. 1, 89-104, 2004.

Fondaparinux sodium is a linear octasulfated pentasaccharide (oligosaccharide with five monosaccharide units) molecule having five sulfate esters on oxygen (O-sulfated moieties) and three sulfates on a nitrogen (N-sulfated moieties). In addition, Fondaparinux contains five hydroxyl groups in the molecule that are not sulfated and two sodium carboxylates. Out of five saccharides, there are three glucosamine derivatives and one glucuronic and one L-iduronic acid. The five saccharides are connected to each other in alternate α and β glycosylated linkages, as shown below.

Fondaparinux sodium is a chemically synthesized methyl glycoside derivative of the natural pentasaccharide sequence, which is the active site of heparin that mediates the interaction with antithrombin (Casu et al., *J. Biochem.*, 197, 59, 1981). It has a challenging pattern of O- and N-sulfates, specific glycosidic stereochemistry, and repeating units of glucosamines and uronic acids (Petitou et al., *Progress in the Chemistry of Organic Natural Product*, 60, 144-209. 1992).

The monosaccharide units comprising the Fondaparinux molecule are labeled as per the structure shown above, with the glucosamine unit on the right referred to as monosaccharide A and the next, an uronic acid unit to its left as B and subsequent units, C, D and F respectively. The chemical synthesis of Fondaparinux starts with monosaccharides of defined structures that are themselves referred to as Building Block A, Building Block B, DC Building Block and Monomer E, for differentiation and convenience, and they become the corresponding monosaccharides in Fondaparinux sodium.

Due to this complex mixture of free and sulfated hydroxyl groups, and the presence of N-sulfated moieties, the design of a synthetic route to Fondaparinux requires a careful strategy of protection and de-protection of reactive functional groups during synthesis of the molecule. Previously described syntheses of Fondaparinux all adopted a similar strategy to complete the synthesis of this molecule. This strategy can be envisioned as having four stages. The strategy in the first stage requires selective de-protection of five out of ten hydroxyl groups. During the second stage these five hydroxyls are selectively sulfonated. The third stage of the process involves the de-protection of the remaining five hydroxyl groups. The fourth stage of the process is the selective sulfonation of the 3 amino groups, in the presence of five hydroxyl groups that are not sulfated in the final molecule. This strategy can be envisioned from the following fully protected pentasaccharide, also referred to as the late-stage intermediate.

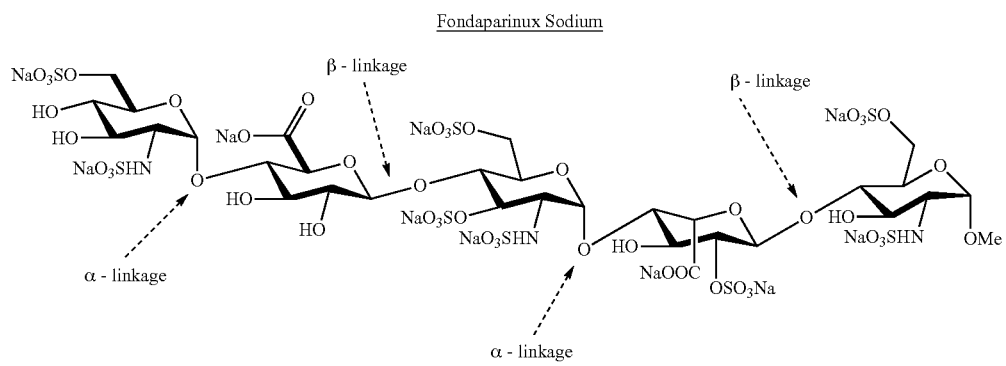

Fondaparinux Sodium

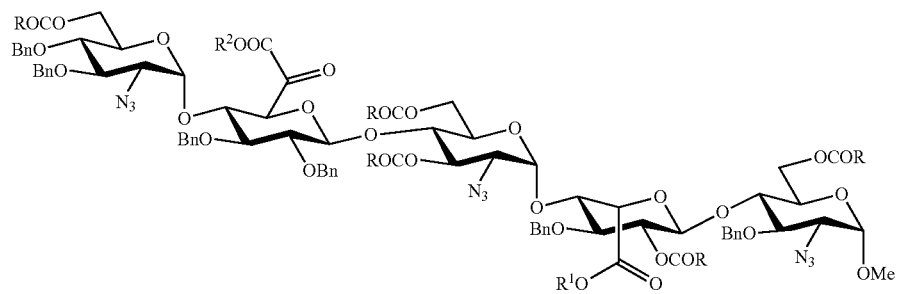

In this strategy, all of the hydroxyl groups that are to be sulfated are protected with an acyl protective group, for example, as acetates (R=CH$_3$) or benzoates (R=aryl) (Stages 1 and 2) All of the hydroxyl groups that are to remain as such are protected with benzyl group as benzyl ethers (Stage 3). The amino group, which is subsequently sulfonated, is masked as an azide (N$_3$) moiety (Stage 4). R$^1$ and R$^2$ are typically sodium in the active pharmaceutical compound (e.g., Fondaparinux sodium).

This strategy allows the final product to be prepared by following the synthetic operations as outlined below:

a) Treatment of the late-stage intermediate with base to hydrolyze (deprotect) the acyl ester groups to reveal the five hydroxyl groups. The two R$^1$ and R$^2$ ester groups are hydrolyzed in this step as well.

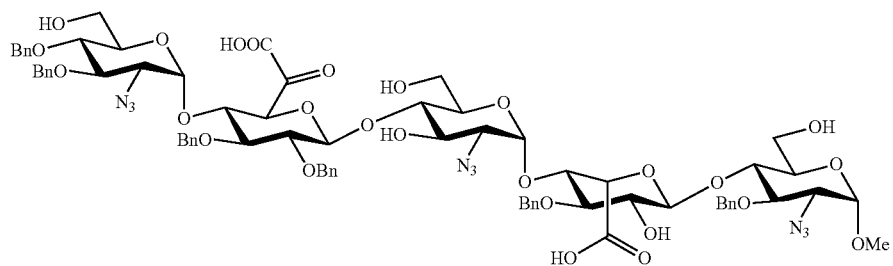

b) Sulfonation of the newly revealed hydroxyl groups.

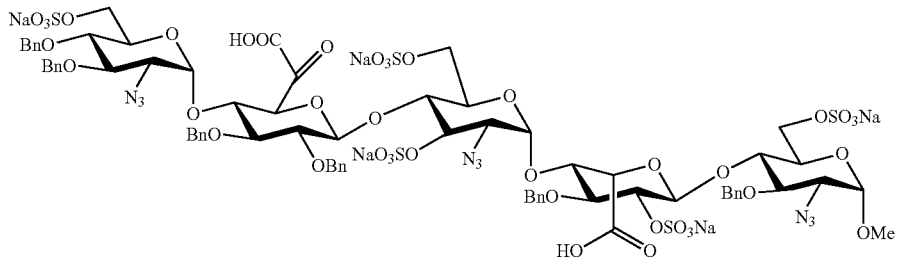

c) Hydrogenation of the 0-sulfated pentasaccharide to debenzylate the five benzyl-protected hydroxyls, and at the same time, unmask the three azides to the corresponding amino groups.

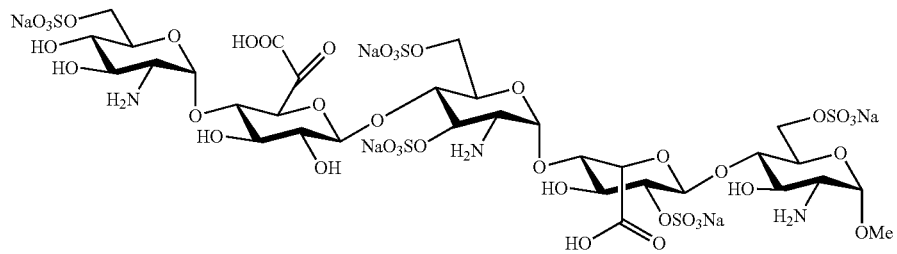

d) On the last step of the operation, the amino groups are sulfated selectively at a high pH, in the presence of the five free hydroxyls to give Fondaparinux.

A number of synthetic approaches have been developed in order to prepare fully protected pentasaccharides (EDCBA) that may be used in the synthesis of Fondaparinux sodium. The synthesis of EDCBA fragment, however, is complicated by the presence of different functional groups in varying positions on the pentasaccharide requiring an elaborate protection, deprotection strategy. See, e.g., L. Poletti et al., Eur. J. Org. Chem., 2999-3024, 2003; W. Hague et al., Chapter 17, "Modern Method in Carbohydrate Synthesis", Eds. Shaheer Khan and R. A. O'Neill; Harwood Academic Publisher GmbH, 403-436, 1996; M. Petitou et al., Progress in the Chemistry of Organic Natural Products, Vol. 60, 143-209, 1992, Springer-Verlag, New York, 1992).

Current methods for the synthesis fully protected pentasaccharides (EDCBA) typically require approximately 60 steps and result, therefore in low yields of product. Thus, scalability of the process is a major concern, as this directly affects the cost and time required to complete the manufacture of Fondaparinux Sodium.

Therefore, as will be appreciated, there is a need in the art for new synthetic procedures that produce Fondaparinux sodium and intermediates useful in the synthesis thereof. The processes of the present invention provide a unique, reliable and scalable synthesis of compounds such as Fondaparinux sodium.

SUMMARY OF THE INVENTION

Applicants have developed novel synthetic strategies for the synthesis of Fondaparinux sodium and intermediates useful in the preparation of Fondaparinux sodium. The processes described herein allow for efficient scale-up, require fewer synthetic steps and proceed with higher yields of product. The processes described herein also afford a better purity profile due to reduced β-methyl glucoside contamination in the final product.

One embodiment of the present invention is a process for the preparation of a protected heparinic pentasaccharide precursor to Fondaparinux sodium having the structure

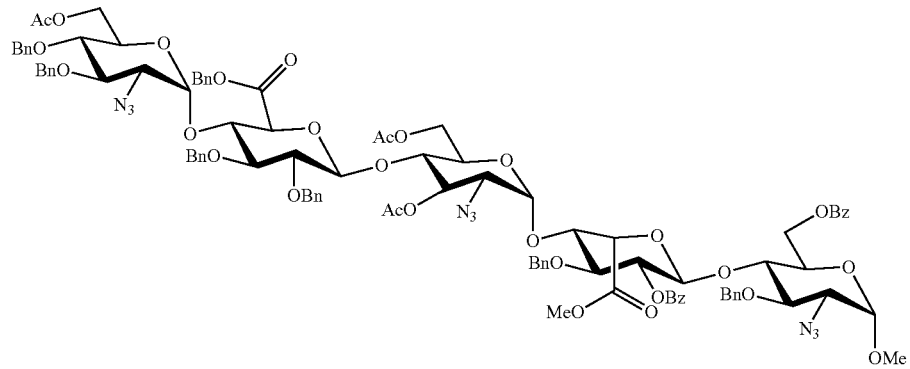

comprising the step of coupling a EDC trimer having the structure

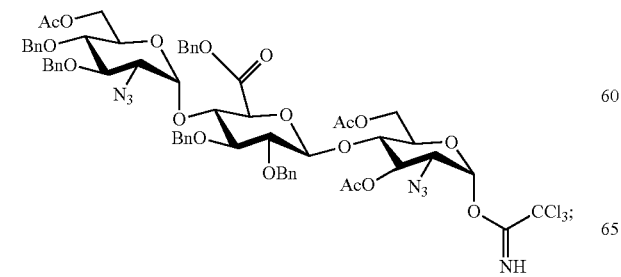

with a BA dimer having the structure

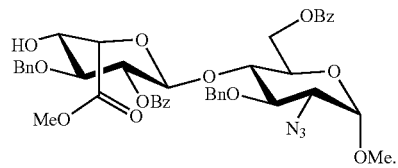

In another embodiment, the present invention relates to a process that further comprises converting the protected heparinic pentasaccharide precursor to Fondaparinux sodium.

Another embodiment of the present invention is a process for preparing EDC trimer having the formula

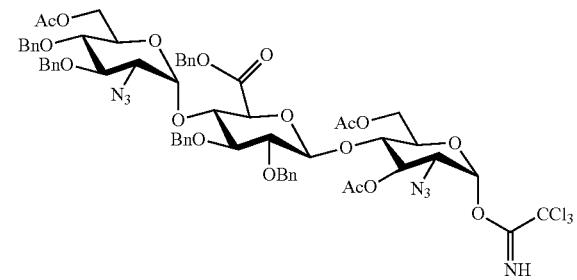

wherein the EDC trimer is prepared using a process (Schmidt glycosylation) comprising the steps:

(a) coupling an E monomer having the structure

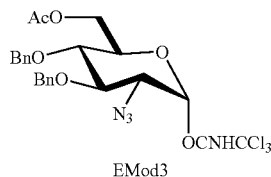

EMod3 to a DC Building Block having the structure

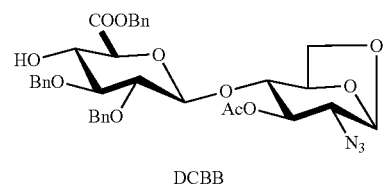

DCBB to obtain an EDC precursor having the structure

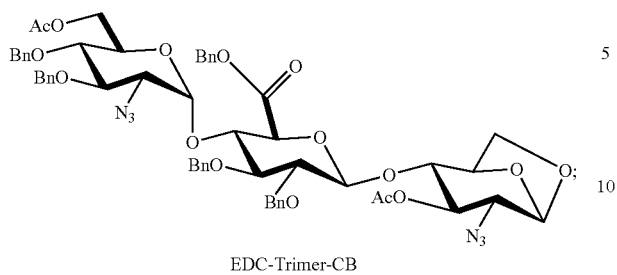

EDC-Trimer-CB and (b) converting the EDC precursor to the EDC trimer.

In another embodiment, the present invention relates to a process that further comprises converting the EDC trimer to Fondaparinux sodium.

Yet still another embodiment of the present invention is a process for preparing DC Building Block having the formula

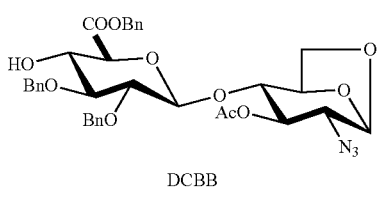

DCBB where the DC Building Block is prepared from 1,6-anhydro-cellobiose having the structure

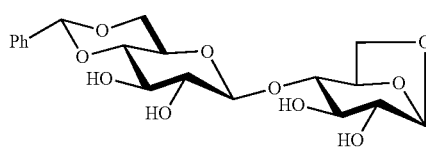

comprising at least four of the following steps:

(a) protecting 1,6-anhydrocellobiose to form CB1 having the structure

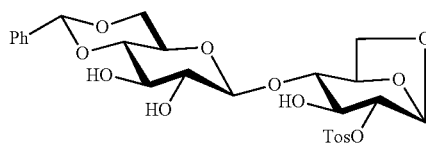

CB1

(b) tosylating CB1 to form CB2 having the structure

CB2

(c) reacting CB2 with base to form CB3 having the structure

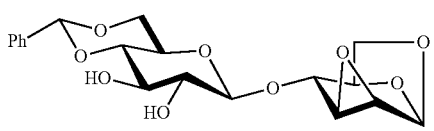

CB3

(d) protecting CB3 to form CB4 having the structure

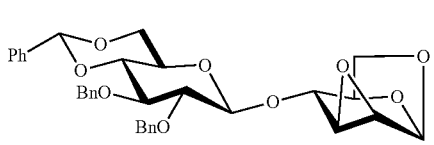

CB4

(e) reacting CB4 with azide to form CB5 having the structure

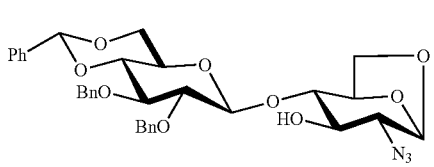

CB5

(f) acetylating CB5 to form CB6 having the structure

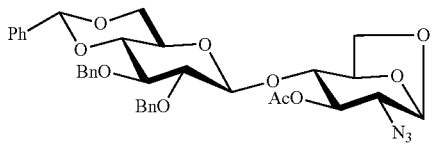

CB6

(g) deprotecting CB6 to form CB7 having the structure

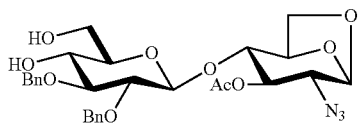

CB7

(h) oxidizing CB7 to form CB8 having the structure

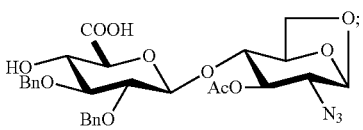

CB8 and (i) benzylating CB8 to form the DC dimer.

In certain embodiments, the process includes at least six steps from steps (a)-(i).

In further embodiments, the process includes all of steps (a)-(i).

Another embodiment of the present invention is a process wherein the BA dimer is prepared using a Schmidt glycosylation comprising the step of coupling a B monomer having the structure

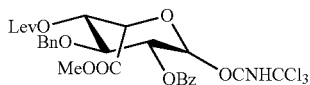

where Lev is levulinyl, Bn is benzyl, Bz is benzoyl and TCA is trichloroacetimidate, to an A monomer having the structure

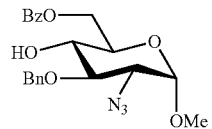

to form the BA dimer.

Another embodiment of the present invention is a process for preparing AMod5 [also referred to herein as Building block A] having the formula:

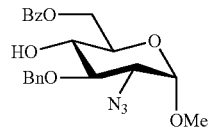

wherein monomer A is prepared from a compound of formula IntA1

IntA1

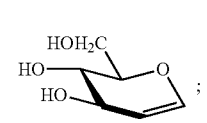

the process comprising the one or more of the following steps:

(a) cyclizing (oxidative-1,6-iodocyclizing) a compound of formula IntA1 to form a compound of formula IntA2:

IntA2

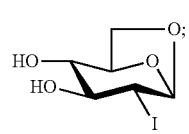

(b) epoxidizing a compound of formula IntA2 to form a Cerny epoxide in a compound of formula IntA2a:

IntA2a

(c) converting (p-methoxybenzylating) a compound of formula IntA2a to a compound of formula IntA3:

IntA3

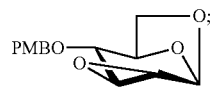

(d) converting (azide assisted ring opening of the Cerny epoxide) a compound of formula IntA3 to a compound of formula IntA4

IntA4

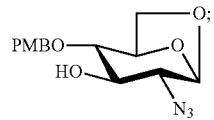

(e) converting (benzylating) a compound of formula IntA4 to a compound of formula Monomer A2 [also referred to as IntA5]

Monomer A2 [IntA5]

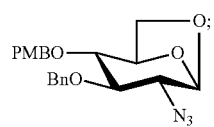

(f) converting (for example, by deprotecting PMB, anhydro ring opening and acetylating) a compound of formula Monomer A2 [also referred to as IntA5] to a compound of formula AMod1:

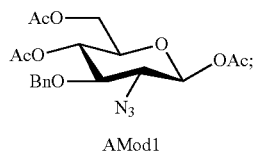

AMod1

(g) converting (α-methylglycosylating) a compound of formula AMod1 to a compound of formula AMod3:

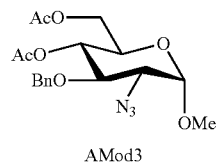

AMod3

(h) converting (deacetylating) a compound of formula AMod3 to a compound of formula AMod4:

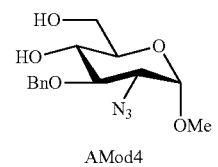

AMod4

(i) converting (benzoylating) a compound of formula AMod4 to AMod5 [also referred to as Building block A]

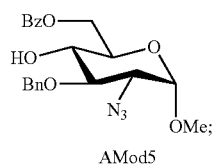

AMod5

(j) recrystallizing AMod5.

One embodiment of the present invention is a process wherein the AMod5 [also referred to as Building Block A] that is formed is substantially free of the β-methyl glycoside.

Additional embodiments of the present invention include a process where the protected heparinic pentasaccharide that is formed contains less than about 1%, less than about 0.5%, less than about 0.11%, less than about 0.05% or less than about 0.01% of the β-methyl glycoside.

A further embodiment of the present invention is a process for preparing a monosaccharide of the formula AMod3

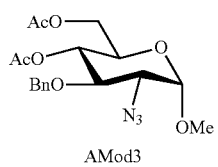

AMod3 comprising deprotecting PMB, anhydro ring opening, acetylating and α-methylglycosylating a compound of the formula Monomer A2 (also referred to as IntA5)

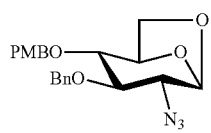

Monomer A2

A further embodiment of the present invention is a process for purifying a monosaccharide of formula Amod5:

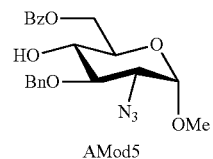

AMod5 comprising recrystallizing the monosaccharide from an organic solvent.

DETAILED DESCRIPTION OF THE INVENTION

Figure 1A:
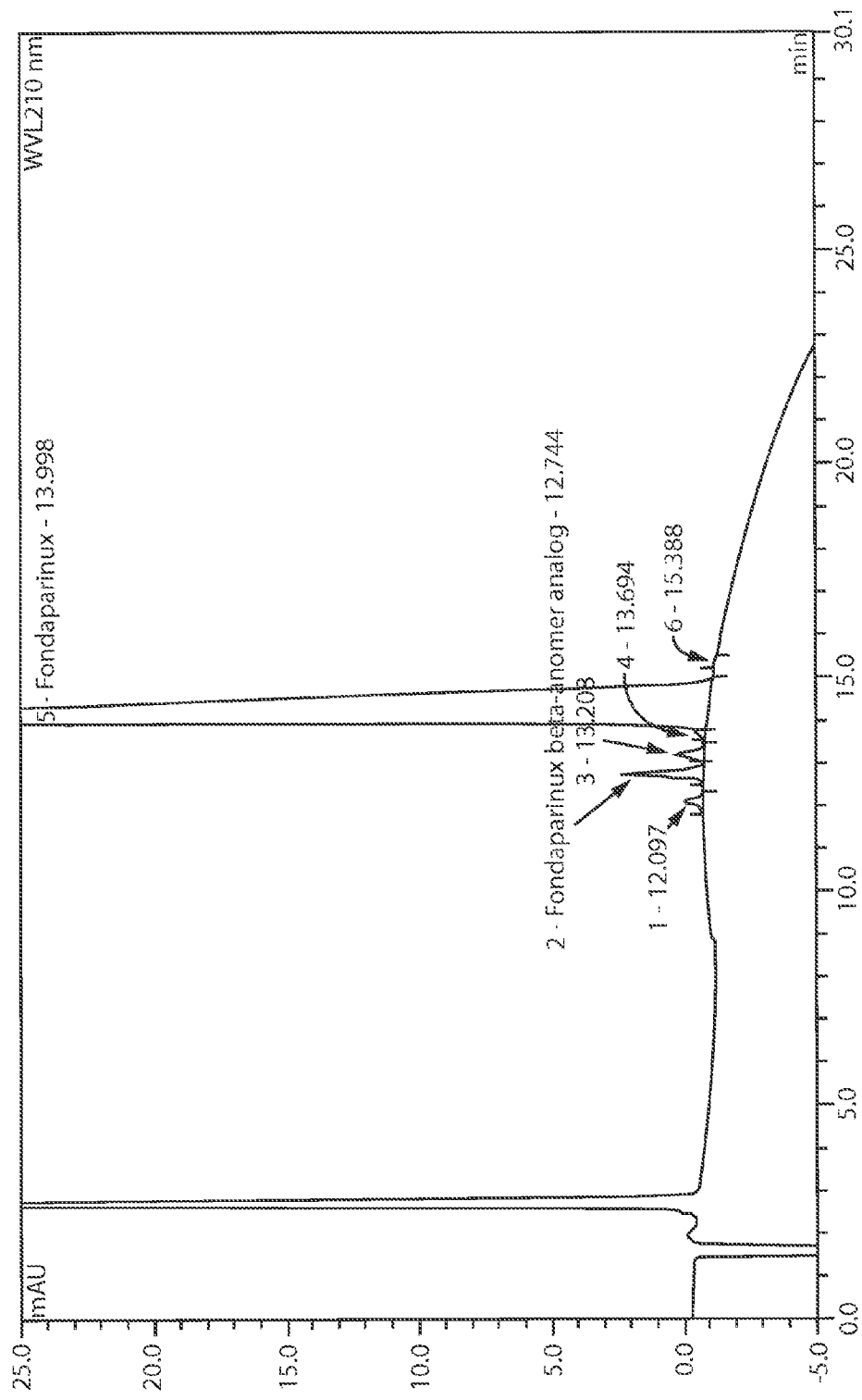
FIGS. 1A and 1B are High Performance Liquid Chromatography (HPLC) chromatograms of Fondaparinux sodium.

Applicants have developed novel synthetic strategies for the synthesis of Fondaparinux sodium and intermediates useful in the preparation of Fondaparinux sodium. The processes described herein allow for efficient scale-up, require fewer synthetic steps and proceed with higher yields of product than current processes. The processes described herein also afford a better purity profile due to reduced β-methyl glucoside contamination in the final product.

Thus, in one aspect, the present invention relates to a process for the preparation of Fondaparinux sodium in a novel and efficient manner providing the desired compound in good yield and in a manner that is scalable and reproducible on an industrial scale. The process of the present invention comprises a unique strategy that has been developed to obtain a synthetic process that is as convergent as possible.

Route 1, Route 2 and Route 3 shown below represent strategies reported in the literature for the synthesis of the pentasaccharide EDCBA. In contrast, one example of a novel process for the production of Fondaparinux sodium according to the present invention is also shown below.

Route 1

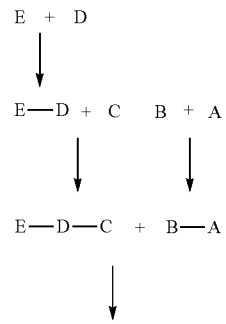

Route 2

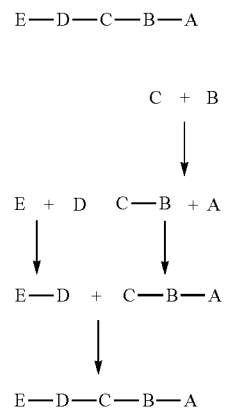

Route 3

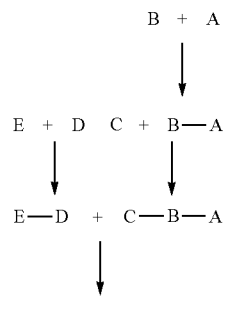

13

Present Invention
-continued

E + D—C    B + A
    ↓          ↓
E—D—C    +    B—A
              ↓
       E—D—C—B—A

The processes of the present invention, as outlined in the scheme above provide the desired pentasaccharide product (EDCBA) in fewer synthetic steps. Fewer synthetic steps increase the economic viability of the process. This is particularly important for producing tens of kilograms of Fondaparinux per year. For a review of process scale-up see, e.g., van Boeckel et al., *Angew. Chem. Intl. Ed.,* 32 1671-1818, 1993.

One aspect of a process of the present invention, Process 1, is summarized in the Scheme below:

14

Synthesis:

Following the strategy outlined for Process 1 in the scheme above, the following building blocks have been prepared for use in the preparation of Fondaparinux sodium.

Synthesis of the E Monosaccharide

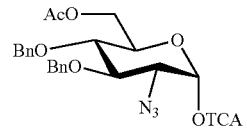

where Ac is acetyl, Bn is benzyl and TCA is trichloroacetimidate.

In one embodiment, Monomer E may be prepared by the process shown below. This method has been used in the processes of present invention on a multi-kilogram scale and has led to >95% α-glycosylation selectivity. See, e.g., Zhe et al., *Angew. Chem. Int. Ed.,* 48, 1900-1934, 2009. Monomer E is prepared in 8 steps starting from commercially available glucal triacetate. The introduction of the azide is achieved through a Cerny epoxide intermediate (M. Cerny et, al, *Adv.*

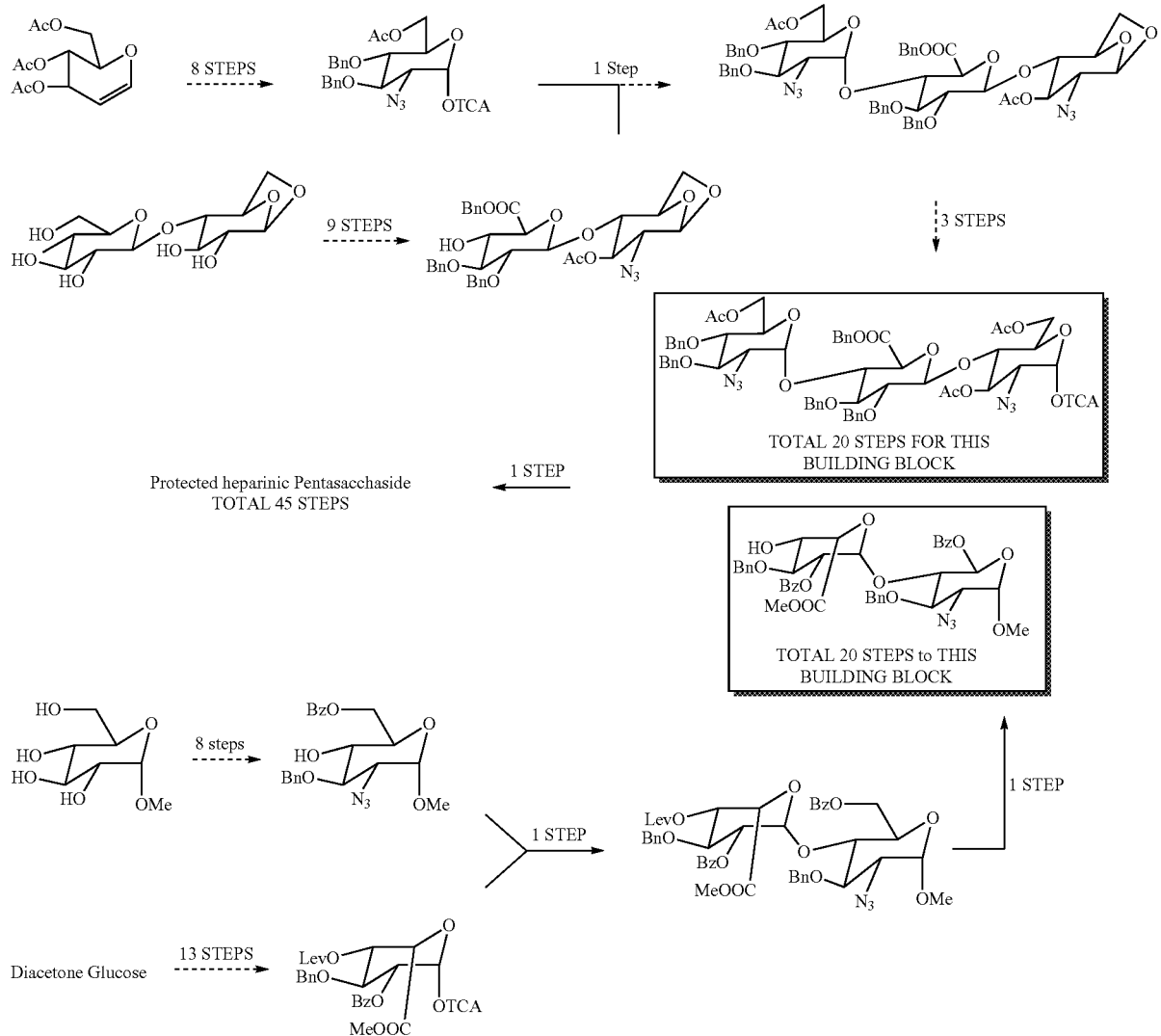

where Ac is acetyl, Bn is benzyl, Lev is levulinyl and TCA is trichloroacetimidate.

*Carbohydr. Chem. Biochem.,* 1977, 34, 23-127), as outlined in the scheme below.

SYNTHESIS OF MONOMER E

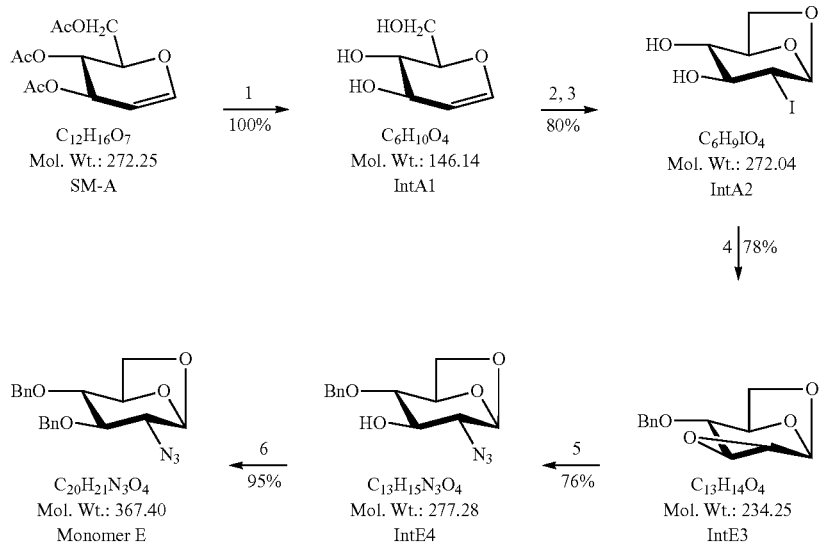

Reagents: 1. NaOMe, MeOH, RT, 2 hr, 50wx resin; 2. (Bu$_3$Sn)$_2$O (0.8 equiv), ACN, MS, reflux, 3 h; 3. I$_2$ (1.5 equiv), 5° C. to RT, 2 h; 4. NaH (2 equiv), DMF, BnBr (2.5 equiv), -20° C. to RT, 3 h; 5. NaN$_3$, DMF, 120° C., 12 h; 6. NaH, DMF, BnBr (2.5 equiv), 0° C. to RT, 3 h.

Synthesis of DC Building Block

Cellobiose is a natural disaccharide having a β-glycosidic linkage between sugars. Both disaccharides DC and BA in Fondaparinux sodium are connected through β-glycosidic bonds. In addition, the use of Cellobiose as a building block offers a more convergent synthesis and thus an appreciably reduced number of steps in the synthesis of Fondaparinux sodium.

Cellobiose has been reported for the synthesis of the DC and BA disaccharide building blocks. See, e.g., H. Kuzuhara et al., *Carbohydr. Res.*, 1988, 172, 73-64, 1988; H. Kuzuhara et al., *Tetrahedron Lett.*, 1986, 27, 611-614, 1986; H. Kuzuhara, *Carbhydr. Res.*, 1985, 141, 273-282, 1985 and M. Petitou et. al., *Biorg. Med. Chem. Let.*, 1991, 1 (2), 95-98. However, its use for the preparation of the BA disaccharide was not particularly successful, as the yield for the inversion of the C-5 center to convert Glucose to Idose, was disappointingly low (18%). Therefore, this approach was not practical. As depicted in the scheme below, the overall yield of DC disaccharide in the Kuzuhara synthesis was also low (only 3.5% over 12 steps). The Petitou modification (use of a selective tosylation of the 2-OH on the C residue) results in a slight increase in yield (11.58% over 12 steps). However, the yield is still very low.

Applicants have surprisingly found that novel chemical modifications allow for synthesis of the DC Building Block [DC disaccharide] in higher yields, involving fewer synthetic steps (e.g., 27.5% yield in 9 steps). This approach is outlined in the scheme below.

Cellobiose Building Block - Synthesis of DC Dimer

Ichikawa's Route

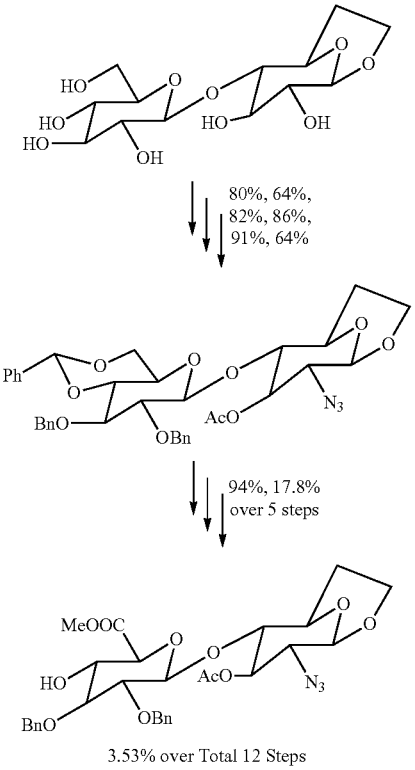

3.53% over Total 12 Steps

*Carbohydr. Res.*, 1985, 138, 55-64
*Carbohydr. Res.*, 1865, 141, 273-282

-continued

Choay's Route

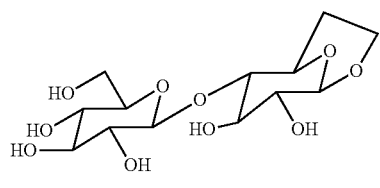

↓↓ 80%, 60%, 80%, 76%, 66%, 99%, 92%

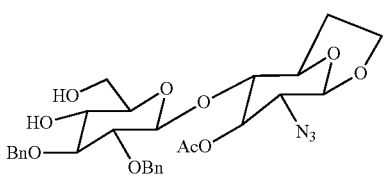

↓↓ 66% over 4 steps

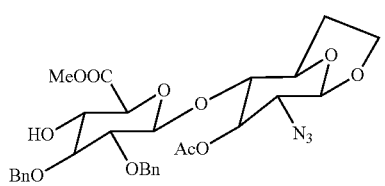

11.58% over Total 12 Steps

M. Petitou, et. al Bioorg. Med. Chem. Lett., 1991, 192), 95-98

Present Invention

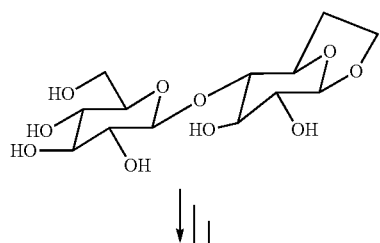

↓↓

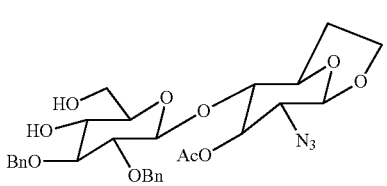

↓↓

-continued

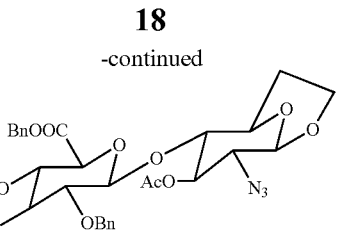

27.5% over Total 9 Steps

Anhydrocellobiose is commercially available; Synthesis: *Carbhyro. Res.*, 1982 (101), 148-151
Pentasaccharide Synthesis: *Tetrahedron Lett.*, 1986, 27(5), 611-614

Thus, another embodiment of the present invention is a process for preparing DC Building Block having the formula

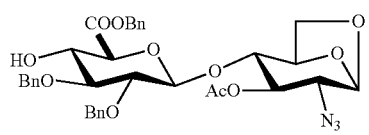

DCBB where the DC Building Block is prepared from 1,6-anhydrocellobiose having the structure

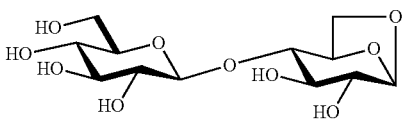

comprising at least four of the following steps:

(a) protecting 1,6-anhydrocellobiose to form CB1 having the structure

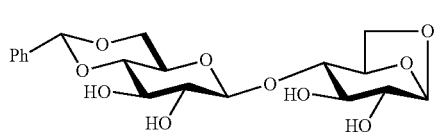

(b) tosylating CB1 to form CB2 having the structure

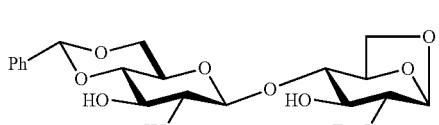

(c) reacting CB2 with base to form CB3 having the structure

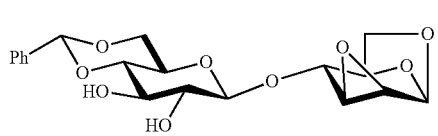

(d) protecting CB3 to form CB4 having the structure

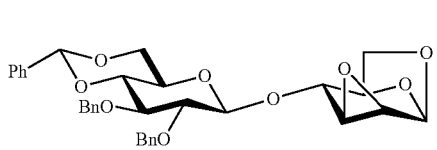
CB4

(e) reacting CB4 with azide to form CB5 having the structure

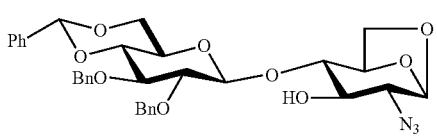
CB5

(f) acetylating CB5 to form CB6 having the structure

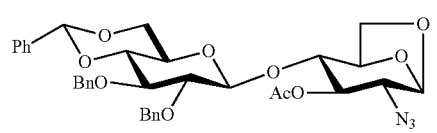
CB6

(g) deprotecting CB6 to form CB7 having the structure

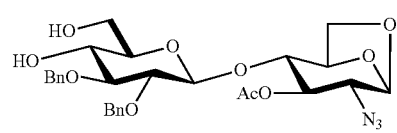
CB7

(h) oxidizing CB7 to form CB8 having the structure

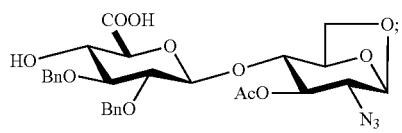
CB8 and (i) benzylating CB8 to form the DC dimer.

In certain embodiments, the process includes at least six steps from steps (a)-(i). In further embodiments, the process includes all of steps (a)-(i).

The process of the present invention for the synthesis of the DC dimer employs a milder oxidation procedure by using a TEMPO/NaOCl oxidation that eliminates the need for three steps of the Choay process: tritylation, levulynation and de-levulynation. This improved process of the present invention also provides improved yields of the DC dimer (up to 27.5%).

Synthesis of the Trisaccharide Building Block EDC

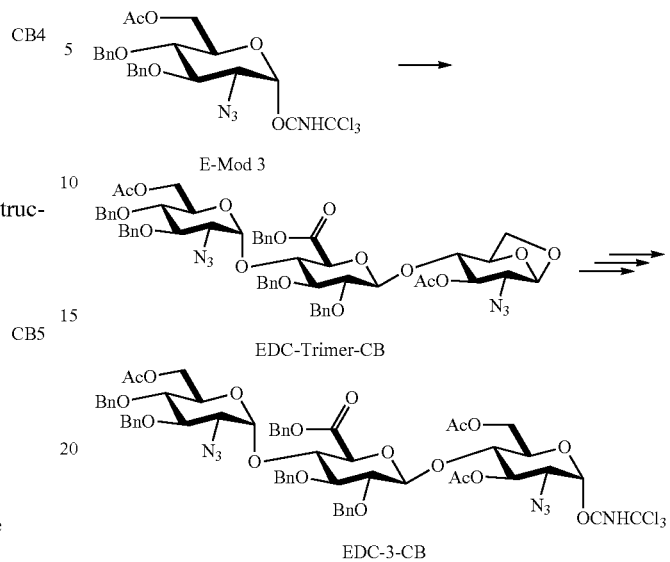

The synthesis of the EDC fragment [EDC-3-CB] is achieved in 8 steps and in ~40% overall yield. See U.S. Provisional Application Ser. No. 61/230,557, filed Jul. 31, 2009 and U.S. patent application Ser. No. 12/847,719, filed Jul. 30, 2010, which are hereby incorporated by reference in their entireties. The desired α-coupling stereochemistry of the glycosyl bond between the E monomer and the DC disaccharide building block is obtained via Schmidt's acetimidate chemistry, which affords the trisaccharide. No β-isomer could be detected by ¹H NMR on the isolated product. The anhydro trisaccharide may be converted to the corresponding trichloroacetimidate acceptor using the methods described herein or via standard techniques known in the art (J. Choay et al. *Bioorg. Med. Chem. Lett.,* 1, 95-98, 1991).

Thus another embodiment of the present invention is a process for preparing EDC trimer having the formula

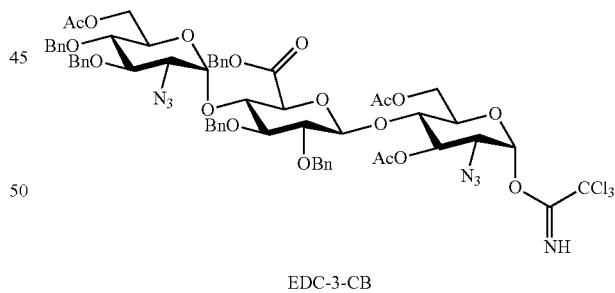
EDC-3-CB wherein the EDC trimer is prepared by a process (e.g., a Schmidt glycosylation) comprising the steps:

(a) coupling an E monomer having the structure

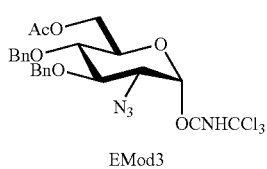
EMod3 to a DC Building Block having the structure

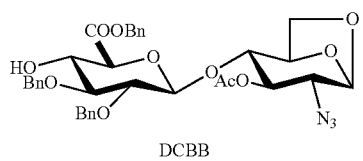

DCBB to obtain an EDC precursor having the structure

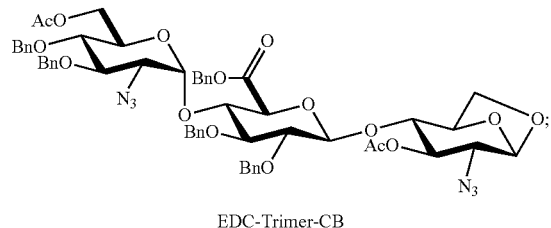

EDC-Trimer-CB and (b) converting the EDC precursor to the EDC trimer.

In another embodiment, the present invention relates to a process that further comprises converting the EDC trimer to Fondaparinux sodium.

Synthesis of Disaccharide Building Block BA

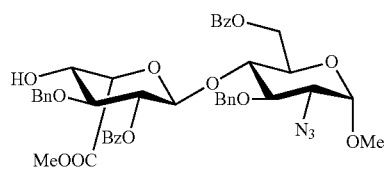

(j) Synthesis of Building Block A (AMod5)

An efficient general strategy for the synthesis of the EDCBA pentasaccharide using the E+DC+BA connection process requires an efficient process for the synthesis of both the B and A monosaccharide building blocks. A number of scientific publications describe methods for the synthesis of the α-Methyl glucosamine glucoside derivative Monosaccharide A. See, e.g., S. Y. Luo et al. *Tetrahedron Lett.*, 43, 4889-4892, 2002; M. Petitou et al. *Carbohydr Res.*, 281, 253-276, 1996; T. Suami et al., *Bull Chem. Soc. Jpn.*, 55, 1574-1578, 1982; and M. J. Hadd et al., *Carbohydr. Res.*, 1999, 320, 61-69, 1999.

Building Block A - Synthesis

Alchemia's Route

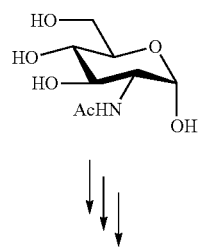

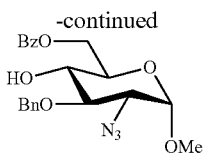

safety concerns;
not scalable
24.4% over 13 Steps

AU2008200616 07 Feb 2008; P. B. Alper *et. al. Tet. Lett.* 1996, 37 (34), 6029-6032

Organon's Route

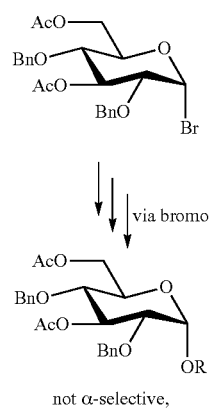

not α-selective,
gave mixtures

N. M. Spijker, *et. al Tetrahedron.*, 1992, 48(30), 6297-6316

Sanofi's route

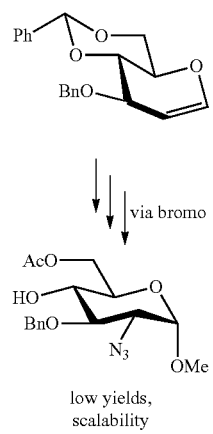

low yields,
scalability

C. Tabeur *et. al, Carbohyd. Res.*, 1996, 281, 253-276; R. U. Lemieux, *et. al Can. J. Chem..*, 1979, 57, 1244-1251

Present Invention

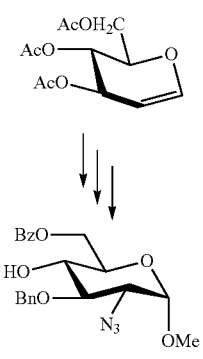

19.6% over 10 Steps

M. J. Hadd *et. al, Carbohyd. Res.*, 1999, 320, 61-69; S. Arndt, *et. al Org. Lett..*, 2003, 5(22), 4179-4182

However, a serious drawback in all of the known synthetic approaches to Fondaparinux is contamination by some percentage of the undesired β-methyl glucoside isomer [Compound P1],

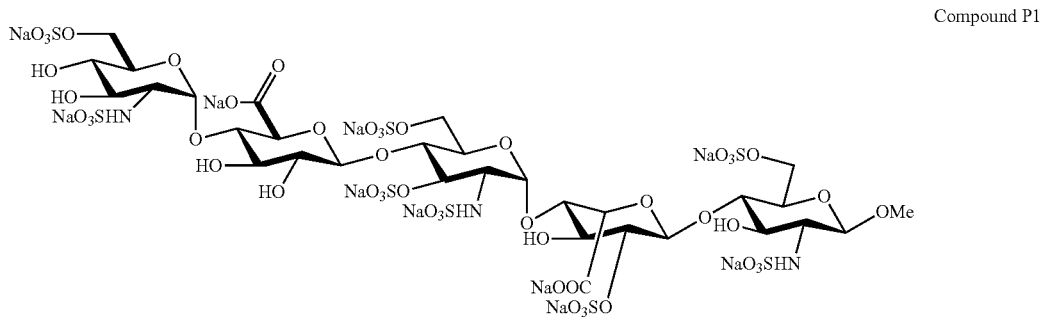

Compound P1

Figure 1B:
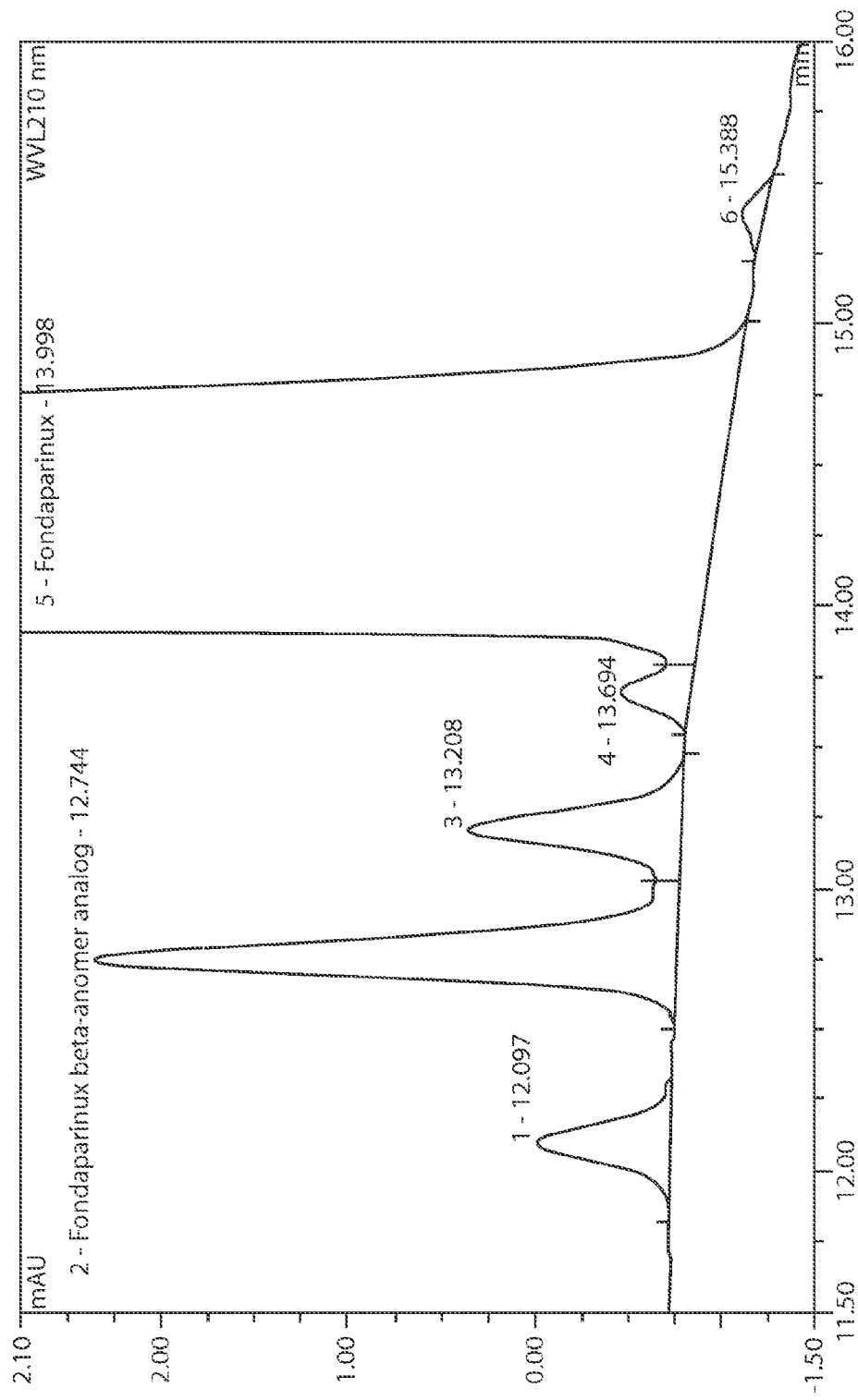

FIGS. 1A and 1B depict the HPLC chromatogram for Fondaparinux sodium, and show the proximity of the peak for the β-anomer (Compound P1) to the desired α-anomeric product (Fondaparinux sodium).

Contamination by even a small amount of Compound P1 [β-anomer] is problematic for the overall synthesis of Fondaparinux, as separation of this undesired contaminant from the desired α-anomer is required. Efforts to effect the separation of the unwanted β-anomer cause a substantial loss of product as evidenced by low yields. Applicants have developed two approaches that overcome this problem.

In the first approach, the present invention employs highly purified methyl-α-D-glucopyranoside (Aldrich, min. 99% purity) as a starting material for the synthesis of Monomer A. This process eliminates the possibility of the presence of any β-anomer in the final product. Thus, methyl-α-D-glucopyranoside is converted to the desired building block according to the scheme depicted below. During the further synthetic manipulations toward preparing Fondaparinux from Building Block A there are no synthetic operations that can epimerize the anomeric center in this monomer. This strategy affords α-methyl-2-azido-3-benzyl-6-benzoyl-D-glucoside free from its β-anomer.

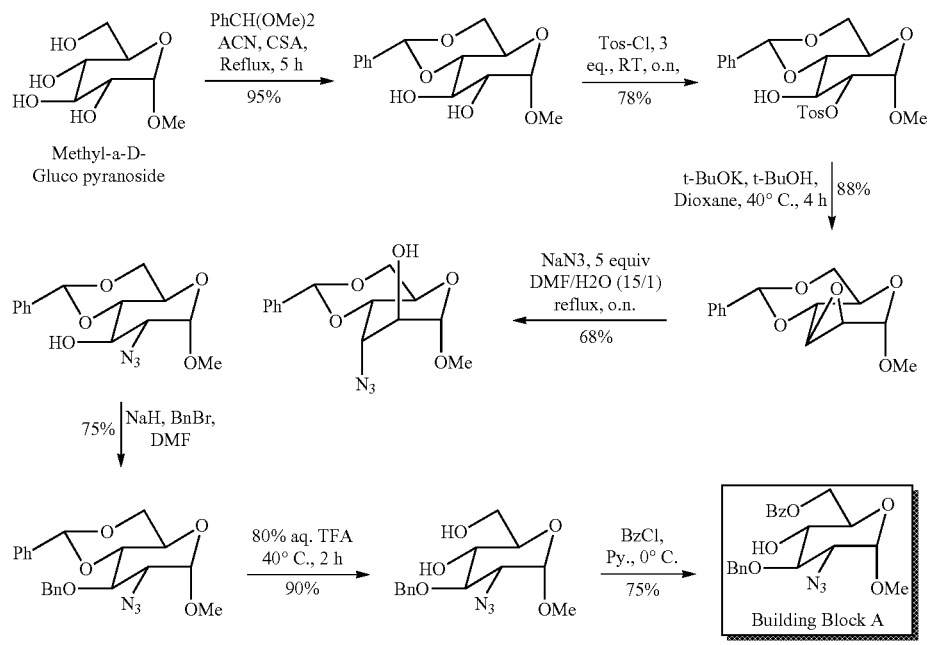

In a second approach, the present invention is directed to a process for preparing Building Block A that involves the steps shown in the following scheme. Building Block A [also referred to as AMod5] may be prepared from triacetyl-D-Glucal [also referred to as SM-A]. The triacetyl-D-glucal is hydrolyzed to form D-Glucal [also referred to as IntA1]. The oxidative-1,6-iodocyclization of IntA1 gives IntA2. Epoxidation of the compound IntA2 to form compound [the Cerny epoxide] IntA2a [not isolated] which is p-methoxybenzylated to form compound IntA3. The azide assisted ring opening of the Cerny epoxide IntA3 affords the azide derivative IntA4. Benzylating the C-3 hydroxyl moiety on IntA4 gives Monomer A2 [also referred to as IntA5]. The Monomer A2 is α-methylglycosylated to form compound AMod3, which upon deacetylation gives the compound AMod4. The C-5 hydroxyl moiety on AMod4 is selectively benzoylated to give the compound AMod5 [Building Block A] which is recrystallized to give exclusively the α-anomer of AMod5. This is shown in the scheme below.

SCHEME 1 - Synthesis of Monomer A-2 & AMod5 [Building Block A]

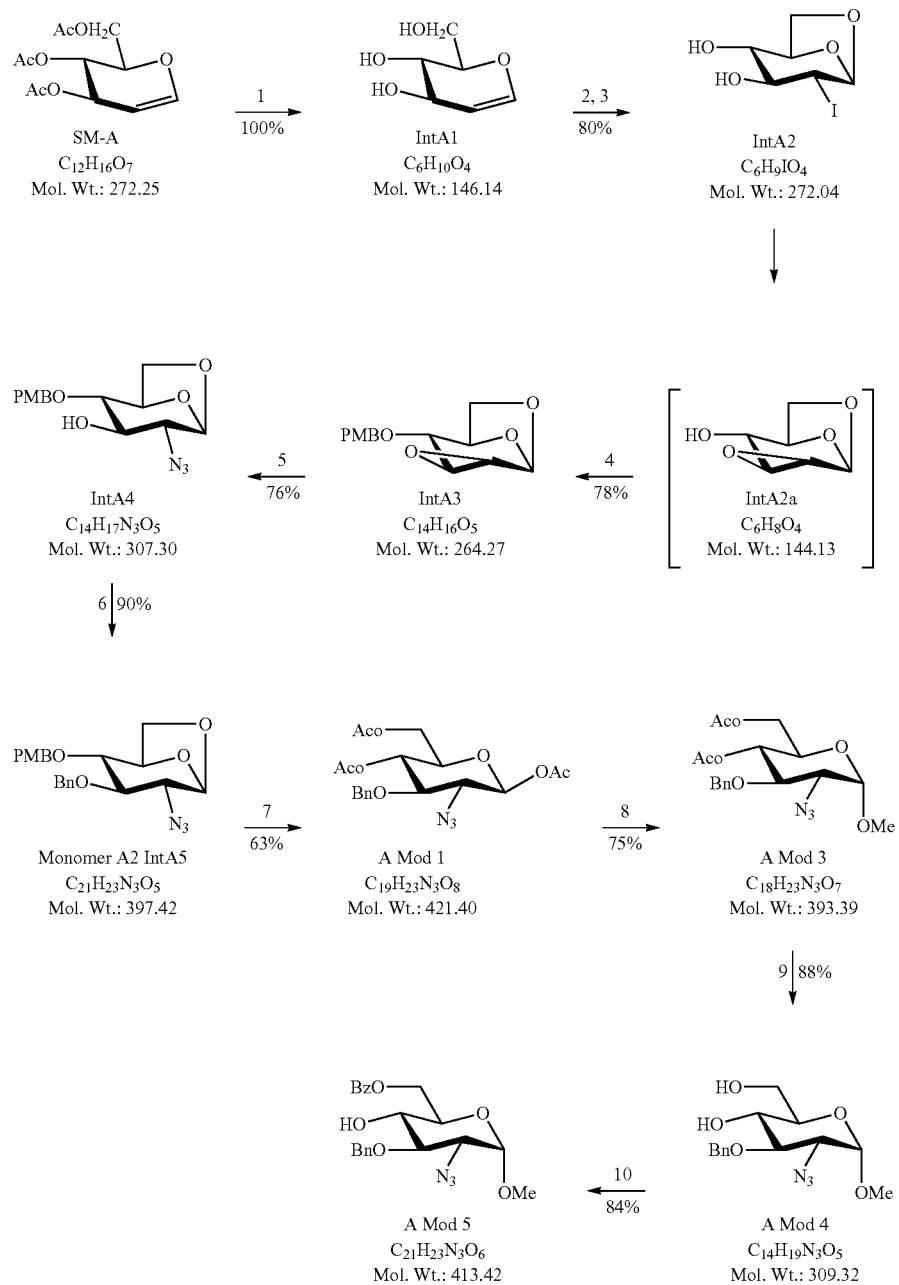

Reagents: 1. NaOMe, MeOH, RT, 2 hr, 50wx resin; 2. (Bu$_3$Sn)$_2$ (0.8 equiv), ACN, MS, reflux, 3 h; 3. I$_2$ (1.5 equiv), 5° C. to RT, 2 h; 4. NaH (2 equiv), DMF, p-MeOC$_6$H$_4$CH$_2$Br (PMB-Br, 2.5 equiv), -20° C. to RT, 2 h; 5. NaN$_3$, DMF, 120° C., 12 h; 6. NaH, DMF, BnBr. 0° C. to RT. 3 h.; 7. BF$_3$·Et$_2$O, Ac$_2$O, DCM, -20° C. to RT, 3 h; 8. (a) TMS-I, TBAI, RT, 2 h; (b) DIPEA, MeOH, 16 h, RT; 9. NaOMe, Dowex 50WX8-100 resin H+ form, RT, 3 h; 10. Pyridine, Bz-Cl, -40° C. to -10° C., 2 h;

The process described above allows for complete synthesis of Building block A in 10 steps and approximately 20% overall yield (M. J. Hadd et, al, *Carbohyd. Res.*, 1999, 320, 61-69; S. Arndt, et. al Org. Lett., 2003, 5 (22), 4179-4182). This process has the fewest number of steps and to the best of our knowledge, is the most efficient and safe method of producing multi kilogram quantities of 2-azido-1-alpha-methyl-glucopyanoside derivatives that avoids Lemiuex's azidonitration of glucals that offer a poor α/β selectivity (see, e.g., R. U. Lemieux, et. Al, *Can. J. Chem.*, 1979, 57, 1244-1251; C. Tabeur et. al, *Carbohyd. Res.*, 1996, 281, 253-276, U.S. Pat. No. 4,818,816; N. M. Spijker, et. Al, *Tetrahedron*. 1992, 48(30), 6297-6316) and the hazardous metal-catalyzed diazo transfer for azide incorporation at the 2-position that poses serious safety concerns at multi kilogram scale manufacture (see, e.g., P. B. Alper el. al. *Tet. Lett.* 1996, 37 (34), 6029-6032; Australian Patent No. AU 2008 200616).

The process disclosed herein produces Building Block A of highest purity (≥99%) that has been reported to date. In one embodiment, the process involves a crystallization procedure that results in the enhanced purity of the α-anomer of AMod5 [Building Block A]. In certain embodiments, AMod5 [Building Block A] is recrystallized from a solvent selected from C5 to C7 hydrocarbons. In one embodiment the solvent is heptane. The crystallization of AMod5 is carried out by dissolving AMod5 in a solvent (such as a C5-C7 hydrocarbon solvent) at temperatures between about 50 and about 80° C. In one embodiment, the crystallization of AMod5 is carried out by dissolving AMod5 in heptane at temperatures between about 50 and about 60° C. In certain embodiments, the solution of AMod5 is then cooled to room temperature and allowed to stand (e.g., for about 16 hours) at this temperature.

In additional embodiments, Building Block A is prepared in greater than about 95%, greater than about 96%, greater than about 97.5%, greater than about 98%, greater than about 99%, greater than about 99.5%, or greater than about 99.9% α-anomer form.

In additional embodiments, the Building Block A prepared contains less than about 5%, less than about 4%, less than about 2.5%, less than about 2%, less than about 1%, less than about 0.5%, less than about 0.1% or less than about 0.05% β-anomer form.

In a further embodiment, the present invention relates to a method of purifying a monosaccharide of the formula

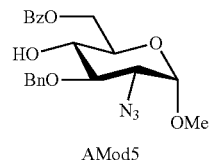

AMod5 by crystallizing the monosaccharide from an organic solvent selected from C5 to C7 hydrocarbons, such as heptane.

In yet a further embodiment, the present invention relates to a method of preparing a monosaccharide AMod3

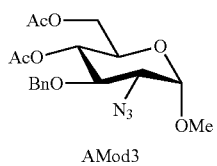

AMod3 comprising α-methylglycosylating the compound Monomer A2 [also referred to as IntA5]

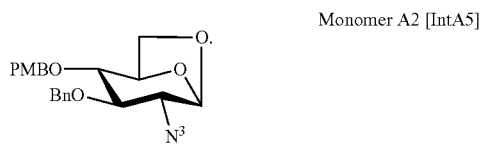

Monomer A2 [IntA5]

(ii) Synthesis of the Building Block B

Another challenging problem in the synthesis of Fondaparinux Sodium is an accessible source of the idose sugar. This problem arises because no natural source for this carbohydrate is known. Furthermore, commercially available starting materials are cost prohibitive for large-scale industrial applications.

In one embodiment of the present invention, Building Block B [also referred to as BMod6] may be prepared according as shown in the scheme below.

Scheme 2 - Synthesis of Monomer B-1 and BMod6 [Building Block B]

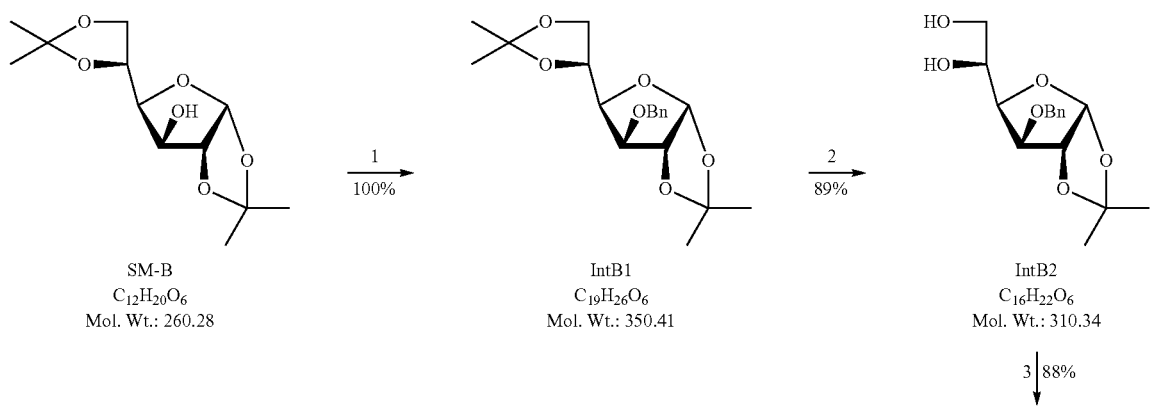

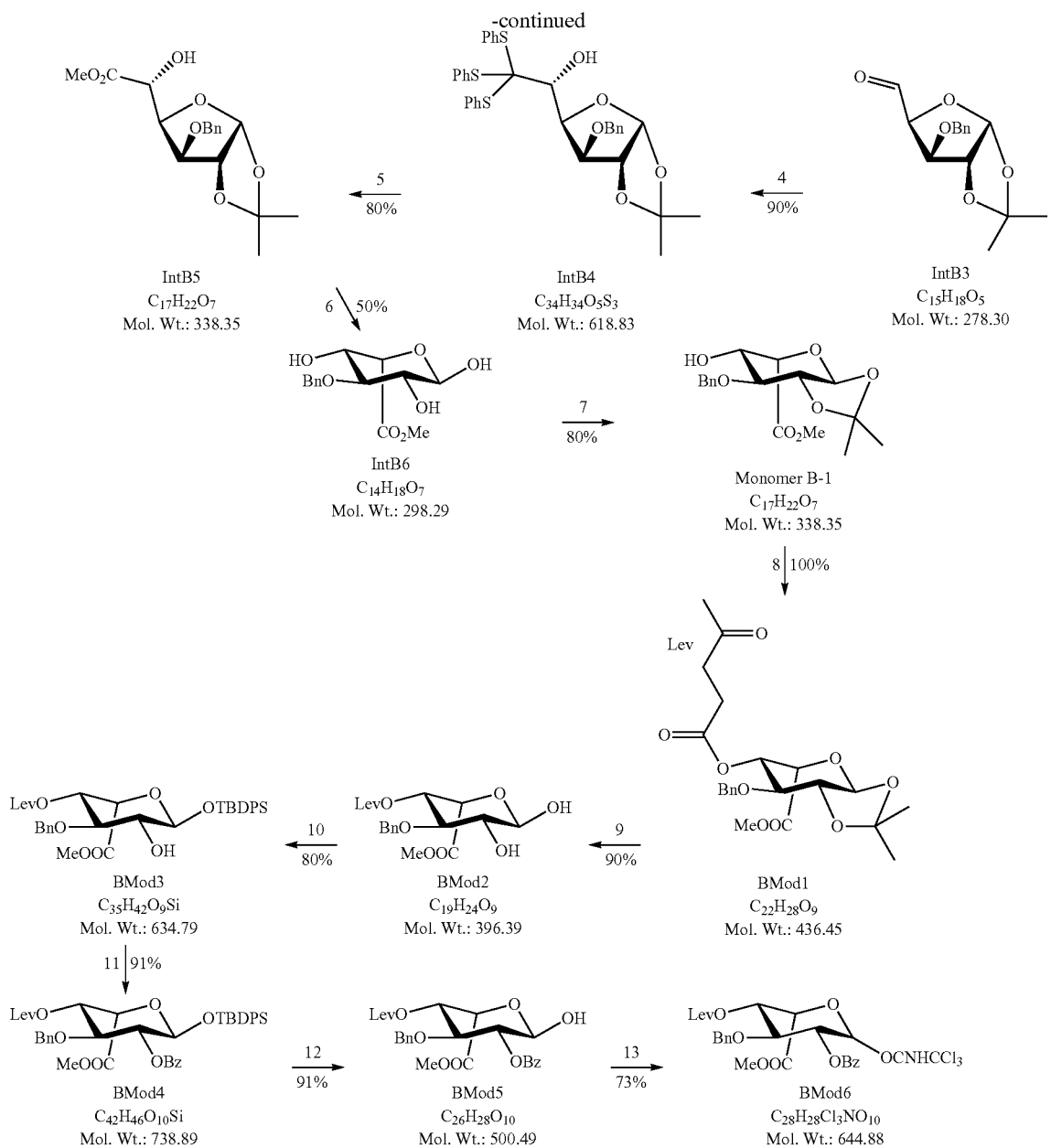

Reagents: 1. NaH, BnBr, THF, DMF, 0° to 65° C., 3 h; 2. 66% Acetic Acid/H₂O, 40° C., 16 h; 3. NaIO₄, (Bu)₄NBr, DCM, H₂O, Dark, 3 h; 4. (PhS)₃CH, n-BuLi, THF, -78° C., 3 h; 5. CuCl₂/CuO, MeOH, H₂O, 3 h; 6. 90% TFA/H₂O, DCM, RT, 2 h; 7. DMF, CSA 2-methoxypropene, 0° to RT, 16 hrs; MeOH, TEA. 8. Lev₂O, DIPEA, RT, 16 h; 9. 90% TFA, RT, 4 h; 10. Imidazole, TBDPSi-Cl, RT, 3 h; 11. Pyridine, BzCl, RT, 3 h; 12. TBAF, RT, 3 h: 13. TCA, DBU, RT, 2 h;

Also see, e.g., Bonnaffe et al., *Tetrahedron Lett.*, 41, 307-311, 2000; Bonnaffe et al., *Carbohydr. Res.*, 2003, 338, 681-686, 2003; and Seeberger et al., *J. Org. Chem.*, 2003, 68, 7559-7561, 2003.

The method of the present invention uses t-butyldiphenylsilyl [TBDPS] chloride in place of t-butyldimethylsilyl [TBDMS] chloride because of the ease of migration of the TBDMS protecting group to the 2-position during the silylation step. The use of TBDPS results in an increase in yield of BMod6, [Building Block B] of ~5%. The overall yield of BMod6 [Building Block B] from diacetone glucose [SM-B] is, e.g., ~11%.

(iii) Synthesis of the BA Dimer Fragment

In another embodiment of the processes described herein, monomers A and B, prepared as described above, may be linked to form the BA dimer, with complete β-stereospecificity at the glycosidic linkage. For example, BA dimer may be prepared with complete β-stereospecificity at the glycosidic linkage in ~72% yield on a multi kilogram scale. Removal of the Lev group (82%) by standard methods provides the BA dimer in a form ready for coupling with the EDC trimer building block.

Fully Protected Pentasaccharide EDCBA

In another embodiment of the processes described herein, coupling of the EDC trimer with the BA disaccharide donor produces the desired α-linked pentasaccharide (EDCBA, also referred to as Fully Protected Pentasaccharide (FPP)), as shown in the scheme below.

31                                                                 32

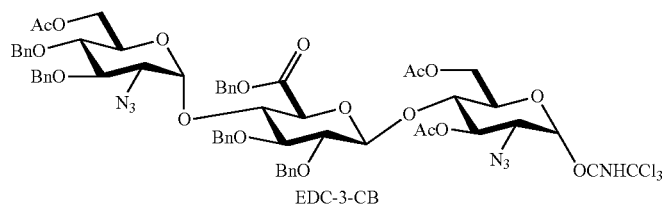
EDC-3-CB

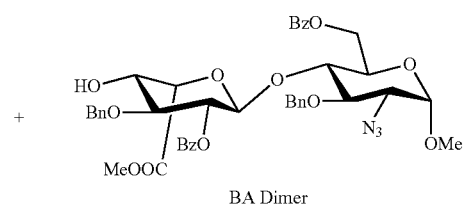
BA Dimer

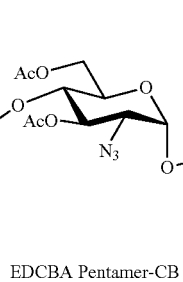
71%

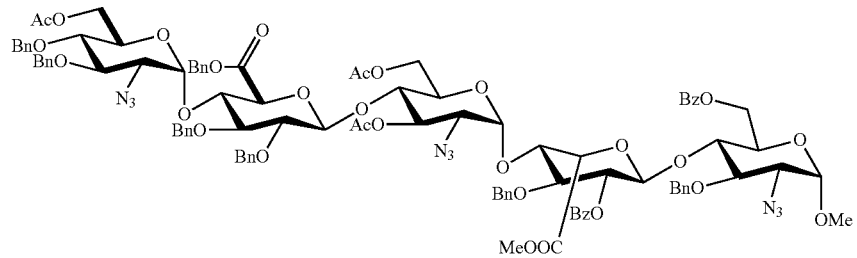
EDCBA Pentamer-CB

Thus, a further embodiment of the present invention is a process for the preparation of a fully protected heparinic pentasaccharide precursor to Fondaparinux sodium having the structure

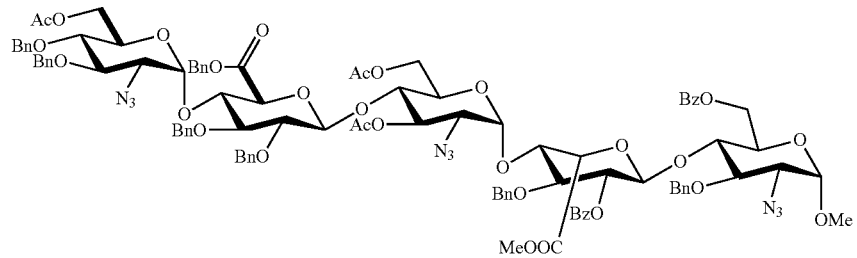

comprising the step of coupling a EDC trimer having the structure

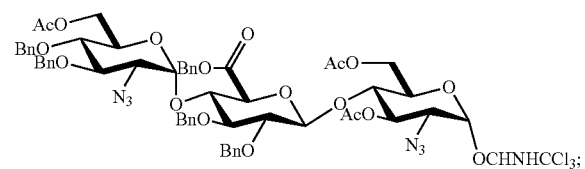

with a BA dimer having the structure

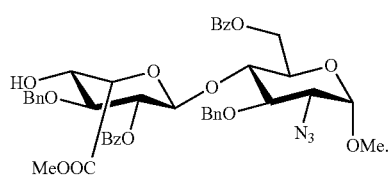

In another embodiment, the present invention relates to a process that further comprises converting the fully protected heparinic pentasaccharide precursor to Fondaparinux sodium.

Synthetic Summary

By employing the processes of the present invention, as described herein, the fully protected pentasaccharide precursor (EDCBA) may be prepared in 44 steps, which may then be converted to Fondaparinux sodium in four steps (total of 48 overall steps). The processes described herein allow for the synthesis of Fondaparinux sodium in fewer synthetic steps than those previously described. The processes described herein also afford a better purity profile due to reduced β-methyl glucoside contamination in the final product.

Compounds with Reduced Amounts of β-Anomer

In a further aspect, the present invention relates to a fully protected heparinic pentasaccharide precursor to Fondaparinux sodium having the structure

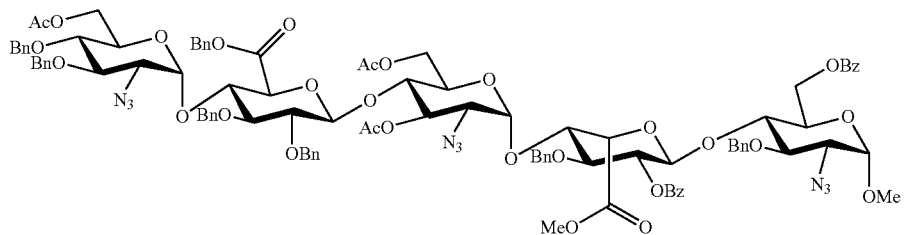

in which the amount of the corresponding β-methyl glycoside is less than about 0.5%, such as less than about 0.4%, less than about 0.3%, less than about 0.2%, less than about 0.1%, less than about 0.05%, less than about 0.01%, less than about 0.005%, or less than about 0.001% In one embodiment, the fully protected heparinic pentasaccharide precursor is substantially free of the corresponding β-methyl glycoside.

The term "substantially free of" as used herein when referring to an impurity (such as a β-methyl glycoside), means that a desired compound contains less than about 0.1%, such as less than about 0.05%, less than about 0.01%, less than about 0.005%, less than about 0.001% or less than about 0.0005% by weight of the impurity.

In a further aspect, the present invention relates to Building Block A [also referred to as AMod5, Monosaccharide A] having the structure

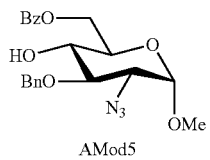

AMod5 in which the amount of the corresponding β-methyl anomer is less than about 0.5%, such as less than about 0.4%, less than about 0.3%, less than about 0.2%, less than about 0.1%, less than about 0.05%, less than about 0.01%, less than about 0.005%, or less than about 0.001% In one embodiment, Building Block A [AMod5, Monosaccharide A] is substantially free of the corresponding β-methyl anomer.

In a further aspect, the present invention relates to Fondaparinux, or a salt thereof (e.g., Fondaparinux sodium) and compositions containing the same, in which the amount of Compound P1 (beta-anomer of Fondaparinux sodium) is reduced.

In certain embodiments, Compound P1 is present in an amount of less than about 0.5%, such as less than about 0.4%, less than about 0.3%, less than about 0.2%, less than about 0.1%, less than about 0.05%, less than about 0.01%, less than about 0.005%, or less than about 0.001% based on the total weight of Fondaparinux or composition. In one embodiment, the Fondaparinux sodium, or a composition containing Fondaparinux sodium, is substantially free of Compound P1.

Any of the aforementioned forms of Fondaparinux (or a salt thereof) or compositions containing Fondaparinux (or a salt thereof) may be administered (e.g., 2.5 mg, 5 mg, 7.5 mg, 10 mg, solution for injection) for the prophylaxis of deep vein thrombosis (DVT) which may lead to pulmonary embolism (PE) in patients undergoing (i) hip fracture surgery (including extended prophylaxis), (ii) hip replacement surgery, (iii) knee replacement surgery and (iv) abdominal surgery (who are at risk for thromboembolic complications). The forms and compositions described herein may also be administered in conjunction with wafarin sodium for the treatment of acute DVT and PE.

Definitions

Examples of alkyl groups having one to six carbon atoms, are methyl, ethyl, propyl, butyl, pentyl, hexyl, and all isomeric forms and straight and branched thereof.

The term "acyl" unless otherwise defined refers to the chemical group —C(O)R. R can be, for example, aryl (e.g., phenyl) or alkyl (e.g., $C_1$-$C_6$ alkyl).

The term "aryl" refers to an aromatic group having 6 to 14 carbon atoms such as, for example, phenyl, naphthyl, tetrahydronapthyl, indanyl, and biphenyl. The term "heteroaryl" refers to an aromatic group having 5 to 14 atoms where at least one of the carbons has been replaced by N, O or S. Suitable examples include, for example, pyridyl, quinolinyl, dihydroquinolinyl, isoquinolinyl, quinazolinyl, dihydroquinazolyl, and tetrahydroquinazolyl.

It will be apparent to those skilled in the art that sensitive functional groups may need to be protected and deprotected during synthesis of a compound of the invention. This may be achieved by conventional methods, for example as described in "Protective Groups in Organic Synthesis" by Greene and Wuts, John Wiley & Sons Inc (1999), and references therein which can be added or removed using the procedures set forth therein. Examples of protected hydroxyl groups (i.e., hydroxyl protecting groups) include silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to, methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups (i.e., amino protecting groups) include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and the like.

A protecting group that can be removed by hydrogenation is, by way of example, benzyl or a substituted benzyl group, for example benzyl ethers, benzylidene acetals. While the benzyl group itself is a commonly used protecting group that can be removed by hydrogenation, one example of a substituted benzyl protecting group is p-methoxy benzyl.

Throughout the description and claims of this specification the word "comprise" and other forms of the word, such as "comprising" and "comprises," means including but not limited to, and is not intended to exclude, for example, other additives, components, integers, or steps.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

The following abbreviations are used: Ac is acetyl; ACN is acetonitrile; MS is molecular sieves: DMF is dimethyl formamide; PMB is p-methoxybenzyl; Bn is benzyl; DCM is dichloromethane; THF is tetrahydrofuran; TFA is trifluoro acetic acid; CSA is camphor sulfonic acid; TEA is triethylamine; MeOH is methanol; DMAP is dimethylaminopyridine; RT is room temperature; CAN is ceric ammonium nitrate; $Ac_2O$ is acetic anhydride; HBr is hydrogen bromide; TEMPO is tetramethylpiperidine-N-oxide; TBACl is tetrabutyl ammonium chloride; EtOAc is ethyl acetate; HOBT is hydroxybenzotriazole; DCC is dicyclohexylcarbodiimide; Lev is levunlinyl; TBDPS is tertiary-butyl diphenylsilyl; TBDMS is tertiary-butyl dimethylsilyl; TCA is trichloroacetonitrile; O-TCA is O-trichloroacetimidate; $Lev_2O$ is levulinic anhydride; DIPEA is diisopropylethylamine; Bz is benzoyl; TBAF is tetrabutylammonium fluoride; DBU is diazabicycloundecane; $BF_3 \cdot Et_2O$ is boron trifluoride etherate; TMSI is trimethylsilyl iodide; TBAI is tetrabutylammonium iodide; TES-Tf is triethylsilyl trifluoromethanesulfonate (triethylsilyl triflate); DHP is dihydropyran; PTS is p-toluenesulfonic acid.

Preparation of the certain monomers used in the processes described herein are either known in the art or can be prepared using the methods described herein.

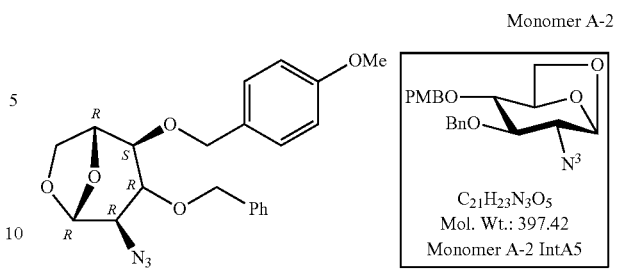

The synthesis of Monomer A-2 (CAS Registry Number 134221-42-4) has been described in the following references: Arndt et al., *Organic Letters*, 5(22), 4179-4182, 2003; Sakairi et al., *Bulletin of the Chemical Society of Japan*, 67(6), 1756-8, 1994; and Sakairi et al., *Journal of the Chemical Society, Chemical Communications*, (5), 289-90, 1991, and the references cited therein, which are hereby incorporated by reference in their entireties.

The Monomer A2 may also be obtained in 6 synthetic steps from tri-O-acetyl D-glucal. The triacetate, SM-A was deacetylated with sodium methoxide in methanol to give the intermediate, IntA1. The primary hydroxyl group was converted to the anhydro derivative with tributyltin oxide and then iodinated in a two step one pot procedure to give the iodo derivative IntA2. The iodo derivative was converted to the bisanhydro [also known as epoxide] derivative and the C4-hydroxyl was protected as its PMB ether IntA3 by treatment with sodium hydride and p-methoxybenzyl bromide. The epoxide of IntA3 was ring opened with sodium azide to give the C2-azido derivative IntA4. The free hydroxyl at the C3 position was then alkylated with benzyl bromide to form the bisether compound Monomer A2.

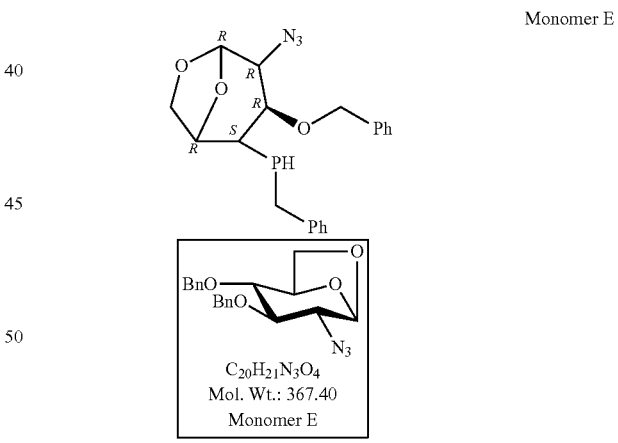

Monomer E (CAS Registry Number 55682-48-9) can be synthesized using the methods described in the following literature references: Hawley et al., *European Journal of Organic Chemistry*, (12), 1925-1936, 2002; Dondoni et al., *Journal of Organic Chemistry*, 67(13), 4475-4486, 2002; Van der Klein et al., *Tetrahedron*, 48(22), 4649-58, 1992; Hori et al., *Journal of Organic Chemistry*, 54(6), 1346-53, 1989; Sakairi et al., *Bulletin of the Chemical Society of Japan*, 67(6), 1756-8, 1994; Tailler et al., *Journal of the Chemical Society, Perkin Transactions 1: Organic and Bio-Organic Chemistry*, (23), 3163-4, (1972-1999) (1992); Paulsen et al., *Chemische Berichte*, 111(6), 2334-47, 1978; Dasgupta et al., Synthesis, (8), 626-8, 1988; Paulsen et al., *Angewandte Chemie*, 87(15), 547-8, 1975; and references cited therein, which are hereby incorporated by reference in their entireties.

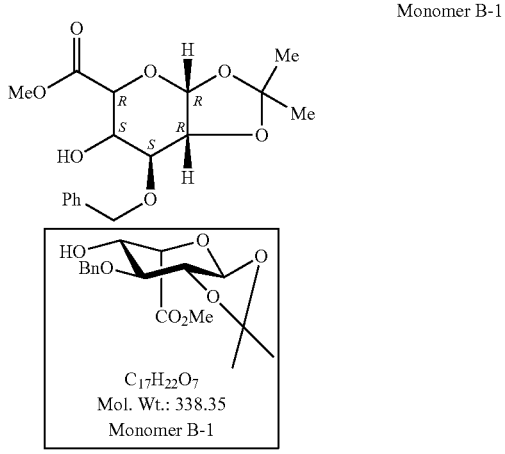

Mononer B-1 (CAS Registry Number 444118-44-9) can be synthesized using the methods described in the following literature references: Lohman et al., *Journal of Organic Chemistry*, 68(19), 7559-7561, 2003; Orgueira et al., *Chemistry—A European Journal*, 9(1), 140-169, 2003; Manabe et al., *Journal of the American Chemical Society*. 128(33), 10666-10667, 2006; Orgueira et al., *Angewandte Chemie, International Edition*, 41(12), 2128-2131, 2002; and references cited therein, which are hereby incorporated by reference in their entireties.

The Monomer B1 may also be obtained in 7 synthetic steps from diacetone glucose [SM-B]. The C3-hydroxyl moiety in diacetone glucose (SM-B) was protected as the benzyl ether by reaction with benzyl bromide to give IntB1. The C5-C6 isopropylidene moiety was selectively deprotected with aqueous acetic acid to give the diol intermediate IntB2. The C5-C6 diol was then oxidative cleaved with sodium periodate to give the aldehyde derivative IntB3. The aldehyde InB3 was converted to the orthoester derivative IntB4 with tris[phenylthio]methane and butyl lithium. IntB4 was then converted to the iodofuranuronate derivative IntB5 in the presence of copper (II) chloride and copper (II) oxide. The C1-C2 isopropylidene moiety was deprotected with aqueous trifluoroacetic acid to give the glucopyranuronate diol IntB6. The C1-C2 diol IntB6 was then protected as its isopropylidene derivative to give Monomer B1.

Synthesis of the DC Building Block (DC Dimer) of EDCBA (which is Equivalent to the EF Dimer of the DEFGH Pentasaccharide The DC Building Block [DCBB] was prepared in 9 synthetic steps from AnhydroCellobiose using the following procedure: The C4 and C6 alcohol moieties of the 'D' ring of anhydrocellobiose [ACB] were protected as the benzylidene derivative [CB1] using benzaldehyde dimethylacetal in acetonitrile and camphorsulfonic acid as catalyst. The C2-hydroxyl on the 'C' ring of the disaccharide CB1 was reacted with p-toluenesulfonylchloride in pyridine with a catalytic amount of DMAP to give the tosylated derivative CB2. The tosyl derivative CB2 was reacted with potassium t-butoxide in tert-butanol and dichloromethane to give the epoxide intermediate CB3. The C-2 and C-3 hydroxyl moieties on the 'D' ring were protected as the benzyl ethers by the reaction with benzyl bromide in DMF and Sodium Hydride as the base, to give the dibenzyl intermediate CB4. The epoxide ring of CB4 was opened with sodium azide in water and DMF to give the azido derivative, CB5. The C3-hydroxyl on the 'C' ring of the disaccharide CB5 was reacted with acetic anhydride in dichlormethane and a catalytic amount of DMAP to give the acetate derivative CB6. The benzylidene moiety of CB6 was deprotected using 8% TFA in tetrahydrofuran to give the diol intermediate CB7. The C6-hydroxyl of the 'D' ring in CB7 was oxidized using TEMPO with sodium hypochlorite in acetonitrile and NaH2PO4 buffer to give the carboxylic acid intermediate CB8. The carboxylic acid moiety in CB8 was esterified using benzyl alcohol in the presence of coupling agent EDC, DMAP and dichloromethane to give the DC Building Block, DCBB.

Conversion of Anhydrocellobiose to DC Building Block:

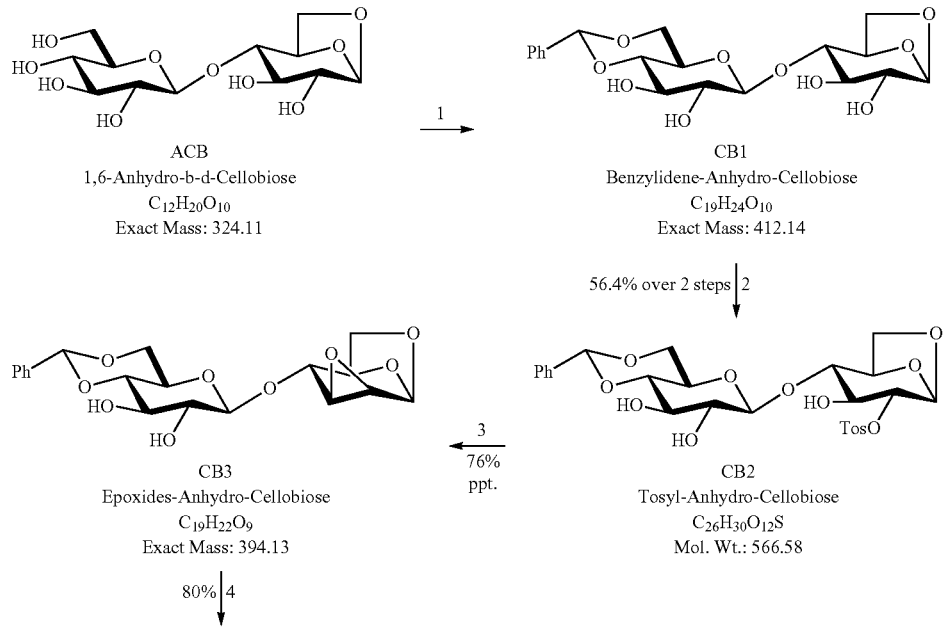

-continued

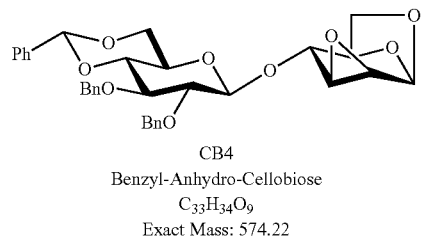

CB4
Benzyl-Anhydro-Cellobiose
$C_{33}H_{34}O_9$
Exact Mass: 574.22

5
90% →

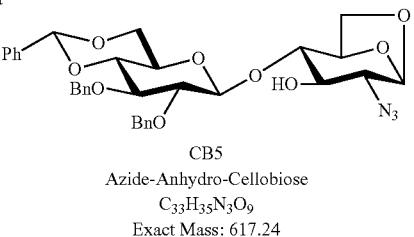

CB5
Azide-Anhydro-Cellobiose
$C_{33}H_{35}N_3O_9$
Exact Mass: 617.24

↓ 6

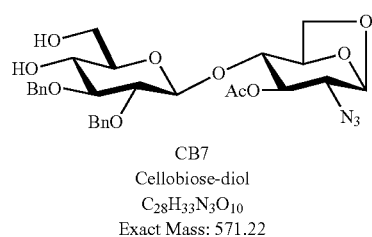

CB7
Cellobiose-diol
$C_{28}H_{33}N_3O_{10}$
Exact Mass: 571.22

← 7
92.2%
over 2 steps

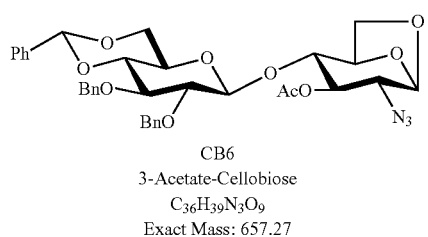

CB6
3-Acetate-Cellobiose
$C_{36}H_{39}N_3O_9$
Exact Mass: 657.27

97%
crude yield ↓ 8

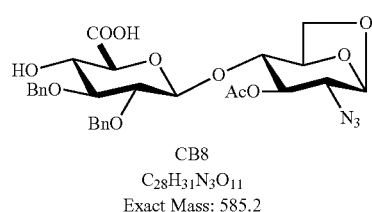

CB8
$C_{28}H_{31}N_3O_{11}$
Exact Mass: 585.2

9
50% →

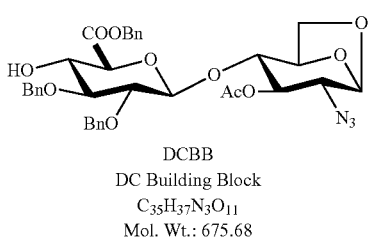

DCBB
DC Building Block
$C_{35}H_{37}N_3O_{11}$
Mol. Wt.: 675.68

Reagents: 1. PhCH(OMe)$_2$ (1.3 eq), CSA (0.1 eq) ACN; 2. p-TosCl (3 eq), DMAP, Pyridine; 3. t-BuOH, KOtBu (3 eq), DCM; 4. NaH (3.3 eq), BnBr (3 eq), DMF; 5. NaN$_3$ (7 eq), DMF/H$_2$O (10%); 6. Ac$_2$O (5 eq), DCM, DMAP; 7. 80% aq TFA, THF; 8. TEMPO (1.0 eq), 10% NaOCl, DCM, H$_2$O, NaH$_2$PO$_4$ buffer; 9. EDC (2 eq), DMAP (0.1 eq), Benzyl-OH (5 eq), DCM Synthesis of the BA Dimer The BA Dimer was prepared in 12 synthetic steps from Monomer B1 and Monomer A2 using the following procedure:

Synthesis of the BA Dimer

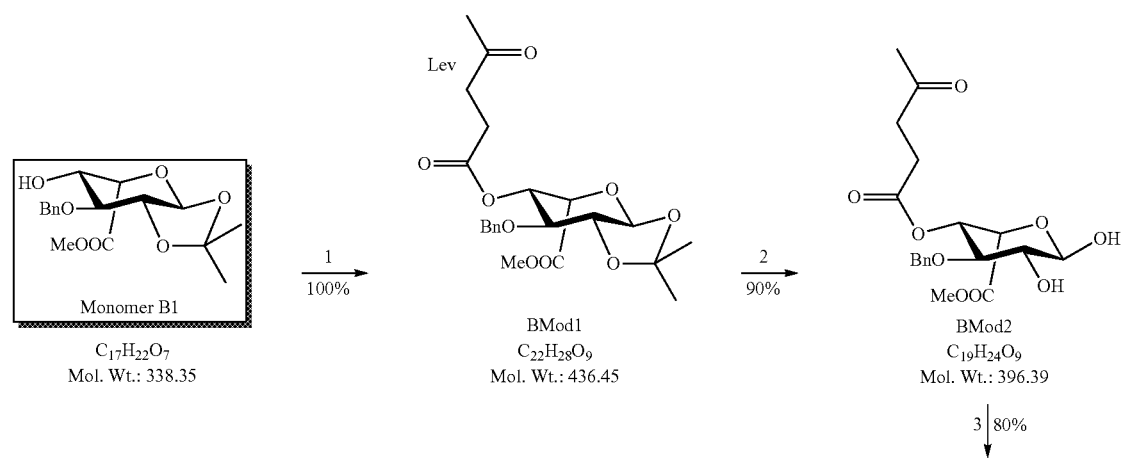

Monomer B1
$C_{17}H_{22}O_7$
Mol. Wt.: 338.35

1
100% →

BMod1
$C_{22}H_{28}O_9$
Mol. Wt.: 436.45

2
90% →

BMod2
$C_{19}H_{24}O_9$
Mol. Wt.: 396.39

3 ↓ 80%

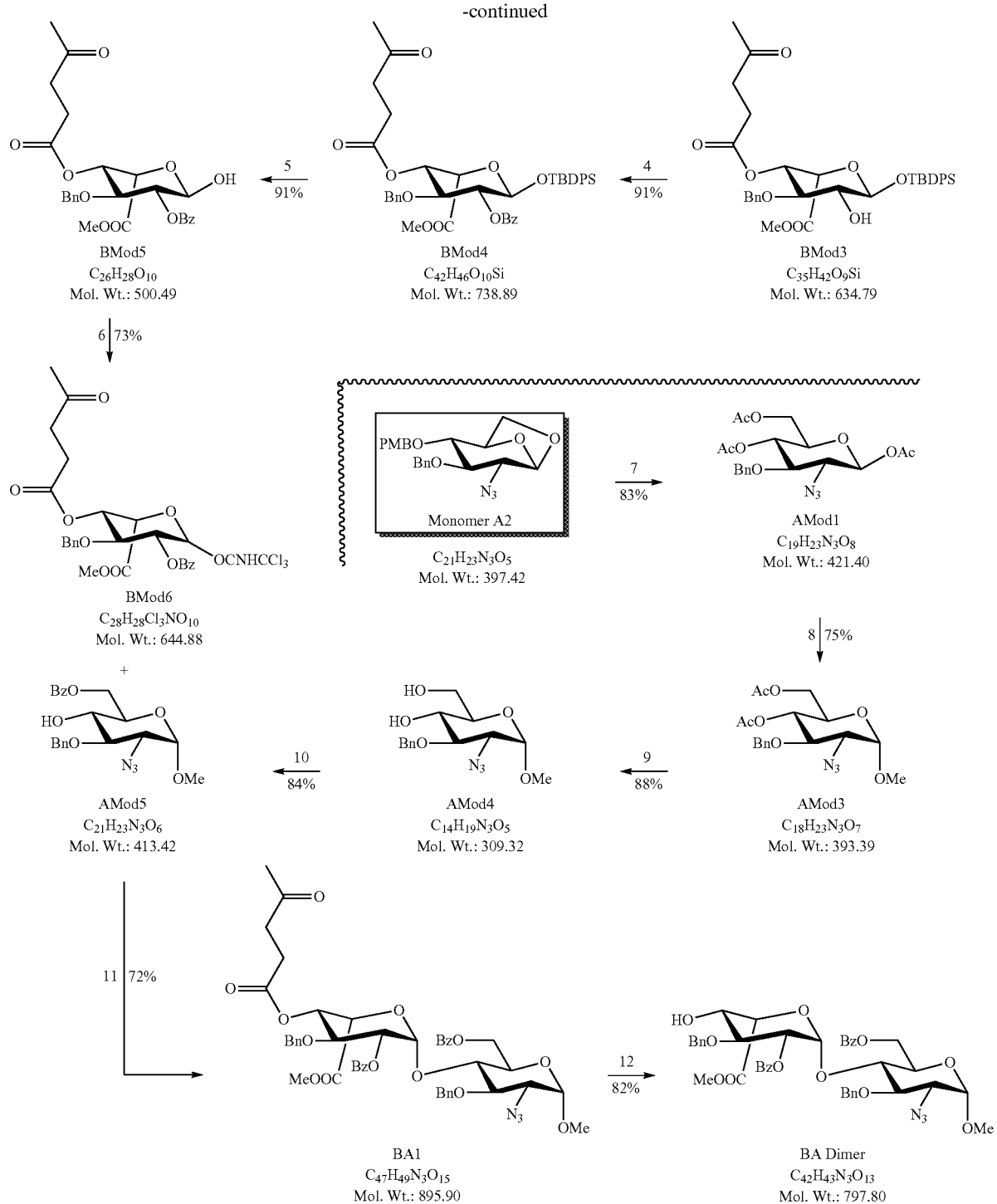

Reagents: 1. Lev₂O, DIPEA, RT, 16 h; 2. 90% TFA, RT, 4 h; 3. Imidazole, TBDPSi-Cl, RT, 3 h; 4. Pyridine, BzCl, RT, 3 h; 5. TBAF, RT, 3 h; 6. TCA, DBU, RT, 2 h; 7. BF₃•Et₂O, Ac₂O, DCM, -20° C. to RT, 3 h; 8. (a) TMS-I, TBAI, RT, 2 h; (b) DIPEA, MeOH, 16 h, RT; 9. NaOMe, Dowex 50WX8-100 resin H+ form, RT, 3 H; 10. Pyridine, Bz-Cl, -40° C. to -10° C., 2 h; 11. BF₃•Et₂O, DCM, -20° C.-RT, 3 h; 12. NH₂NH₂•H₂O, RT, 3 h.

The C4-hydroxyl of Monomer B-1 was levulinated using levulinic anhydride and diisopropylethylamine (DIPEA) with mixing at room temperature for 16 hours to give the levulinate ester BMod1, which was followed by hydrolysis of the acetonide with 90% trifluoroacetic acid and mixing at room temperature for 4 hours to give the diol BMod2. The C1 hydroxyl of the diol BMod2 was silylated with tert-butyldiphenylsilylchloride by mixing at room temperature for 3 hours to give silyl derivative BMod3. The C2-hydroxyl was then benzoylated with benzoyl chloride in pyridine, and mixed at room temperature for 3 hours to give compound BMod4. The silyl group on BMod4 was then deprotected with tert-butyl ammonium fluoride and mixing at room temperature for 3 hours to give the C1-hydroxyl BMod5. The C1-hydroxyl is then allowed to react with trichloroacetonitrile in the presence of diazobicycloundecane (DBU) and mixing at room temperature for 2 hours to give the trichloroacetamidate (TCA) derivative BMod6, which suitable for coupling, for example with Monomer A-2.

Monomer A-2 was prepared for coupling by opening the anhydro moiety with $BF_3.Et_2O$ followed by acetylation of the resulting hydroxyl groups to give the triacetate derivative AMod1.

Monomer A2 was prepared for the coupling reaction by opening the anhydro moiety and acetylation of the resulting hydroxyl groups to give the triacetate derivative AMod1. This transformation occurs using boron trifluoride etherate, acetic anhydride and dichloromethane, between −20° C. and room temperature for 3 hours. The C1-Acetate of AMod1 was then hydrolyzed and methylated in two steps to give the diacetate AMod3. That is, first AMod1 was reacted with trimethylsilyl iodide and mixed at room temperature for 2 hours, then reacted with and tetrabutyl ammonium iodide. This mixture was reacted with diisoproylethylamine and methanol and stirred for 16 hours at room temperature, thus forming AMod3. The C4 and C6 acetates of AMod3 are hydrolyzed with sodium methoxide to give the diol Amod4. The AMod3 mixture was also subjected to mixing at room temperature for 3 hours with Dowex 50 Wx4X8-100 resin in the acid form for neutralization. This formed Amod4. The C6-hydroxyl of AMod4 is then benzoylated by treating with benzoyl chloride in pyridine at −40 C and then allowing it to warm up to −10° C. over 2 hours to give AMod5.

Coupling of monomer AMod5 with the free C4-hydroxyl group of BMod6 was performed in the presence of $BF_3.Et_2O$ and dichloromethane with mixing between −20° C. and room temperature for 3 hours to provide disaccharide BA1. The C4-levulinyl moiety of the disaccharide was then hydrolyzed with hydrazine to give the BA Dimer, which is suitable for subsequent coupling reactions.

Synthesis of EDC Trimer

The EDC Trimer was prepared in 4 synthetic steps from Monomer E and the DC Building Block using the following procedure:

Preparation of EDC-Trimer-CB:

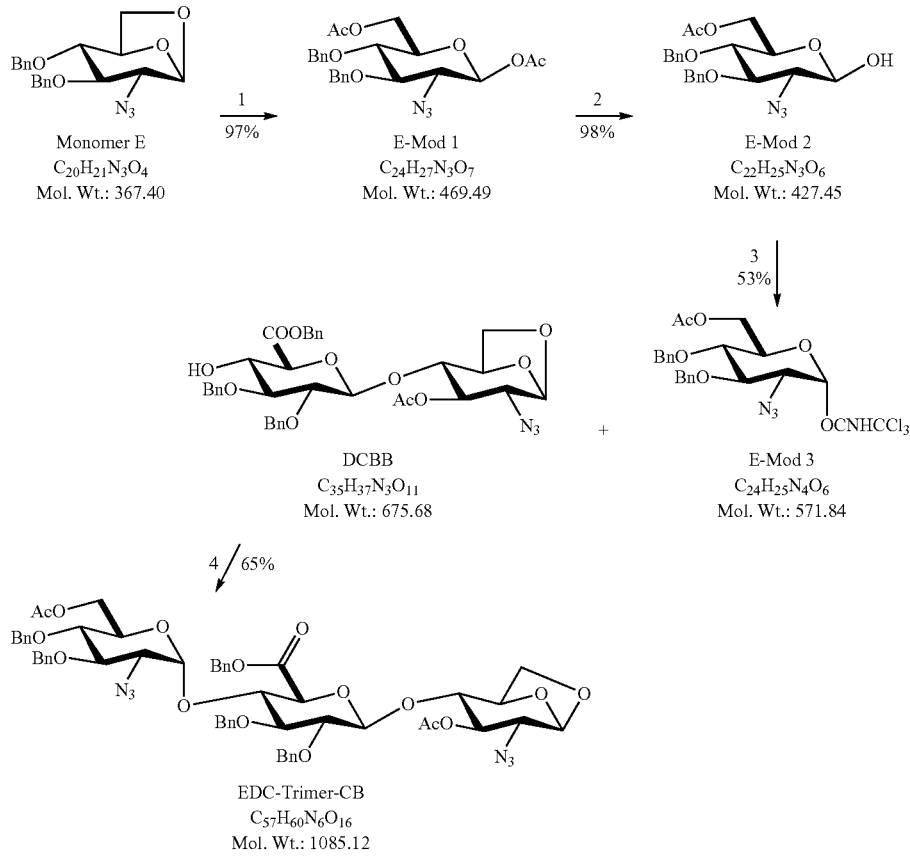

Reagents: 1. $BF_3·Et_2O$, $Ac_2O$, DCM, 0° C.-RT, 3 h; 2. $NH_2NH_2·Ac$, DMF, RT, 3 h; 3. TCA, DBU, DCM, RT, 2 h; 4. DCBB (1 eq), E-Mod 3 (3.0 eq), TES-OTf, -40° C., 2 h;

Monomer E was prepared for coupling by opening the anhydro moiety with $BF_3.Et_2O$ followed by acetylation of the resulting hydroxyl groups to give diacetate EMod1. This occurs by the addition of Monomer E with boron trifluoride etherate, acetic anhydride and dichloromethane at −10° C., and allowing the reaction to warm to room temperature with stirring for 3 hours. The C1-Acetate of EMod1 is then hydrolyzed to give the alcohol, EMod2. This occurs by reacting Emod1 with hydrazine acetate and dimethylformamide and mixing at room temperature for 3 hours. The C1-hydroxyl of Emod2 is then reacted with trichloroacetonitrile to give the trichloro acetamidate (TCA) derivative EMod3 suitable for coupling, which reaction also employs diazabicycloundecene and dichlororethane and mixing at room temperature for 2 hours. The DC Building Block [DCBB], having a free C4-hydroxyl group on the 'D' ring, was then coupled with the TCA derivative EMod3 in the presence of triethylsilyl triflate to give the trisaccharide 1EDC Trimer-CB Synthesis of the EDCBA Pentamer The EDCBA Pentamer was prepared using the following procedure:

Preparation of the Fully Protected Pentamer:

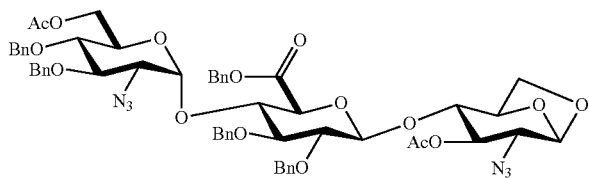

EDC Trimer-CB
$C_{55}H_{60}N_6O_{18}$
Mol. Wt.: 1093.09

1 | 65%

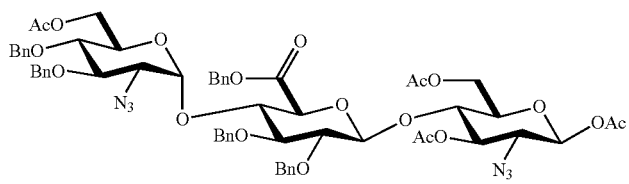

EDC-1-CB
$C_{59}H_{66}N_6O_{21}$
Mol. Wt.: 1195.18

2 | 62%

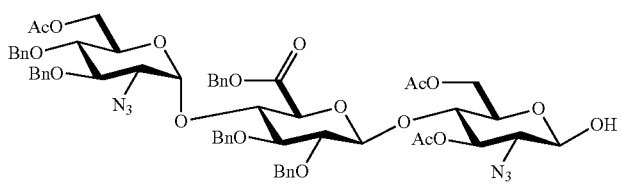

EDC-2-CB
$C_{57}H_{64}N_6O_{20}$
Mol. Wt.: 1153.15

3 | 78%

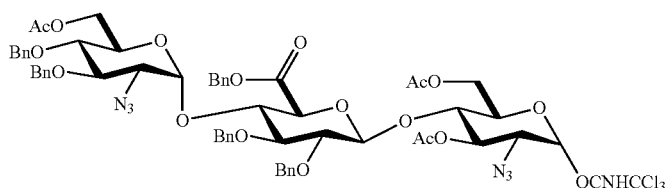 + 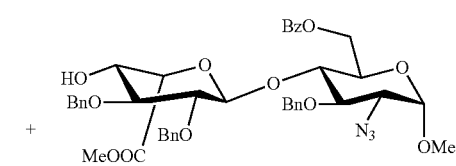

EDC-3-CB
$C_{61}H_{64}Cl_3N_7O_{16}$
Mol. Wt.: 1289.56

4 | 71%

BA Dimer
$C_{42}H_{43}N_3O_{13}$
Mol. Wt.: 797.80

-continued

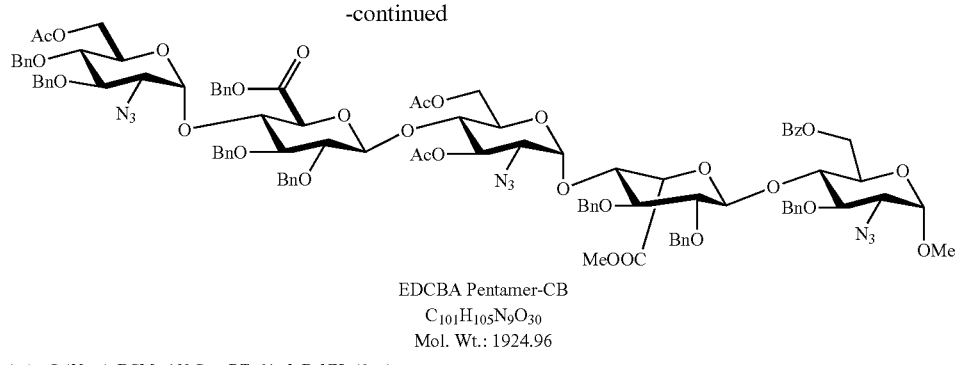

EDCBA Pentamer-CB
C$_{101}$H$_{105}$N$_9$O$_{30}$
Mol. Wt.: 1924.96

Reagents: 1. BF$_3$·Et$_2$O (8 eq), Ac$_2$O (30 eq), DCM, -10° C. to RT, 6 h; 2. BnNH$_2$ (6 eq), THF, -10° C., 4 h; 3. TCA (20 eq), DBU (0.5 eq), RT, 2 h; 4. TES-Tf (0.5 eq), -30° C., 2 h;

The preparation of EDCBA Pentamer-CB is accomplished as follows. The EDC Trimer-CB, a diacetate intermediate, is prepared for the coupling reaction with Dimer BA by initially opening the anhydro moiety and acetylation of the resulting hydroxyl groups to give the tetraacetate derivative EDC1-CB. This occurs by reacting the EDC Trimer with boron trifluoride etherate, acetic anhydride and dichlormethane and stirring between –10° C. and room temperature for 6 hours. The C1-Acetate of EDC1-CB is then hydrolyzed to give the alcohol, EDC2-CB, by reacting EDC1-CB with benzylamine [BnNH$_2$] and tetrahydrofuran and mixing at –110° C. for 4 hours. The C1-hydroxyl of EDC2-CB is then reacted with trichloroacetonitrile and diazabicycloundecane, with mixing at room temperature for 2 hours, to give the trichloro acetamidate (TCA) derivative EDC3-CB suitable for coupling.

The Dimer BA, having a the free C4-hydroxyl group, is coupled with trisaccharide EDC3-CB1 in the presence of trimethylsilyltriflate at –40° C. mixing for 2 hours to give the pentasaccharide EDCBA-Pentamer-CB.

Synthesis of Fondaparinux

Fondaparinux was prepared using the following procedure:

Conversion of FPP (also referred to a Fully Protected Pentamer) to Fondaparinux Sodium:

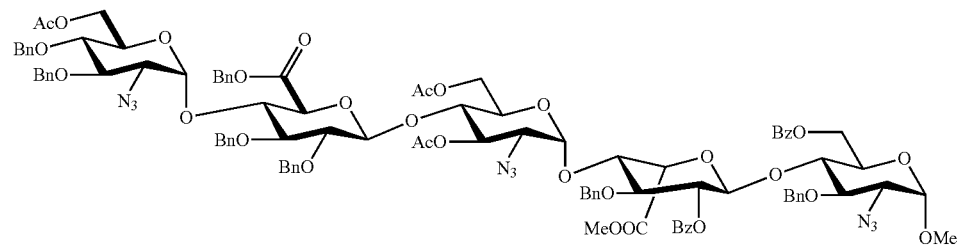

EDCBA Pentamer CB
C$_{101}$H$_{105}$N$_9$O$_{30}$
Mol. Wt.: 1924.96

1 | crude
↓

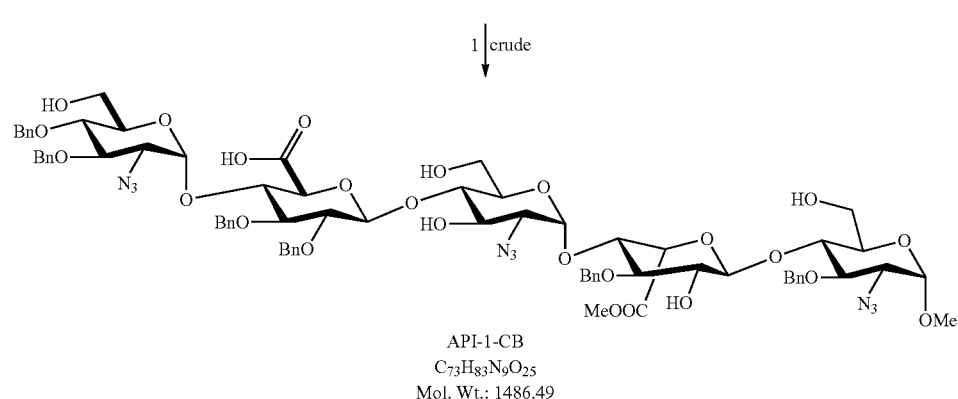

API-1-CB
C$_{73}$H$_{83}$N$_9$O$_{25}$
Mol. Wt.: 1486.49

2 | 84% over 2 steps
↓

-continued

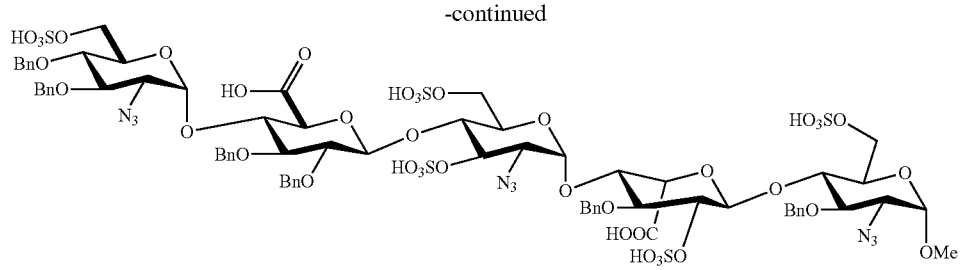

API-2-CB
C$_{73}$H$_{83}$N$_9$O$_{40}$S$_5$
Mol. Wt.: 1886.81

3 ↓ 95.7%

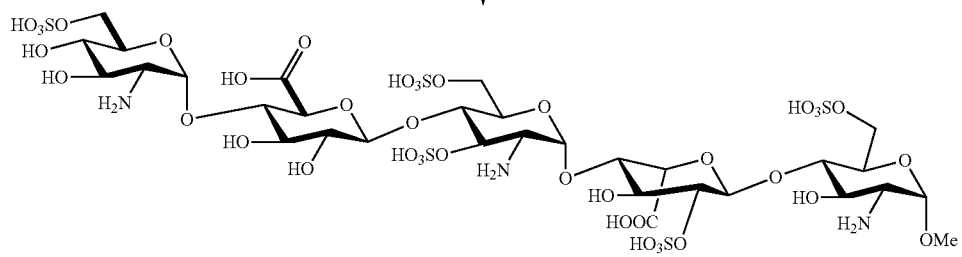

API-3-CB
C$_{31}$H$_{53}$N$_3$O$_{40}$S$_5$
Mol. Wt.: 1268.08

4 ↓ 65%

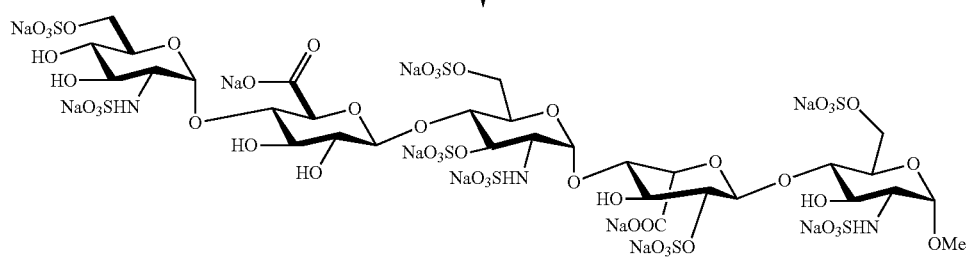

FONDAPARINUX SODIUM
C$_{31}$H$_{43}$N$_3$Na$_{10}$O$_{49}$S$_8$
Mol. Wt.: 1728.09

Reagents: 1. NaOH, H$_2$O$_2$, LiOH, Dioxane, RT, 24-48 h; 2. Py•SO$_3$, DMF, 60° C., 2 h, CG-161 purification; 3. 10% Pd/C, H$_2$, 72 h; 4. (a) Py•SO$_3$, NaOH, NH$_4$OAc, 12 h, (b) HiQ NH$_4$OAc/NaCl ion-exchange, Sephadex Desalt and (c) HiQ NaCl ion-exchange, Sephades Desalt.

The ester moieties in EDCBA Pentamer-CB were hydrolyzed with sodium and lithium hydroxide in the presence of hydrogen peroxide in dioxane mixing at room temperature for 24-48 hours to give the pentasaccharide intermediate API1-CB. The five hydroxyl moieties in API1-CB were sulfated using a pyridine-sulfur trioxide complex in dimethylformamide, mixing at 60° C. for 2 hours and then purified using column chromatography (CG-161), to give the pentasulfated pentasaccharide API2-CB. The intermediate API2-CB was then hydrogenated to reduce the three azides on sugars E, C and A to amines and the reductive deprotection of the six benzyl ethers to their corresponding hydroxyl groups to form the intermediate API3-CB. This transformation occurs by reacting API2-CB with 10% palladium/carbon catalyst with hydrogen gas for 72 hours. The three amines on API3-CB were then sulfated using the pyridine-sulfur trioxide complex in sodium hydroxide and ammonium acetate, allowing the reaction to proceed for 12 hours. The crude fondaparinux is purified and is subsequently converted to its salt form. The crude mixture was purified using an ion-exchange chromatographic column (HiQ resin) followed by desalting using a size exclusion resin or gel filtration (Biorad Sephadex G25) to give the final product, fondaparinux sodium.

Synthesis of Monomer A2

Step 1: Formation of IntA1 by De-Acetylation of Tri-O-Acetyl D-Glucal

The Tri-O-Acetyl-D-Glucal [SM-A](100 g, 367 mmol) is dissolved in dry MeOH [1.5 L], and then NaOMe (110 mmol, 5.95 g) is added into reaction mixture. Within about 20 minutes, TLC (40% EtOAc/60% hexanes & 100% EtOAc) confirmed de-acetylated glucal. The reaction is quenched with 50WX4 cation exchange resin until pH is near 7.0 by pH strip paper. The mixture is filtered and evaporated to dryness under vacuum to yield syrupy glucal intermediate IntA1(59 g). Theoretical yield 100 g×(146/272) 53.7 g TLC IntA1 $R_f$=0.1, SiO2, 100% Ethyl Acetate Step 2 & 3: Conversion to 1,6-anhydro-2-deoxy-2-iodo-β-D-glucopyranose [IntA2]

The de-acetylated syrupy D-glucal IntA1 from step 1 (53.7 g, based on quantitative yield, 367 mmol) is treated with bis(tributyltin)oxide (175 g, 150 mL, 294 mmol, 0.8 eq) and activated powdered 3 A molecular sieves [150 g] in refluxing dry Acetonitrile [3.5 L] for 16 hours. Next morning, the mixture is cooled to 5° C. under $N_2$ and $I_2$ [140 g, 551 mmol] is added in one portion. The dark brown mixture is stirred for 15 nm minutes 5° C., then for 3 hours at room temperature. TLC (either 1/1:toluene/Acetone or 100% EtOAc) showed the complete conversion of D-glucal ($R_f$ 0.14) into iodo derivative ($R_f$ 0.45). The mixture was filtered through Celite and concentrated. To this residue is added saturated aqueous sodium thiosulfate (200 mL) and hexanes (200 mL). The biphasic mixture is vigorously mixed for 16 hours. The aqueous phase is then continuously extracted with DCM (1.5 Lt.) for 24 hours (till no product was detected in the aqueous layer). The organic extract is dried over $Na_2SO_4$ and concentrated. To the residue was added 500 mL acetone. The yellow insoluble material was filtered and discarded. The acetone solution was evaporated to dryness. The residue was treated with EtOAc to separate the desired iodo-1,6-anyhdro derivative, hatA2 as a white solid. Yield: 76 g. TLC IntA2 $R_f$=0.7, SiO2, 100% Ethyl Acetate.

Step 4: Conversion to 1,6:2,3-bisanhydro-4-O-p-ethoxybenzyl-β-D-glucopyranose [IntA3]

Iodo derivative, IntA2 (152 g, 279 mmol) from the previous step was co-evaporated twice using dry Acetonitrile [volume?], dissolved in DMF (2 L) and cooled to –20° C. in dry ice bath. 4-methoxybenzyl chloride [94 mL, 698 mmol, 2.5 eq.] and NaH (60% in mineral oil) [22.4 g, 559 mmol, 2.0 eq.] is added and the reaction mixture is stirred for 2 hours (–20° C. to room temperature). TLC (20% EtOAc/80% hexanes) confirmed the complete conversion of the starting material to epoxide and some non-benzylated epoxide (<10%). The reaction quenched by pouring the mixture into 2000 g of crushed ice. The mixture is diluted with 2 L of THF and 4 L of EtOAc. The aqueous layer is extracted four times with EtOAc. The combined organic layer is washed with saturated aqueous NaCl (2 L), dried with $Na_2SO_4$, filtered and solvent is removed in vacuum. Flash chromatography on silica gel (hexanes:EtOAc/6:4) afforded 143 g of desired epoxide, IntA3. TLC IntA3 $R_f$=0.8, $SiO_2$, 100% Ethyl Acetate; IntA2 $R_f$=0.7, $SiO_2$, 100% Ethyl Acetate Step 5: Conversion to 1,6-anhydro-2-azido-4-O-p-methoxybenzyl-2-deoxy-β-D-glucopyranose [IntA4]

The Epoxide derivative, IntA3 [142 g, 537 mmol] is dissolved in DMF [5.68 L] and water [625 mL]. Sodium azide [210 g, 3224 mmol, 6 eq.] is then added. The mixture is heated to 120° C. for 12 hours, cooled to room temperature and poured into a mixture of water and EtOAc. The aqueous layer is extracted four times with ethyl acetate and the combined organic layers are washed with brine and dried over sodium sulfate, filtered and concentrated. The crude product is purified by silica gel to give 124 g of pure azide sugar derivative, IntA4. TLC IntA4 R=0.6, SiO2, 50% Ethyl Acetate & 50% Hexanes; IntA3 $R_f$=0.7, SiO2, 50% Ethyl Acetate & 50% Hexanes.

Step 6: Conversion to 1,6-anhydro-2-azido-3-Benzyl-4-O-p-methoxybenzyl-2-deoxy-β-D-glucopyranose [Monomer A2]

Azido-PMB-sugar derivative, IntA4 [2,865 g, 9.32 mmol] is dissolved in dry DMF [30 mL] and cooled to 0° C. Sodium Hydride (60% in mineral oil) [0.45 g, 11.2 mmol, 1.2 eq.] is added in one portion followed by Benzyl Bromide [1.33 mL, 11.2 mmol, 1.2 eq.] drop wise. The mixture is stirred at 0° C. until all addition was finished, then allowed to warm to room temperature. TLC (30% EtOAc/70% hexanes) showed the complete conversion of S.M to desired product in one hour. (Rf from 0.2 to 0.7). After one hour the reaction mixture is poured into ice/water. Then it is diluted with DCM and saturated aqueous $NH_4Cl$. The aqueous layer is back extracted with DCM. The combined organic layers are washed with saturated aqueous $NH_4Cl$, brine, and water, dried over $Na_2SO_4$, filtered, and evaporated to oily residue. The residue is subjected to silica gel chromatography to yield pure bisether derivative, Monomer A2 in 90% yield, TLC Monomer A2 $R_f$=0.7, $SiO_2$, 30% Ethyl Acetate & 70% Hexanes; IntA4 $R_f$=0.2, $SiO_2$, 30% Ethyl Acetate & 70% Hexanes The conversion of Monomer A2 to AMod5, Steps 7 to 10 is reported under the section detailing the BA Dimer preparation.

Synthesis of Monomer B1

Step 1. Preparation of 3-Obenzyl-diacetoneglucose [IntB1]

35 mL of THF was chilled in an ice/methanol bath. A condenser, pressure addition funnel and septa were also fitted to the flask. The system was purged with dry nitrogen while cooling. The sodium hydride (60% in mineral oil) [5,769 g, 144.23 mmol] was slowly added to this flask. The diacetone glucose [SM-B, 30 g, 115.38 mmol] was dissolved in a 1 to 1 mixture of DMF [172.5 mL] and THF [172.5 mL]. This was charged in the pressure addition funnel and slowly dripped into the sodium hydride over 20 minutes. Once all the diacetone glucose had been added, the mixture was stirred for 20 minutes before the addition of benzyl bromide [17.27 mL, 144.23 mmol]. With all the benzyl bromide added the solution was removed from the ice bath and slowly heated to reflux (65° C.). The progress of the reaction was checked by TLC (20% EtOAc/Hexanes). Upon completion the reaction was quenched by pouring the contents over ice and adding 100 mL of $H_2O$ and 100 mL saturated ammonium chloride. 350 mL of ethyl acetate was added and the mixture separated. The aqueous layer was re-extracted with 125 mL EtOAc and once with 100 mL of 1:1 EtOAc/THF. The combined organic layers were dried over sodium sulfate and rotovapped to yellow syrup. The crude material was used in the next step. Yield: assumed quantitative. TLC of IntB1-$R_f$=0.45 in elution buffer: 20% Ethyl Acetate & 80% Hexanes Step 2. Selective Hydrolysis of 5,6-isopropylidene [IntB2]

The Crude material (assuming quantitative yield) from step one was dissolved in 66% acetic acid [112.5 mL]/water [62.5 mL] and heated at 400 overnight. The next morning TLC was checked using 30% EtOAc/Hexanes and the reaction quenched by the careful addition of saturated potassium carbonate [~250 mL] until the pH of the solution reached 7. The solution was diluted with water and transferred to a separation funnel. This was extracted three times with DCM. The combined organic layers were washed twice with brine before being dried over sodium sulfate. This was then filtered and rotovapped before being re-dissolved in a minimum amount of DCM for silica gel chromatography. 2 L of silica used and eluted with 2 L of 30%, 3 L 40%, 3 L 50%, 1 L 60%, and 2 L 65% EtOAc/Hexanes. 88.5% yield over two steps. 1. TLC of IntB2-$R_f$=0.16 in elution buffer: 30% Ethyl Acetate & 70% Hexanes Step 3: Oxidative Cleavage of 5,6-Hydroxy by Sodium Periodate on 3-Obenzyl-5,6-dihydroxy-1,2-isopropylideneglucofuranose. [IntB3]

The 5,6-hydroxy starting sugar [IntB2, 31.2 g, 100.61 mmol] was placed into a flask and dissolved in DCM [375 mL]. To this was added 375 mL of water and tetrabutylammonium bromide [3.24 g, 10.06 mmol]. The mixture was covered in aluminum foil to exclude as much light as possible from it in order to prevent periodate decomposition. The sodium periodate [25.82 g, 120.7 mmol] was weighed out and added to the mixture in three portions. Once addition was complete the flask was allowed to slowly warm to room temperature. The progress of the reaction was checked by TLC (40% EtOAc/Hexanes). Once complete the reaction was transferred to a separatory funnel and extracted. The aqueous layer was re-extracted with 3×200 mL DCM. The organic layers were combined and washed twice with 150 mL $H_2O$ and once with 200 mL brine. Silica Gel chromatography yielded the pure product. Yield: 87.7%. TLC of IntB3-$R_f$=0.55 in elution buffer: 40% Ethyl Acetate & 60% Hexanes Step 4: Conversion to L-Idose configured thioortho ester [IntB4]

All glassware was dried in an oven overnight to ensure it was dry. To a dried flask was added the tris(phenylthio) methane [54.62 g, 160.4 mmol, 1.8 eq.) and dry THF (125 mL). This was then cooled in a dry ice/acetone bath to −78° C. Once at −78° C. the n-butyl lithium (1.6M in Hexanes, 100 mL, 160.4 mmol, 1.8 eq.) was added drop wise. The bright yellow solution was allowed to warm to −50° C. over one hour and then cooled to −78° C. for 30 minutes before the addition of crude from step three.

The crude material, IntB3 (24.8 g, 89.11 mmol) from step 3 was dissolved in 125 mL dry THF and charged in a pressure addition funnel. This was added drop wise, while maintaining −78° C., over the next 15 minutes. The reaction was stirred for an additional hour at −78° C. before being allowed to warm to room temperature. This was quenched with a solution of saturated ammonium chloride (660 mL). The solution was transferred to a separation funnel and extracted with ethyl acetate. The aqueous phase was re-extracted three times with 100 mL EtOAc. The combined organic layers were dried over sodium sulfate, filtered, and concentrated under reduced pressure. The Crude material was used in the next step. Yield: 90%. TLC of IntB4-$R_f$=0.70 in elution buffer: 40% Ethyl Acetate & 60% Hexanes Step 5: Methyl 3-O-benzyl-1,2-isopropylidene-α-L-idofuranuronate [IntB5]

Into a flask was placed the copper(II) chloride (43.51 g, 323.62 mmol) and copper(II) oxide (10.94 g, 137.54 mmol) along with methanol (600 mL) and water (50 mL) in a 12 to 1 ratio. The crude IntB4 (50 g, 80.9 mmol) from step 4 was dissolved in a minimum amount of DCM and slowly added to the mixture. The reaction was stirred until complete as indicated by TLC (40% EtOAc/Hexanes). Once complete the reaction was passed through a bed of Supercel [filter agent] to remove the copper(I) oxide. The reaction mixture was then concentrated under reduced pressure and the green-white product was extracted with EtOAc and $H_2O$. The aqueous layer was re-extracted with 2×150 mL EtOAc. The combined organic layers were washed with 2×100 mL $H_2O$ and 2×100 brine before being dried over sodium sulfate. Purification by silica gel chromatography yielded the pure product (2 L of silica and eluted with 2 L, of each 10%, 15%, 20%, 25%, 30% EtOAc/Hexanes) as light yellow oil. Yield: 80%. TLC of IntB5-$R_f$=0.3 in elution buffer: 40% Ethyl Acetate & 60% Hexanes Step 6: Cleavage of the 1,2-isopropylidene on 3-O-benzyl-1,2-isopropylidene-α-L-idofuranuronate [IntB6]

The Starting material IntB5 (22 g, 65 mmol) was dissolved in a minimum amount of DCM. To this was added 90% TFA/Water (200 mL) and stirred at room temperature. The reaction was checked by TLC (30% EtOAc/Hexanes for the starting material and 60% EtOAc/Hexanes for the product) and found to be complete after 30 min. This was then diluted with toluene and rotovaped to nearly dryness. Co-evaporated with toluene 3×40 mL. Silica gel chromatography (2 L silica and eluted with 2 L of 30% 40%, 40%, 50%, 60% EtOAcHexanes) afforded the product as a white to off white solid. Yield of the desired product in the mixture was 55%. TLC of IntB6$R_f$=0.25 in elution buffer: 60% Ethyl Acetate & 40% Hexanes Step 7: Methyl 3-O-benzyl-1,2-isopropylidene-α-D-Glucopyranuronate [Monomer B1]

The sugar derivative IntB6 (230 g, 0.8 mol, 1 eq.) was dissolved in 1 L DMF in a three neck round bottom flask fitted with magnetic stir. The center neck was capped. To the other necks were fitted a temperature probe and controller and a pressure addition funnel. The reaction mixture was cooled to zero in an ice/water/salt bath. 2-methoxypropene (766.11 mL, 8 mol, 10 eq.) was added when the mixture was about 4-5° C. This was then stirred until a temperature of zero was reached. The CSA (18.58 g, 0.08 mol, 0.1 eq.) was dissolved in 125 ml DMF and charged into a dropping funnel. With the temperature at zero slow, drop wise addition of CSA begun. When temperature was seen to rise, and continue to increase quickly the addition was halted and the system allowed for cooling to zero again. After the initial exotherm it was found that the additional CSA did not cause the mixture to heat up. With all the CSA added, the mixture was allowed to warm to room temperature. As the reaction warms, the color of the reaction proceeds to get very dark. Progress of the reaction was followed by TLC (40% E-H), the product was found to go higher. Once the reaction is complete, 800 ml of Methanol was added and stirred for one hour before the reaction was quenched with 200 ml TEA. When the TEA was added the mixture became much lighter in color. The reaction mixture was evaporated to remove the excess methanol before extraction. Extraction was done using EtOAc/$H_2O$. The organic layer was washed 2× with water. The Aqueous layer was washed once with EtOAc. The combined organic layer was washed once with brine and dried over sodium sulfate. The sodium sulfate was filtered before concentration under reduced pressure in preparation for a silica column. Silica column was preformed on 15 L of silica (10% E-H). Product was eluted with 20 L of each: 10%, 15%, 20% and 40 L of 30% followed by 20 L of 40%. The pyranose was separated from the furanose. Pure fractions were pooled and concentrated. TLC of Monomer B1-$R_f$=0.40 in elution buffer: 60% Ethyl Acetate & 40% Hexanes The conversion of Monomer BE to BMod6, Steps 8 to 13 is reported under the section detailing the BA Dimer preparation.

Conversion of Anhydrocellobiose [ACB] to DC Building Block [DC BB]

Step: 1 Preparation of Benzylidene-Anhydro-Cellobiose (CB1)

Benzylidene Formation

To a suspension of 800 gram (2468.30 mmol, 1 eq) commercially available, 1,6-Anhydro-β-d-cellobiose (ACB) in 12 Lit of Acetonitrile was added 57.33 gram (246.83 mmol, 0.1 eq) of Camphorsulfonic Acid (CSA). Then 481.38 mL (3208.79 mmol, 1.3 eq) of Benzaldehyde dimethylacetal was added dropwise and the reaction mixture was heated to reflux for 2 hours. The white suspension became a clear solution after 30 minutes of reaction. TLC (20% methanol/ethyl acetate) indicated that the reaction had gone to completion. The reaction mixture was cooled to room temperature and concentrated under vacuum using a rotary evaporator. The residue (~570 g) of CB1 was used for step 2 without further purification.

Step: 2 Preparation of Tosyl-Anhydro-Cellobiose (CB2): Tosylation

The crude Benzylidene-Anhydro-Cellobiose (CB1) product from step 1 ~570 gr, (1382.15 mmol, 1 eq) was dissolved in 2.5 Lit of pyridine. Then, 34 gram (276.44 mmol) of N,N-dimethyl aminopyridine (DMAP) and 789.70 grams (4146.46 mmol, 3 eq) of p-Toluene sulfonyl chloride were added. The reaction mixture was stirred for 6 hr under an atmosphere of $N_2$ at room temperature. TLC (5% and 20% methanol/ethyl acetate) indicated that the reaction had gone to completion. The reaction mixture was quenched in methanol (400 mL) and concentrated under vacuo, the residue was diluted with ethyl acetate (4 lit) and washed with $H_2O$ (2×1.5 Lit). The organic phase was dried over sodium sulfate, filtered, and evaporated under vacuo. The residue was co-evaporated with toluene (2×1.5 Lit) to dryness. The residue was purified by silica gel column chromatography (80% ethyl acetate/20% heptane to 100% ethyl acetate gradient) to give Tosyl-Anhydro-Cellobiose (CB2) as a white foam (442.0 grams, 56.4% yield over 2 steps).

Step: 3 Preparation of Epoxide-Anhydro-Cellobiose (CB3)-Epoxide Formation

A solution of 262.82 grams (2342.14 mmol, 3 eq) of Potassium-tert.-butoxide in 1.8 Lit of tert-Butyl alcohol was slowly added to a solution of 442.0 grams (780.72 mmol, 1 eq) of Tosyl-Anhydro-Cellobiose (CB2) dissolved in 5 liters of dry dichloromethane at room temperature. The reaction mixture was heated and allowed to reflux gently for approximately 2 hours under an atmosphere of $N_2$. The TLC (100% ethyl acetate) analysis showed conversion of the starting material into the product. The reaction mixture was cooled to room temperature and slowly poured into 5 Lit of saturated ammonium chloride solution and extracted with dichloromethane (2×2.5 Lit). The organic layers were combined, dried with sodium sulfate, filtered, and evaporated under vacuo to a yellow solid (~234 g, 76.06% crude yield), which was used for Step 4 without further purification.

Step: 4 Preparation of Benzyl-Epoxide-Cellobiose (CB4)-Benzylation

To a suspension of 78.30 grams (1958.0 mmol, 3.3 eq) of sodium hydride (60% oil) in 600 mL of dry DMF at −28° C. was slowly added a solution of 234.0 grams (593 mmol, 1 eq) of Epoxide-Anhydro-derivative (CB3) in 800 mL of dry DMF, maintaining the temperature below −15° C. Upon completion of addition, the mixture was slowly warmed to room temperature and a solution of 211.71 mL (1780.0 mmol, 3 eq) of Benzyl Bromide in 500 ml of dry DMF was added. After stirring the reaction for 16 hours at room temperature under $N_2$ atmosphere, TLC (40% ethyl acetate/60% heptane) analysis showed conversion of the starting material into the product. The reaction mixture was quenched in ice and extracted with ethyl acetate (2×4 Lit), dried over sodium sulfate, filtered, and evaporated under vacuo. The residue was purified by silica gel column chromatography (10% ethyl acetate/90% heptane gradient) with 5% gradient to afford product (CB4) (275.0 g, 80%).

Step: 5 Preparation of Azide-Anhydro-Cellobiose (CB5)-Azidation Reaction 275.0 grams (478.58 mmol, 1 eq) of Dibenzyl-Epoxide-Cellobiose (CB4) was dissolved in 9.56 Lit of DMF, 1.06 Lit of $H_2H$ and 217.75 grams (3350.04 mmol, 7 eq) of Sodium Azide was added. The reaction mixture was heated to reflux. TLC (40% ethyl acetate/heptane) showed the completion of reaction after 16 hours. Upon completion, the mixture was diluted with ethyl acetate (5 Lit) and washed with water (1×1.5 Lit) and evaporated under vacuo. The residue was co-evaporated with toluene (3×2 Lit) to dryness. The residue was purified by silica gel column chromatography (30% ethyl acetate/70% heptane gradient) to afford product (CB5) as white solid (266.0 gram 90%).

Step: 6 Preparation of Acetate-Anhydro-Cellobiose (CB6)-Acetylation 266.0 grams (430.66 mmol, 1 eq) of Azide-Anhydro-Cellobiose (CB5) was dissolved in 2 Lit of dry Dichloromethane and 78.92 gram (64.60 mmol) of N,N-Dimethylaminopyridine (DMAP) was added. The solution was cooled to 0° C. and 203.57 mL (2153.32 mmol, 5 eq) of Acetic anhydride was added. The mixture was warmed to room temperature and stirred for 2 hr or until reaction was complete by TLC (40% ethyl acetate/heptane). The reaction was quenched with methanol (1.5 Lit), concentrated in vacuo and gave 284.0 gram of white foam crude product. The crude product of Acetate-Anhydro-Cellobiose (CB6) was used for step 7 without further purification.

Step: 7 Preparation of Intermediate CB7-Deprotection of Benzylidene Moiety 284.0 grams (430.51 mmol, 1 eq) of Acetate-Anhydro-Cellobiose (CB6) was dissolved in 2.16 Lit of Tetrahydrofuran (THF). The solution was cooled to 0° C. and 5.68 Lit of 80% aqueous Trifluoroacetic acid (TFA) was added slowly. The reaction mixture was allowed to warm to room temperature and stirred for 4 hours. TLC (60% ethyl acetate/heptane) showed the completion of the reaction. The reaction mixture was cooled to −5.0° C., and adding 8.2 Lit of Triethylamine (TEA, 5963.13 gram, 58.93 mol, 1.0 equiv/TFA) slowly into the solution until pH was 7.0. During the TFA addition maintain temperature between −5.0° C. to 5.0° C. Then residue was diluted with $CH_2Cl_2$ (3 Lit) and washed with $H_2O$ (1×1.5 Lit). The organic layer was extracted with 10% sodium bicarbonate solution (3×1.0 Lit), dried over anhydrous sodium sulfate, filtered and evaporated to dryness. The residue was purified by silica gel column chromatography (60% gradient ethyl acetate in heptane) as white foam of Cellobiose-diol (CB7) (227.0 g, 92.2%).

Step: 8 Preparation of Carboxylic acid-Cellobiose (CB8)-Oxidation of 6-Hydroxyl 227.0 gram (397.15 mmol, 1 eq) of cellobiose-diol (CB7) was dissolved in 12.5 Lit of Acetonitrile (ACN) and 8.2 Lit of (1:1) 0.67 M $Na_2HPO_4$ and 0.67 M $NaH_2PO_4$ buffer pH 6.5. The reaction mixture was heated to 35° C. Then 62.05 gram (397.15 mmol, 1 eq) of 2,2,6,6-Tetramethyl-piperidine-1-oxyl (TEMPO) reagent and 415 ml of NaOCl solution containing 10-13% available chlorine was added. The reaction mixture was stirred at 35° C. until reaction was complete by TLC (5% methanol/ethyl acetate). After 16 hours the reaction was cooled to 0° C., diluted with water (2 Lit) and the pH was adjusted to pH 8.5-9.0 using 1 N NaOH (2.5 Lit). The reaction mixture was then poured into ice-cold 500 ml of sodium sulfite solution (30 gram in 500 ml of water). The reaction was extracted with methyl t-butyl ether (MTBE) (2 Lit) and organic layer was discarded. The aqueous layer was acidified with 1.0 N HCl (6 Lit) to pH 2.5. The reaction was then extracted with dichloromethane, died with anhydrous sodium sulfate, and evaporated to a syrup (212.0 gram). The crude product of Carboxylic acid-Cellobiose (CB8) was used for step 7 without further purification.

Step: 9 Preparation of Benzylester-Anaydro-Cellobiose (DCBB)-Benzylation of Carboxylic Acid 212 gram (362.05 mmol, 1 eq) of carboxylic acid-Cellobiose (CB8) from step 8 was dissolved in 3.5 Lit of dry DCM and 11.05 gram (90.52 mmol) of N,N-Dimethylaminopyridine (DMAP) was added. The 138.80 gram (724.09 mmol, 2 eq) of 1-ethyl-3-(3-dimethylaminopropyl)carbodiimide hydrochloride (EDC) and 177.90 ml (1810.24 mmol, 5 eq) of benzyl alcohol was added slowly and the reaction was stirred at room temperature under $N_2$ atmosphere. TLC (60% ethyl acetate/heptane) showed the completion of the reaction after 16 hr. The residue was diluted with DCM (2.5 Lit) and extracted with water (1×1.5 mL) followed by saturated sodium bicarbonate solution (1×1.5 mL) and Brine (1×1.5 mL). The mixture was then dried over anhydrous sodium sulfate, filtered, and evaporated under vacuo. The residue was purified by silica gel column chromatography (5% gradient ethyl acetate in heptane) and gave 124.0 gram product of Benzylester-Anhydro-Cellobiose DCBB (50% yield).

Synthesis of the BA Dimer

Step 1. Preparation of BMod1, Levulination of Monomer B1

A 100 L reactor was charged with 7.207 Kg of Monomer B1 (21.3 moles, 1 equiv), 20 L of dry tetrahydrofuran (THF) and agitated to dissolve. When clear, it was purged with nitrogen and 260 g of dimethylamino pyridine (DMAP, 2.13 moles, 0.1 equiv) and 11.05 L of diisopropylethylamine (DIPEA, 8.275 kg, 63.9 moles, 3 equiv) was charged into the reactor. The reactor was chilled to 10-15° C. and 13.7 kg levulinic anhydride (63.9 mol, 3 equiv) was transferred into the reactor. When the addition was complete, the reaction was warmed to ambient temperature and stirred overnight or 12-16 hours. Completeness of the reaction was monitored by TLC (40:60 ethyl acetate/hexane) and HPLC. When the reaction was complete, 20 L of 10% citric acid, 10 L of water and 25 L of ethyl acetate were transferred into the reactor. The mixture was stirred for 30 min and the layers were separated. The organic layer (EtOAc layer) was extracted with 20 L of water, 20 L 5% sodium bicarbonate and 20 L 25% brine solutions. The ethyl acetate solution was dried in 4-6 Kg of anhydrous sodium sulfate. The solution was evaporated to a syrup (bath temp. 40° C.) and dried overnight. The yield of the isolated syrup of BMod1 was 100%.

Synthesis of the BA Dimer

Step 2. Preparation of BMod2, TFA Hydrolysis of BMod1

A 100 L reactor was charged with 9.296 Kg of 4-Lev Monomer B1 (BMod1) (21.3 mol, 1 equiv). The reactor chiller was turned to <5° C. and stirring was begun, after which 17.6 L of 90% TFA solution (TFA, 213 mole, 10 equiv) was transferred into the reactor. When the addition was complete, the reaction was monitored by TLC and HPLC. The reaction took approximately 2-3 hours to reach completion. When the reaction was complete, the reactor was chilled and 26.72 L of triethylamine (TEA, 19.4 Kg, 191.7 mole, 0.9 equiv) was transferred into the reactor. An additional 20 L of water and 20 L ethyl acetate were transferred into the reactor. This was stirred for 30 min and the layers were separated. The organic layer was extracted (EtOAc layer) with 20 L 5% sodium bicarbonate and 20 L 25% brine solutions. The ethyl acetate solution was dried in 4-6 Kg of anhydrous sodium sulfate. The solution was evaporated to a syrup (bath temp. 40° C.). The crude product was purified in a 200 L silica column using 140-200 L each of the following gradient profiles: 50:50, 80:20 (EtOAc/heptane), 100% EtOAc, 5:95, 10:90 (MeOH/EtOAc). The pure fractions were pooled and evaporated to a syrup. The yield of the isolated syrup, BMod2 was 90%.

Synthesis of the BA Dimer

Step 3. Preparation of BMod3, Silylation of BMod2

A 100 L reactor was charged with 6.755 Kg 4-Lev-1,2-DiOH Monomer B1 (BMod2) (17.04 mol, 1 equiv), 2328 g of imidazole (34.2 mol, 2 equiv) and 30 L of dichloromethane. The reactor was purged with nitrogen and chilled to −20° C., then 5.22 L tert-butyldiphenylchloro-silane (TBDPS-Cl, 5.607 Kg, 20.4 mol, 1.2 equiv) was transferred into the reactor. When addition was complete, the chiller was turned off and the reaction was allowed to warm to ambient temperature. The reaction was monitored by TLC (40% ethyl acetate/hexane) and HPLC. The reaction took approximately 3 hours to reach completion. When the reaction was complete, 20 L of water and 10 L of DCM were transferred into the reactor and stirred for 30 min, after which the layers were separated. The organic layer (DCM layer) was extracted with 20 L water and 20 L 25% brine solutions. Dichloromethane solution was dried in 4-6 Kg of anhydrous sodium sulfate. The solution was evaporated to a syrup (bath temp. 40° C.). The yield of BMod3 was about 80%.

Synthesis of the BA Dimer

Step 4. Preparation of BMod4, Benzoylation

A 100 L reactor was charged with 8.113 Kg of 4-Lev-1-Si-2-OH Monomer B1 (BMod3) (12.78 mol, 1 equiv), 9 L of pyridine and 30 L of dichloromethane. The reactor was purged with nitrogen and chilled to −20° C., after which 1.78 L of benzoyl chloride (2155 g, 15.34 mol, 1.2 equiv) was transferred into the reactor. When addition was complete, the reaction was allowed to warm to ambient temperature. The reaction was monitored by TLC (40% ethyl acetate/heptane) and HPLC. The reaction took approximately 3 hours to reach completion. When the reaction was complete, 20 L of water and 10 L of DCM were transferred into the reactor and stirred for 30 min, after which the layers were separated. The organic layer (DCM layer) was extracted with 20 L water and 20 L 25% brine solutions. The DCM solution was dried in 4-6 Kg of anhydrous sodium sulfate. The solution was evaporated to a syrup (bath temp. 40° C.). Isolated syrup BMod4 was obtained in 91% yield.

Synthesis of the BA Dimer

Step 5. Preparation of BMod5, Desilylation

A 100 L reactor was charged with 8.601 Kg of 4-Lev-1-Si-2-Bz Monomer B1 (BMod4) (11.64 mol, 1 equiv) in 30 L terahydrofuran. The reactor was purged with nitrogen and chilled to 0° C., after which 5.49 Kg of tetrabutylammonium fluoride (TBAF, 17.4 mol, 1.5 equiv) and 996 mL (1045 g, 17.4 mol, 1.5 equiv) of glacial acetic acid were transferred into the reactor. When the addition was complete, the reaction was stirred at ambient temperature. The reaction was monitored by TLC (40:60 ethyl acetate/hexane) and HPLC. The reaction took approximately 6 hours to reach completion. When the reaction was complete, 20 L of water and 10 L of DCM were transferred into the reactor and stirred for 30 min, after which the layers were separated. The organic layer (DCM layer) was extracted with 20 L water and 20 L 25% brine solutions. The dichloromethane solution was dried in 4-6 Kg of anhydrous sodium sulfate. The solution was evaporated to a syrup (bath temp. 40° C.). The crude product was purified in a 200 silica column using 140-200 L each of the following gradient profiles: 10:90, 20:80, 30:70, 40:60, 50:50, 60:40, 70:30, 80:20 (EtOAc/heptane) and 200 L 100% EtOAc. Pure fractions were pooled and evaporated to a syrup. The intermediate BMod5 was isolated as a syrup in 91% yield.

Synthesis of the BA Dimer

Step 6: Preparation of BMod6, TCA Formation

A 100 L reactor was charged with 5.238 Kg of 4-Lev-1-OH-2-Bz Monomer B1 (BMod5) (10.44 mol, 1 equiv) in 30 L of DCM. The reactor was purged with nitrogen and chilled to 10-15° C., after which 780 mL of diazabicyclo undecene (DBU, 795 g, 5.22 mol, 0.5 equiv) and 10.47 L of trichloro-acetonitrile (TCA, 15.08 Kg, 104.4 mmol, 10 equiv) were transferred into the reactor, Stirring was continued and the reaction was kept under a nitrogen atmosphere. After reagent addition, the reaction was allowed to warm to ambient temperature. The reaction was monitored by HPLC and TLC (40:60 ethyl acetate/heptane). The reaction took approximately 2 hours to reach completion. When the reaction was complete, 20 L of water and 10 L of dichloromethane were transferred into the reactor. This was stirred for 30 min and the layers were separated. The organic layer (DCM layer) was separated with 20 L water and 20 L 25% brine solutions. The dichloromethane solution was dried in 4-6 Kg of anhydrous sodium sulfate. The solution was evaporated to a syrup (bath temp. 40° C.). The crude product was purified in a 200 L silica column using 140-200 L each of the following gradient profiles: 10:90, 20:80, 30:70, 40:60 and 50:50 (EtOAc/Heptane). Pure fractions were pooled and evaporated to a syrup. The isolated yield of BMod6 was 73%.

Synthesis of the BA Dimer

Step 7. Preparation of AMod1, Acetylation of Monomer A2

A 100 L reactor was charged with 6.772 Kg of Monomer A2 (17.04 mole, 1 eq.), 32.2 L (34.8 Kg, 340.8 moles, 20 eq.) of acetic anhydride and 32 L of dichloromethane. The reactor was purged with nitrogen and chilled to −20° C. When the temperature reached −20° C., 3.24 L (3.63 Kg, 25.68 mol, 1.5 equiv) of boron trifluoride etherate ($BF_3.Et_2O$) was transferred into the reactor. After complete addition of boron trifluoride etherate, the reaction was allowed to warm to room temperature. The completeness of the reaction was monitored by HPLC and TLC (30:70 ethyl acetate/heptane). The reaction took approximately 3-5 hours for completion. When the reaction was complete, extraction was performed with 3×15 L of 10% sodium bicarbonate and 20 L of water. The organic phase (DCM) was evaporated to a syrup (bath temp. 40° C.) and allowed to dry overnight. The syrup was purified in a 200 L silica column using 140 L each of the following gradient profiles: 5:95, 10:90, 20:80, 30:70, 40:60 and 50:50 (EtOAc/heptane). Pure fractions were pooled and evaporated to a syrup. The isolated yield of AMod1 was 83%.

Synthesis of the BA Dimer

Step 8. Preparation of AMod3, 1-Methylation of AMod1

A 100 L reactor was charged with 5891 g of acetyl Monomer A2 (AMod1) (13.98 mole, 1 eq.) in 32 L of dichloromethane. The reactor was purged with nitrogen and was chilled to 0° C., after which 2598 mL of trimethylsilyl iodide (TMSI, 3636 g, 18 mol, 1.3 equiv) was transferred into the reactor. When addition was complete, the reaction was allowed to warm to room temperature. The completeness of the reaction was monitored by HPLC and TLC (30:70 ethyl acetate/heptane). The reaction took approximately 2-4 hours to reach completion. When the reaction was complete, the mixture was diluted with 20 L of toluene. The solution was evaporated to a syrup and was co-evaporated with 3×6 L of toluene. The reactor was charged with 36 L of dichloromethane (DCM), 3.2 Kg of dry 4 A Molecular Sieves, 15505 g (42 mol, 3 equiv) of tetrabutyl ammonium iodide (TBAI) and 9 L of dry methanol. This was stirred until the TBAI was completely dissolved, after which 3630 mL of diisopropyl-ethylamine (DIPEA, 2712 g, 21 moles, 1.5 equiv) was transferred into the reactor in one portion. The completion of the reaction was monitored by HPLC and TLC (30:70 ethyl acetate/heptane). The reaction took approximately 16 hours for completion. When the reaction was complete, the molecular sieves were removed by filtration. Added were 20 L EtOAc and extracted with 4×20 L of 25% sodium thiosulfate and 20 L 10% NaCl solutions. The organic layer was separated and dried with 8-12 Kg of anhydrous sodium sulfate. The solution was evaporated to a syrup (bath temp. 40° C.). The crude product was purified in a 200 L silica column using 140-200 L each of the following gradient profiles: 5:95, 10:90, 20:80, 30:70 and 40:60 (EtOAcTheptane). The pure fractions were pooled and evaporated to give intermediate AMod3 as a syrup. The isolated yield was 75%.

Synthesis of the BA Dimer

Step 9. Preparation of AMod4, DeAcetylation of AMod3

A 100 L reactor was charged with 4128 g of 1-Methyl 4,6-Diacetyl Monomer A2 (AMod3) (10.5 mol, 1 equiv) and 18 L of dry methanol and dissolved, after which 113.4 g (2.1 mol, 0.2 equiv) of sodium methoxide was transferred into the reactor. The reaction was stirred at room temperature and monitored by TLC (40% ethyl acetate/hexane) and HPLC. The reaction took approximately 2-4 hours for completion. When the reaction was complete, Dowex 50W×8 cation resin was added in small portions until the pH reached 6-8. The Dowex 50W×8 resin was filtered and the solution was evaporated to a syrup (bath temp. 40° C.). The syrup was diluted with 10 L of ethyl acetate and extracted with 20 L brine and 20 l, water. The ethyl acetate solution was dried in 4-6 Kg of anhydrous sodium sulfate. The solution was evaporated to a syrup (bath temp. 40° C.) and dried overnight at the same temperature. The isolated yield of the syrup AMod4 was about 88%.

Synthesis of the BA Dimer

Step 10. Preparation of AMod5,6-Benzoylation

A 100 L reactor was charged with 2858 g of Methyl 4,6-diOH Monomer A2 (AMod4) (9.24 mol, 1 equiv) and co-evaporated with 3×10 L of pyridine. When evaporation was complete, 15 L of dichloromethane, 6 L of pyridine were transferred into the reactor and dissolved. The reactor was purged with nitrogen and chilled to −40° C. The reactor was charged with 1044 mL (1299 g, 9.24 mol, 1 equiv) of benzoyl chloride. When the addition was complete, the reaction was allowed to warm to −10° C. over a period of 2 hours. The reaction was monitored by TLC (60% ethyl acetate/hexane). When the reaction was completed, the solution was evaporated to a syrup (bath temp. 40° C.). This was co-evaporated with 3×15 L of toluene. The syrup was diluted with 40 L ethyl acetate. Extraction was carried out with 20 L of water and 20 L of brine solution. The Ethyl acetate solution was dried in 4-6 Kg of anhydrous sodium sulfate. The solution was evaporated to a syrup (bath temp. 40° C. The crude product was purified in a 200 L silica column using 140-200 L each of the following gradient profiles: 5:95, 10:90, 20:80, 25:70 and 30:60 (EtOAc/heptane). The pure fractions were pooled and evaporated to a syrup. The isolated yield of the intermediate AMod5 was 84%.

Step 11: Crystallization of AMod5

The crude solid (10 grams) of AMod5 was dissolved in 500 ml of heptane at 50-60° C. The solution was cooled to room temperature and left stand for 16 hour at this temperature. The resulting white crystalline was isolated by filtration yielding 9.10 grams (92%).

Synthesis of the BA Dimer

Step 11. Preparation of BA1, Coupling of Amod5 with BMod6

A 100 L reactor was charged with 3054 g of methyl 4-Hydroxy-Monomer A2 (AMod5) from Step 10 (7.38 mol, 1 equiv) and 4764 g of 4-Lev-1-TCA-Monomer B1 (BMod6) from Step 6 (7.38 mol, 1 equiv). The combined monomers were dissolved in 20 L of toluene and co-evaporated at 40° C. Co evaporation was repeated with an additional 2×20 L, of toluene, after which 30 L of dichloromethane (DCM) was transferred into the reactor and dissolved. The reactor was purged with nitrogen and was chilled to below −20° C. When the temperature was between −20° C. and −40° C., 1572 g (1404 mL, 11.12 moles, 1.5 equiv) of boron trifluoride etherate ($BF_3.Et_2O$) were transferred into the reactor. After complete addition of boron trifluoride etherate, the reaction was allowed to warm to 0° C. and stirring was continued. The completeness of the reaction was monitored by HPLC and TLC (40:70 ethyl acetate/heptane). The reaction required 3-4 hours to reach completion. When the reaction was complete, 926 mL (672 g, 6.64 mol, 0.9 equiv) of triethylamine (TEA) was transferred into the mixture and stirred for an additional 30 minutes, after which 20 L of water and 10 L of dichloromethane were transferred into the reactor. The solution was stirred for 30 min and the layers were separated. The organic layer (DCM layer) was separated with 2×20 L water and 20 L 25% 4:1 sodium chloride/sodium bicarbonate solution. The dichloromethane solution was dried in 4-6 Kg of anhydrous sodium sulfate. The solution was evaporated to a syrup (bath temp. 40° C.) and used in the next step. The isolated yield of the disaccharide BA1 was about 72%, Synthesis of the BA Dimer Step 12, Removal of Levulinate (Methyl[(methyl 2-O-benzoyl-3-O-benzyl-α-L-Idopyranosyluronate)-(1→4)-2-azido-6-O-benzoyl-3-O-benzyl]-2-deoxy-α-D-glucopyranoside)

A 100 L reactor was charged with 4.104 Kg of 4-Lev BA Dimer (BA1) (4.56 mol, 1 equiv) in 20 L of THF. The reactor was purged with nitrogen and chilled to −20 to −25° C., after which 896 mL of hydrazine hydrate (923 g, 18.24 mol, 4 equiv) was transferred into the reactor. Stirring was continued and the reaction was monitored by TLC (40% ethyl acetate/heptane) and HPLC. The reaction took approximately 2-3 hour for the completion, after which 20 L of 10% citric acid, 10 L of water and 25 L of ethyl acetate were transferred into the reactor. This was stirred for 30 min and the layers were separated. The organic layer (ETOAc layer) was extracted with 20 L 25% brine solutions. The ethyl acetate solution was dried in 4-6 Kg of anhydrous sodium sulfate. The solution was evaporated to a syrup (bath temp. 40° C.). The crude product was purified in a 200 L silica column using 140-200 L each of the following gradient profiles: 10:90, 20:80, 30:70, 40:60 and 50:50 (EtOAc/heptane). The pure fractions were pooled and evaporated to dryness. The isolated yield of the BA Dimer was 82%. Formula: $C_{42}H_{43}N_3O_{13}$; Mol. Wt, 797.80.

Synthesis of the EDC Trimer

Step 1. Preparation of EMod1, Acetylation

A 100 L reactor was charged with 16533 g of Monomer E: (45 mole, 1 eq.), 21.25 L acetic anhydride (225 mole, 5 eq.) and 60 L of dichloromethane. The reactor was purged with nitrogen and was chilled to −10° C. When the temperature was at −10° C., 1.14 L (1277 g) of boron trifluoride etherate ($BF_3.Et_2O$, 9.0 moles, 0.2 eq) were transferred into the reactor. After the complete addition of boron trifluoride etherate, the reaction was allowed to warm to room temperature. The completeness of the reaction was monitored by TLC (30:70 ethyl acetate/heptane) and HPLC. The reaction took approximately 3-6 hours to reach completion. When the reaction was completed, the mixture was extracted with 3×50 L of 10% sodium bicarbonate and 50 L of water. The organic phase (DCM) was evaporated to a syrup (bath temp. 40° C.) and allowed to dry overnight. The isolated yield of EMod1 was 97%.

Synthesis of the EDC Trimer

Step 2. Preparation of EMod2, De-Acetylation of Azidoglucose

A 100 L reactor was charged with 21016 g of 1,6-Diacetyl Monomer E (EMod1) (45 mole, 1 eq.), 5434 g of hydrazine acetate ($NH_2NH_2.HOAc$, 24.75 mole, 0.55 eq.) and 50 L of DMF (dimethyl formamide). The solution was stirred at room temperature and the reaction was monitored by TLC (30% ethyl acetate/hexane) and HPLC. The reaction took approximately 2-4 hours for completion. When the reaction was completed, 50 L of dichloromethane and 40 L of water were transferred into the reactor. This was stirred for 30 minutes and the layers were separated. This was extracted with an additional 40 L of water and the organic phase was dried in 6-8 Kg of anhydrous sodium sulfate. The solution was evaporated to a syrup (bath temp. 40° C.) and dried overnight at the same temperature. The syrup was purified in a 200 L silica column using 140-200 L each of the following gradient profiles: 20:80, 30:70, 40:60 and 50:50 (EtOAc/heptane). Pure fractions were pooled and evaporated to a syrup. The isolated yield of intermediate EMod2 was 100%.

Synthesis of the EDC Trimer

Step 3. Preparation of EMod3, Formation of 1-TCA

A 100 L reactor was charged with 12752 g of 1-Hydroxy Monomer E (EMod2) (30 mole, 1 eq.) in 40 L of dichloromethane. The reactor was purged with nitrogen and stirring was started, after which 2.25 L of DBU (15 moles, 0.5 eq.) and 15.13 L of trichloroacetonitrile (150.9 moles, 5.03 eq) were transferred into the reactor. Stirring was continued and the reaction was kept under nitrogen. After the reagent addition, the reaction was allowed to warm to ambient temperature. The reaction was monitored by TLC (30:70 ethyl acetate/H-eptane) and HPLC. The reaction took approximately 2-3 hours to reach completion. When the reaction was complete, 40 L of water and 20 L of DCM were charged into the reactor. This was stirred for 30 min and the layers were separated. The organic layer (DCM layer) was extracted with 40 L water and the DCM solution was dried in 6-8 Kg of anhydrous sodium sulfate. The solution was evaporated to a syrup (bath temp. 40° C.). The crude product was purified in a 200 L silica column using 140-200 L each of the following gradient profiles: 10:90 (DCM/EtOAc/heptane), 20:5:75 (DCM/EtOAc/heptane) and 20:10:70 DCM/EtOAc/heptane). Pure fractions were pooled and evaporated to give Intermediate EMod3 as a syrup. Isolated yield was 53%.

Synthesis of the EDC Trimer CB

Step 4. (Glycosylation) Coupling of E-TCA with DC Building Block 118.0 gram (174.64 mmol, 1 eq) of DCBB and 299.60 gram (523.92 mmol, 3 eq) of E-Mod 3 was dissolved in 250 ml of Toluene and evaporated to dryness. The resulting syrup was co-evaporated with Toulene (3×300 ml) to dryness and place in vacuum for 2 hours. Then dried syrup was dissolved in 1180 ml of dried Dichloromethane, and cooled to −40.0° C. Then 23.08 gram (87.32 mmol, 0.5 eq) of Triethylsilyl Triflate (TES-Triflate) was added while maintaining the temperature between −40.0° C. to −25.0° C. When the addition was complete, the reaction mixture was immediately warmed to room temperature and stirred for 2 hours under Argon atmosphere. TLC (35% ethyl acetate/heptane) indicated that the reaction had gone to completion. The reaction mixture was cooled to 0° C. and quenched with 15.91 gram, (158 mmol, 0.9 eq/TES Triflate) of Triethylamine (TEA), stirred for additional 30 min. Water (180 mil) was added and the reaction was extracted with an additional 150 ml of Dichloromethane. The organic layer was extracted with a 25% (4:1) Sodium Chloride/Sodium Bicarbonate solution (2×180 ml), dried over anhydrous sodium sulfate, filtered and evaporated to dryness. The residue was purified by silica gel column chromatography (5% gradient ethyl acetate in heptane) as white foam of EDC-Trimer-CB (122 g, 65%).

Modification of EDC-Timer-CB

Step: 1 Formation of EDC-1-C.: Anhydro Ring Opening & Acetylation

6-O-acetyl-2-azido-2-deoxy-3,4-di-O-benzyl-α-D-glucopyranosyl-(1→4)-O-[benzyl-2,3-O-dibenzyl-β-D-glucopyranosyluronate]-(1→4)-O-2-azido-2-deoxy-1,3,6-tri-O-acetyl-β-D-glucopyranose 122.0 gram (112.43 mmol, 1 eq) of EDC-Trimer-CB was dissolved in Dried Dichloromethane and 307.45 ml (3372.90 mmol, 30 eq) of Acetic anhydride was added. The solution was cooled to −45 to −35° C. and 118.20 ml (899.44 mmol, 8 eq) of Boron Trifluoride Etherate was added slowly. Upon completion of addition, the reaction mixture was warmed to room temperature and stirred for 6 hours until reaction was completed by TLC (35% ethyl acetate/haptane). The reaction mixture was cooled to −10° C. and cautiously quenched with saturated solution of sodium bicarbonate and Stirred for additional 1 hrs. Then mixture was extracted with an additional 2 lit of Dichloromethane. The organic layer was extracted with brine (1×1.5 Lit), dried over anhydrous sodium sulfate and concentrated under vacuum to a syrup. The residue was purified by silica gel column chromatography (10% gradient ethyl acetate in heptane) as white foam of EDC-1-CB (86 gram, 65%).

Step: 2 Preparation of EDC-2-CB: Deacetylation

6-O-acetyl-2-azido-2-deoxy-3,4-di-O-benzyl-α-D-glucopyranosyl-(1→4)-[benzyl-2,3-O-dibenzyl-β-D-glucopyranosyluronate]-(1→4)-O-2-azido-2-deoxy-3,6-di-O-acetyl-1-β-D-glucopyranose To 86 gram (72.44 mmol, 1 eq) of EDC-1-CB was dissolved in 360 ml of dried Tetrahydrofuran (THF) and chilled to 5-10° C. Then, 77.62 gram (724.39 mmol, 10 eq) of Benzylamine was added slowly while maintaining the reaction temperature below 15° C. The reaction mixture was stirred for 4 hours. TLC (40% ethyl acetate/heptane) indicated that the reaction had gone to completion. The reaction mixture was dilutes with 1 Lit of ethyl acetate and extracted with 10% citric acid solution (2×300 ml). The organic layer was then extracted with saturated sodium bicarbonated solution (1×200 ml), brine (1×200 ml) and water (1×200 ml).

The organic layer was dried using anhydrous sodium sulfate and evaporated to dryness. The residue was purified by silica gel column chromatography (60% gradient ethyl acetate in heptane) as white foam of EDC-2-CB (52 gram, 62%).

Step: 3 Formation of EDC-3-CB: Formation of TCA Derivative

6-O-acetyl-2-azido-2-deoxy-3,4-di-O-benzyl-α-D-glucopyranosyl-(1→4)-O-[benzyl. 2,3-O-dibenzyl-β-D-glucopyranzsyluronate]-(1→4)-O-2-azido-2-deoxy-3,6-di-acetyl-1-O-trichloroacetimidoyl-β-D-glucopyranose

Synthesis of EDCBA Pentamer-CB

Coupling of EDC-3-CB with BA Dimer

Methyl O-6-O-acetyl-2-azido-2-deoxy-3,4-di-O-benzyl-α-D-glucopyranosyl)-(1→4)-O-[benzyl-2,3-O-dibenzyl-β-D-glucopyranosyluronate]-(1→4)-O-2-azido-2-deoxy-3,6-di-O-acetyl-α-D-glucopyranosyl-(1→4)-O-[methyl 2-O-benzoyl-3-O-benzyl-α-L-Idopyranosyluronate]-(1→4)-2-azido-6-O-benzoyl-3-O-benzyl-2-deoxy-α-D-glucopyranoside A solution of 46.0 gram (35.67 mmol, 1 eq) of EDC-3-CB and 56.92 gram (74.34 mmol, 2 eq) of BA dimer in 200 ml of Toluene was evaporated to dryness. The resulting syrup was co-evaporated with an additional (2×300 ml) of toluene. The dried syrup was then dissolved in dried 185 ml of Dichloromethane (DCM) and cooled to −40° C. The reaction mixture was slowly added 9.43 gram (35.68 mmol, 0.5 eq) of Triethylsilyl Triflate (TES-Triflate). When addition was complete, the reaction was warmed up to the room temperature

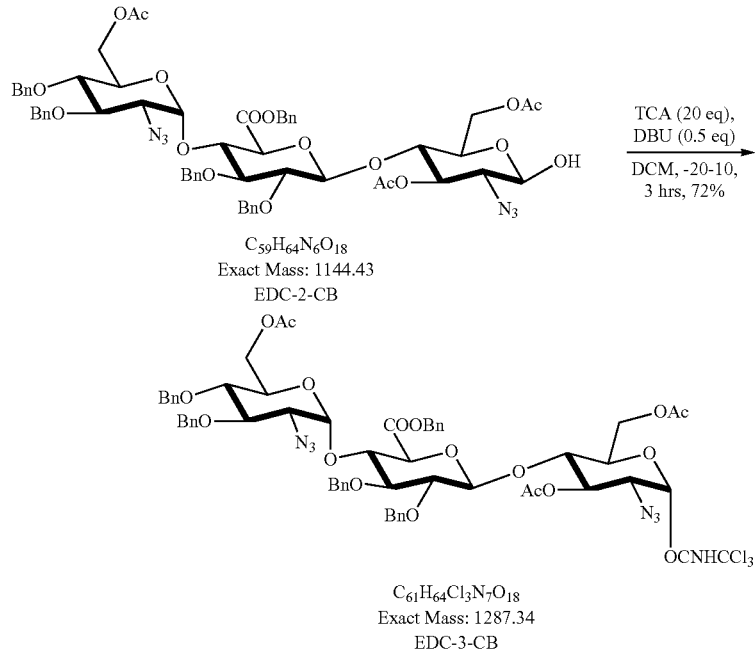

To 52.0 gram (45.40 mmol, 1 eq) of EDC-2-CB in 300 ml of dried Dichloromethane (DCM) was added 126.10 ml (899.43 mmol, 20 eq) of Trichloroacetonitrile (TCA). The solution was cooled to 0°-5° C. and 3.36 ml (22.49 mmol, 0.5 eq) of Diazabicycloundecene (DBU) was added. The reaction mixture was allowed to warm to 10° C. and stirred for 3 hours or until reaction was completed. The reaction mixture was diluted with 150 ml of water and extracted with addition 250 ml of dichloromethane. The organic layer was dried with anhydrous sodium sulfate, filtered, and concentrated to dryness and co-evaporated with toluene (2×100 ml) to a syrup. Column chromatographic separation using silica get and 5-50% ethyl acetate/heptane gave 46 gram (78%) of EDC-3-CB.

and stirred for 2 hours under Argon atmosphere. The reaction was considered completed by TLC (45% ethyl acetate/heptane). The reaction mixture was cooled to 0-5° C. and quenched by adding slowly 4.33 gram (42.81 mmol, 5.55 ml, 1.2 eq) of Triethylamine (TEA). The reaction mixture was extracted with 185 ml of water and 100 ml of dichloromethane. The organic layer was then extracted with 25% (4:1) saturated sodium bicarbonate and brine solution (2×150 ml), dried over anhydrous sodium sulfate, filtered and evaporated to dryness. Column chromatographic separation using silica get and 5-50%, ethyl acetate/heptane gave 49.0 gram (71%) of fully protected EDCBA Pentamer-CB [also referred to as fully protected pentamer, FPP] as white form.

Conversion of FPP to Fondaparinux Sodium Via Cellobiose with Obn on C-2 of Ring D)

Step: 1 Preparation of API-1-CB: Saponification of EDCBA Pentamer-CB

Methyl O-2-azido-2-deoxy-3,4-di-O-benzyl-α-D-glucopyranosyl-(1→4)-O-2,3-O-dibenzyl-β-D-glucopyranosyluronosyl-(1→4)-O-2-azido-2-deoxy-α-D-glucopyranosyl-(1→4)-O-3-benzyl-α-L-Idopyranosyluronosyl-(1→4)-2-azido-3-O-benzyl-2-deoxy-α-D-glucopyranoside disodium salt To a solution of 43.6 gram (22.65 mmol, 1 eq) of EDCBA Pentamer-CB in 523 mL of dioxane and 785 mL of tetrahydrofuran (TI-IF) was added. 872 mL of 0.7 M (0.610 mmol, 27 eq) Lithium hydroxide solution followed by 102 mL (1.0 mol, 44 eq) of 30% hydrogen peroxide. The reaction mixture was stirred for 16 hours. Then, 193 mL (0.77 mol, 34 eq) of 4 N sodium hydroxide solutions was added. The reaction was allowed to stir for an additional 24-48 hours. The reaction mixture was then extracted with 1.5 Lit of ethyl acetate. The organic layer was extracted with 900 ml of brine solution and dried with anhydrous sodium sulfate. Evaporation of the solvent under vacuum and co-evaporated with toluene (1×395 mL) to gave syrup of API-1-CB. The crude product was used for next step without further purification.

Step: 2 Preparation of API-2-CB: O-Sulfonation of API-1-CB

Methyl O-2-azido-2-deoxy-3,4-di-O-benzyl-6-O-sulfo-α-D-glucopyranosyl-(1→4)-O-2,3-O-dibenzyl-β-D-glucopyranosyluronosyl-(1→4)-O-2-azido-2-deoxy-3,6-di-O-sulfo-α-D-glucopyranosyl-(1→4)-O-3-O-benzyl-2-O-sulfo-α-L-idopyranuronosyl-(1→4)-2-azido-2-deoxy-6-O-sulfo-α-D-glucopyranoside, heptasodium salt The crude product 39.6 gram (26.64 mmol, 1 eq) of API-1-CB obtained in previous step 1 was dissolved in 1.0 Lit of dry Dimethylformamide (DMF). To this was added a previously prepared solution containing 211.68 gram (1.33 mol, 50 eq) of sulfur trioxide-pyridine complex in 205 mL of pyridine and 512 mL of Dimethylformamide (DMF). The reaction mixture was heated to 60° C. for additional 45 minutes. After stirring 2 hours at 60° C., the reaction was cooled to 20° C. and was quenched into 3 Lit of 8% sodium bicarbonate solution that was kept at 10° C. The pH of the quench mixture was maintained at pH 7-9 by addition of sodium bicarbonate solution. The quenched mixture was stirred for 16 hours. When pH stabilized above ~7, the solution was diluted with water and the resulting mixture was purified using a preparative HPLC column packed with Amberchrom CG161-M and eluted with 90%-10% Methanol/water solution. The pure fraction was concentrated under vacuum to give a white solid 39.0 gram of API-2-CB (84.4% yield over 2 steps).

Step: 3 Preparation of API-3-CB: Hydrogenation

Methyl O-2-amino-2-deoxy-6-O-sulfo-α-D-glucopyranosyl-(1→4)-O-2-O-hydroxyl-β-D-glucopyranosyluronosyl-(1→4)-O-2-amino-2-deoxy-3,6-di-O-sulfo-α-D-glucopyranosyl-(1→4)-1-O-2-O-sulfo-α-L-idopyranuronosyl-(1→4)-2-amino-2-deoxy-6-O-sulfo-α-D-glucopyranoside, heptasodium salt A solution of 39.0 gram (19.13 mmol) of the O-sulfated pentasaccharide API-2-CB in methanol and water was treated with 30 wt % of palladium in Activated carbon under 100 psi of hydrogen pressure at room temperature for 24 hr or until completion of reaction. The mixture was concentrated to give 26 g (95.67%) of API-3-CB.

A solution of 1581 g (0.78 mol) of O-Sulfated pentasaccharide API2 in 38 L of Methanol and 32 L of water was treated with 30 wt % of Palladium in Activated carbon under 100 psi of Hydrogen pressure at 60-65° C. for 60 hours or until completion of reaction. The mixture was then filtered through 1.0µ and 0.2µ filter cartridges and the solvent evaporated under vacuum to give 942 g (80% yield) of API3 [also referred to as EDCBA(OSO$_3$)$_5$(NH$_2$)$_3$].

Preparation of Fondaparinux Sodium

Step 4: N-Sulfation of API-3-CB

Methyl O-2-deoxy-6-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-sulfo-α-L-idopyranuronosyl-(1→4)-2-deoxy-6-O-sulfo-2-(sulfoamino)-α-D-glucopyranoside, decasodium salt To a solution of 25.4 gram (16.80 mmol, 1 eq) of API-3-CB in 847 mL of water was slowly added 66.85 gram (446.88 mmol, 25 eq) of sulfur trioxide-pyridine complex, maintaining the pH of the reaction mixture at pH 9-9.5 during the addition using 2N sodium hydroxide solution. The reaction was allowed to stir for 4 hours at pH 9.0-9.5. When reaction was completed, the pH was adjusted 7.0 by using 70 mL of 50 mmol Ammonium acetate solution pH ~3.5. The resulting N-Sulfated Cellobiose mixture was purified using Ion-Exchange Chromatographic Column followed by desalting using size exclusion resin to gave gram (%) of the purified Fondaparinux Sodium form.

To a solution of 942 g (0.63 mol) of API3 in 46 L of water was slowly added 3.25 Kg (20.4 mol, 32 eq) of Sulfur trioxide-pyridine complex, maintaining the pH of the reaction mixture at pH 9-9.5 during the addition using 2 N sodium hydroxide solution. The reaction was allowed to stir for 4-6 hours at pH 9.0-9.5. When reaction was complete, the pH was adjusted to pH 7.0 using 50 mM solution of Ammonium acetate at pH 3.5. The resulting N-sulfated EDCBA(OSO$_3$)$_5$(NHSO$_3$)$_3$ mixture was purified using Ion-Exchange Chromatographic Column (Varian Preparative 15 cm HiQ Column) followed by desalting using a size exclusion resin or gel filtration (Biorad G25), The resulting mixture was then treated with activated charcoal and the purification by ion-exchange and desalting were repeated to give 516 g (47.6% yield) of the purified Fondaparinux sodium form.

We claim:

1. A process for the preparation of a monosaccharide AMod3 having the structure

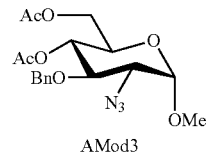

AMod3 comprising anhydro ring opening and acetylating the monomer IntA5 having the structure

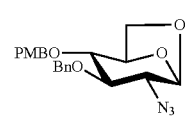

IntA5 to form a compound AMod 1 having the structure

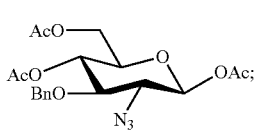

AMod1 and α-methylglycosylating the monomer AMod1 to form the monomer AMod3.

2. A process for the preparation of Fondaparinux sodium compound IntB1 having the structure

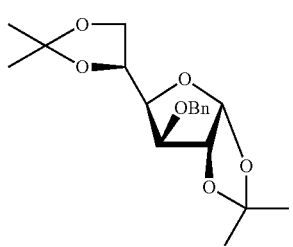

IntB1 comprising the step of:
(a) benzylating the compound SM-B having the structure

SM-B

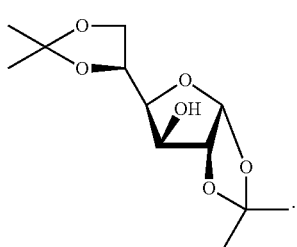

3. The process of claim 2, further comprising the steps:
(i) selectively hydrolyzing the compound IntB1 to form a compound IntB2 having the structure IntB2

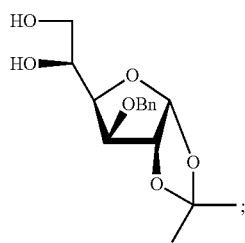

(ii) oxidatively cleaving the 5,6 dihydroxy group of the compound IntB2 to form a compound IntB3 having the structure IntB3

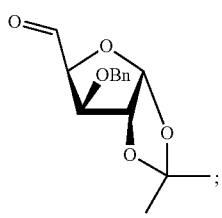

(iii) reacting the compound IntB3 with tris(phenylthio) methane to form a compound IntB4 having the structure IntB4

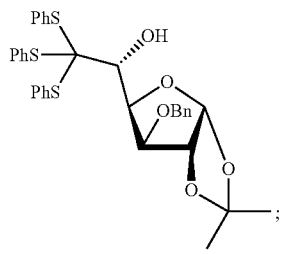

(iv) esterifying the compound IntB4 to form a compound IntB5 having the structure IntB5

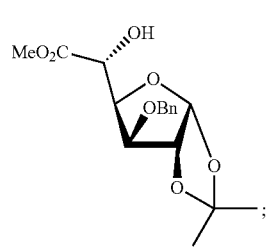

(v) cleaving the 1,2-isopropylidene group of the compound IntB5 to form a compound IntB6 having the structure IntB6

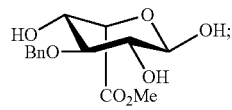

and
(vi) reacting the compound IntB6 with 2-methoxy propene to form Monomer B-1 having the structure Monomer B-1

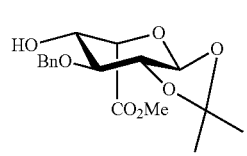

4. A process for preparing EDC-Trimer-CB of the formula

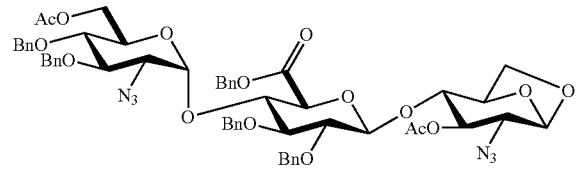

EDC-Trimer-CB comprising the steps:
(a) coupling an E monomer having the structure

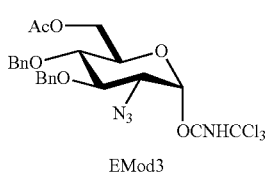

EMod3 to a DC Building Block having the structure
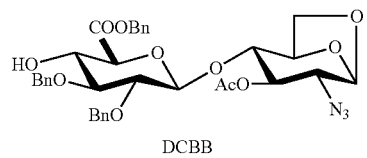
DCBB
to obtain EDC-Trimer-CB.
* * * * *